US010773010B2

(12) United States Patent
Phillips et al.

(10) Patent No.: US 10,773,010 B2
(45) Date of Patent: Sep. 15, 2020

(54) SUBCUTANEOUS VASCULAR ACCESS PORTS AND RELATED SYSTEMS AND METHODS

(71) Applicant: Advent Access Pte. Ltd., Singapore (SG)

(72) Inventors: Christopher M. Phillips, Salt Lake City, UT (US); Nathaniel P. Young, Salt Lake City, UT (US); Trent J. Perry, Kaysville, UT (US); Duane D. Blatter, Salt Lake City, UT (US); Mark A. Crawford, Sandy, UT (US); G. Doug Smith, Sandy, UT (US); Steven Johnson, Lehi, UT (US)

(73) Assignee: Advent Access Pte. Ltd., Singapore (SG)

( * ) Notice: Subject to any disclaimer, the term of this patent is extended or adjusted under 35 U.S.C. 154(b) by 221 days.

(21) Appl. No.: 15/923,854

(22) Filed: Mar. 16, 2018

(65) Prior Publication Data
US 2019/0060552 A1    Feb. 28, 2019

Related U.S. Application Data

(63) Continuation of application No. 14/792,486, filed on Jul. 6, 2015, now Pat. No. 9,968,726, which is a (Continued)

(51) Int. Cl.
*A61M 1/36* (2006.01)
*A61B 17/00* (2006.01)
(Continued)

(52) U.S. Cl.
CPC ....... *A61M 1/3653* (2013.01); *A61B 17/0057* (2013.01); *A61B 17/3423* (2013.01); (Continued)

(58) Field of Classification Search
CPC .... A61M 1/14; A61M 1/3653; A61M 1/3659; A61M 1/3661; A61M 39/0208; (Continued)

(56) References Cited

U.S. PATENT DOCUMENTS 484,681 A    10/1892    Smith
544,148 A    8/1895    Welter
(Continued)

FOREIGN PATENT DOCUMENTS

CN    1213319    4/1999
DE    102008034364 A1    2/2009
(Continued)

OTHER PUBLICATIONS

Brunette et al., "Titanium in Medicine: Material Science, Surface Science, Engineering, Biological Responses and Medical Applications," Berlin; Springer, 2001, ISBN 3-540-66936-1, p. 727.
(Continued)

*Primary Examiner* — Benjamin J Klein
(74) *Attorney, Agent, or Firm* — Cesari & Mckenna, LLP

(57) ABSTRACT

Ports for accessing a vessels within a patient include passageways that can guide needles or other access devices directly into the vessels. The ports can be implanted subcutaneously within a patient. Some ports may be used in the creation and use of vascular access buttonholes.

20 Claims, 45 Drawing Sheets

Related U.S. Application Data continuation of application No. 12/697,192, filed on Jan. 29, 2010, now Pat. No. 9,072,880.

(60) Provisional application No. 61/148,372, filed on Jan. 29, 2009, provisional application No. 61/229,023, filed on Jul. 28, 2009.

(51) Int. Cl.
  *A61B 17/34* (2006.01)
  *A61M 39/02* (2006.01)
  *A61M 1/14* (2006.01)

(52) U.S. Cl.
  CPC ............ *A61M 1/14* (2013.01); *A61M 1/3659* (2014.02); *A61M 1/3661* (2014.02); *A61M 39/0208* (2013.01); *A61B 2017/00641* (2013.01); *A61B 2017/00654* (2013.01); *A61B 2017/3425* (2013.01); *A61M 2039/0223* (2013.01); *A61M 2039/0226* (2013.01); *A61M 2039/0238* (2013.01); *A61M 2205/0238* (2013.01)

(58) Field of Classification Search
  CPC .. A61M 2205/0238; A61M 2039/0223; A61M 2039/0226; A61M 2039/0238; A61B 17/0057; A61B 17/3423; A61B 2017/00641; A61B 2017/00654; A61B 2017/3425
  See application file for complete search history.

(56) References Cited

U.S. PATENT DOCUMENTS

| | | | |
|---|---|---|---|
| 669,586 | A | 3/1901 | Levasseur |
| 2,828,744 | A | 4/1958 | Hirsch |
| 3,094,122 | A | 6/1963 | Gauthier |
| 3,782,381 | A | 1/1974 | Winnie |
| 3,998,222 | A | 12/1976 | Shihata |
| 4,013,080 | A | 3/1977 | Froning |
| 4,164,221 | A | 8/1979 | Bentley |
| 4,183,357 | A | 1/1980 | Bentley |
| 4,318,401 | A | 3/1982 | Zimmerman |
| 4,405,319 | A | 9/1983 | Cosentino |
| 4,423,730 | A | 1/1984 | Gabbay |
| 4,484,912 | A | 11/1984 | Raible |
| RE31,855 | E | 3/1985 | Osborne |
| 4,559,033 | A | 12/1985 | Stephen |
| 4,667,673 | A | 5/1987 | Li |
| 4,781,695 | A | 11/1988 | Dalton |
| 4,822,341 | A | 4/1989 | Colone |
| 4,846,799 | A | 7/1989 | Tanaka |
| 4,861,341 | A * | 8/1989 | Woodburn ............ A61M 5/158 604/175 |
| 4,878,904 | A | 11/1989 | Callaway |
| 4,906,236 | A | 3/1990 | Alberts |
| 4,973,317 | A | 11/1990 | Bobrove |
| 5,092,849 | A | 3/1992 | Sampson |
| 5,127,412 | A | 7/1992 | Cosmetto |
| 5,222,963 | A | 6/1993 | Brinkerhoff |
| 5,222,974 | A | 6/1993 | Kensey |
| 5,232,442 | A | 8/1993 | Johnson |
| 5,263,930 | A * | 11/1993 | Ensminger ........ A61M 39/0208 604/175 |
| 5,275,322 | A | 1/1994 | Brinkerhoff |
| 5,281,199 | A | 1/1994 | Ensminger |
| 5,282,827 | A | 2/1994 | Kensey |
| 5,306,254 | A | 4/1994 | Nash |
| 5,334,217 | A | 8/1994 | Das |
| 5,350,360 | A | 9/1994 | Ensminger |
| 5,356,381 | A * | 10/1994 | Ensminger et al. ......................... A61M 39/0208 604/181 |
| 5,441,517 | A | 8/1995 | Kensey |
| 5,527,277 | A | 6/1996 | Ensminger |
| 5,534,008 | A | 7/1996 | Acksel |
| 5,540,715 | A | 7/1996 | Katsaros |
| 5,630,833 | A | 5/1997 | Katsaros |
| 5,662,616 | A | 9/1997 | Bousquet |
| 5,676,689 | A | 10/1997 | Kensey |
| 5,707,393 | A | 1/1998 | Kensey |
| 5,741,228 | A | 4/1998 | Lambrecht |
| 5,792,104 | A | 8/1998 | Speckman |
| 5,817,113 | A | 10/1998 | Gifford, III |
| 5,823,983 | A | 10/1998 | Rosofsky |
| 5,848,989 | A | 12/1998 | Villani |
| 5,861,004 | A | 1/1999 | Kensey |
| 5,882,341 | A | 3/1999 | Bousquet |
| 5,910,133 | A | 6/1999 | Gould |
| 5,989,213 | A | 11/1999 | Maginot |
| 6,004,301 | A | 12/1999 | Carter |
| 6,004,341 | A | 12/1999 | Zhu |
| 6,007,563 | A | 12/1999 | Nash |
| 6,007,576 | A | 12/1999 | McClellan |
| 6,019,788 | A | 2/2000 | Butters |
| 6,090,130 | A | 7/2000 | Nash |
| 6,099,508 | A | 8/2000 | Bousquet |
| 6,156,016 | A | 12/2000 | Maginot |
| 6,190,371 | B1 | 2/2001 | Maginot |
| 6,213,973 | B1 | 4/2001 | Eliasen |
| 6,261,255 | B1 | 7/2001 | Mullis |
| 6,261,257 | B1 | 7/2001 | Uflacker |
| 6,287,322 | B1 | 9/2001 | Zhu |
| 6,355,020 | B1 | 3/2002 | Bousquet |
| 6,425,901 | B1 | 7/2002 | Zhu |
| 6,475,207 | B1 | 11/2002 | Maginot |
| 6,508,790 | B1 | 1/2003 | Lawrence |
| 6,524,326 | B1 | 2/2003 | Zhu |
| 6,527,754 | B1 | 3/2003 | Tallarida |
| 6,544,206 | B1 | 4/2003 | Johnston, Jr. |
| 6,551,334 | B2 | 4/2003 | Blatter |
| 6,569,173 | B1 | 5/2003 | Blatter |
| 6,585,705 | B1 | 7/2003 | Maginot |
| 6,595,941 | B1 | 7/2003 | Blatter |
| 6,623,494 | B1 | 9/2003 | Blatter |
| 6,626,863 | B1 | 9/2003 | Berler |
| 6,626,921 | B1 | 9/2003 | Blatter |
| 6,656,151 | B1 | 12/2003 | Blatter |
| 6,682,489 | B2 | 1/2004 | Tenerz |
| 6,723,084 | B1 | 4/2004 | Maginot |
| 6,726,704 | B1 | 4/2004 | Loshakove |
| 6,726,711 | B1 | 4/2004 | Langenbach |
| 6,733,515 | B1 | 5/2004 | Edwards |
| 6,743,218 | B2 | 6/2004 | Maginot |
| 6,743,244 | B2 | 6/2004 | Blatter |
| 6,764,500 | B1 | 7/2004 | Muijs Van De Moer |
| 6,913,609 | B2 * | 7/2005 | Yencho .................. A61B 17/11 604/167.01 |
| 6,960,185 | B2 | 11/2005 | Adaniya |
| 6,964,675 | B2 | 11/2005 | Zhu |
| 6,979,338 | B1 | 12/2005 | Loshakove |
| 6,997,914 | B2 | 2/2006 | Smith |
| 7,008,412 | B2 | 3/2006 | Maginot |
| 7,022,131 | B1 | 4/2006 | Derowe |
| 7,025,741 | B2 | 4/2006 | Cull |
| 7,044,916 | B2 | 5/2006 | Tenerz |
| 7,060,084 | B1 | 6/2006 | Loshakove |
| 7,063,711 | B1 | 6/2006 | Loshakove |
| 7,073,509 | B2 | 7/2006 | Tenerz |
| 7,118,546 | B2 | 10/2006 | Blatter |
| 7,128,734 | B1 | 10/2006 | Wilson |
| 7,160,311 | B2 | 1/2007 | Blatter |
| 7,261,705 | B2 | 8/2007 | Edoga |
| 7,285,097 | B2 | 10/2007 | Tenerz |
| 7,331,981 | B2 | 2/2008 | Cates |
| 7,396,359 | B1 | 7/2008 | Derowe |
| 7,708,722 | B2 | 5/2010 | Glenn |
| 7,828,781 | B2 | 11/2010 | Edoga |
| 7,901,417 | B2 | 3/2011 | Blatter |
| 7,909,804 | B2 | 3/2011 | Stats |
| 7,922,734 | B2 | 4/2011 | Blatter |
| 8,034,064 | B2 | 10/2011 | Blatter |

(56) References Cited

U.S. PATENT DOCUMENTS

| | | |
|---|---|---|
| 8,277,437 B2 | 10/2012 | Saal |
| 8,337,464 B2 | 12/2012 | Young |
| 8,337,465 B2 | 12/2012 | Young |
| 8,343,028 B2 | 1/2013 | Gregoric |
| 8,348,882 B2 | 1/2013 | Bardy |
| 8,398,654 B2 | 3/2013 | Franklin |
| 8,409,228 B2 | 4/2013 | Blatter |
| 8,574,204 B2 | 11/2013 | Bourne |
| 8,585,663 B2 | 11/2013 | Powers |
| 8,668,706 B2 | 3/2014 | Blatter |
| 8,690,816 B2 | 4/2014 | Dakin |
| 8,747,359 B2 | 6/2014 | Pakter |
| 9,033,931 B2 | 5/2015 | Young |
| 9,039,717 B2 | 5/2015 | Blatter |
| 9,179,901 B2 | 11/2015 | Young |
| 9,937,296 B2 | 4/2018 | Peh |
| 2001/0007931 A1 | 7/2001 | Blatter |
| 2001/0037094 A1 | 11/2001 | Adaniya |
| 2001/0056266 A1 | 12/2001 | Tallarida |
| 2002/0077658 A1 | 6/2002 | Ginn |
| 2002/0087127 A1 | 7/2002 | Finch |
| 2003/0004520 A1 | 1/2003 | Haarala |
| 2003/0023208 A1 | 1/2003 | Osypka |
| 2003/0078597 A1 | 4/2003 | Blatter |
| 2003/0089757 A1 | 5/2003 | Whitman |
| 2004/0097994 A1 | 5/2004 | Blatter |
| 2004/0102804 A1 | 5/2004 | Chin |
| 2004/0133173 A1 | 7/2004 | Edoga |
| 2004/0199140 A1 | 10/2004 | Rue |
| 2004/0254537 A1 | 12/2004 | Conlon |
| 2004/0260333 A1 | 12/2004 | Dubrul |
| 2005/0125060 A1 | 6/2005 | Perry |
| 2005/0171565 A1 | 8/2005 | Yencho |
| 2005/0177176 A1 | 8/2005 | Gerbi |
| 2005/0283188 A1 | 12/2005 | Loshakove |
| 2006/0247605 A1 | 11/2006 | Edoga |
| 2007/0083156 A1 | 4/2007 | Muto |
| 2007/0123811 A1 | 5/2007 | Squitieri |
| 2007/0154509 A1 | 7/2007 | Wilcher |
| 2007/0265584 A1 | 11/2007 | Hickman |
| 2008/0051811 A1 | 2/2008 | Blatter |
| 2008/0086075 A1 | 4/2008 | Isik |
| 2008/0086100 A1 | 4/2008 | Isaacson |
| 2008/0147114 A1 | 6/2008 | Derowe |
| 2008/0195124 A1 | 8/2008 | Borghi |
| 2008/0243080 A1 | 10/2008 | Chang |
| 2008/0249509 A1 | 10/2008 | Glenn |
| 2008/0269659 A1 | 10/2008 | Bergin |
| 2009/0076466 A1 | 3/2009 | Quebbemann |
| 2009/0118683 A1 | 5/2009 | Hanson |
| 2009/0131919 A1 | 5/2009 | Davey |
| 2009/0192473 A1 | 7/2009 | Crocker |
| 2009/0195124 A1 | 8/2009 | Abramovich |
| 2009/0209918 A1 | 8/2009 | Berglund |
| 2009/0270835 A1 | 10/2009 | Kushner |
| 2010/0027422 A1 | 2/2010 | Fodil |
| 2010/0121358 A1 | 5/2010 | Blatter |
| 2010/0152640 A1 | 6/2010 | Golding |
| 2010/0152658 A1 | 6/2010 | Hanson |
| 2010/0191166 A1 | 7/2010 | Phillips |
| 2010/0191179 A1 | 7/2010 | Young |
| 2010/0191191 A1 | 7/2010 | Young |
| 2010/0274223 A1 | 10/2010 | Teitelbaum |
| 2010/0318016 A1 | 12/2010 | Nugent |
| 2011/0184347 A1 | 7/2011 | Mason |
| 2011/0213309 A1 | 9/2011 | Young |
| 2011/0288462 A1 | 11/2011 | Riesinger |
| 2012/0088977 A1* | 4/2012 | Glenn ............... A61M 39/0208 600/201 |
| 2012/0101525 A1 | 4/2012 | Jenson |
| 2012/0245536 A1 | 9/2012 | Gerber |
| 2013/0060200 A1 | 3/2013 | Dalton |
| 2013/0066282 A1 | 3/2013 | Dalton |
| 2013/0184725 A1 | 7/2013 | Blatter |
| 2013/0245550 A1 | 9/2013 | Young |
| 2013/0245572 A1 | 9/2013 | Young |
| 2014/0163588 A1 | 6/2014 | Blatter |
| 2014/0207086 A1 | 7/2014 | Stats |
| 2014/0309609 A1 | 10/2014 | Hsu |
| 2015/0190587 A1 | 7/2015 | Peh |
| 2018/0264246 A1 | 9/2018 | Lim |
| 2018/0272056 A1 | 9/2018 | Peh |
| 2018/0289550 A1 | 10/2018 | Ye |

FOREIGN PATENT DOCUMENTS

| | | |
|---|---|---|
| EP | 0356810 | 3/1990 |
| EP | 2583646 A1 | 4/2013 |
| GB | 2282760 | 4/1995 |
| JP | S5720272 | 2/1982 |
| JP | 08501008 | 2/1996 |
| JP | H11500031 | 1/1999 |
| JP | 2004518476 | 6/2004 |
| JP | 2005349121 | 12/2005 |
| JP | 2012516223 | 7/2012 |
| WO | 9535126 | 12/1995 |
| WO | 1998018506 | 5/1998 |
| WO | 1999033512 | 7/1999 |
| WO | 03082127 A1 | 10/2003 |
| WO | 2006045608 | 5/2006 |
| WO | 2006092724 | 9/2006 |
| WO | 2007109164 | 9/2007 |
| WO | 2009149474 | 12/2009 |
| WO | 2010011995 | 1/2010 |
| WO | 2010088532 | 8/2010 |
| WO | 2010088541 | 8/2010 |
| WO | 2010107698 | 9/2010 |
| WO | 2011094712 | 8/2011 |
| WO | 2013128292 | 9/2013 |
| WO | 2014017986 | 1/2014 |
| WO | 2015089372 | 6/2015 |

OTHER PUBLICATIONS

International Search Report and the Written Opinion of the International Searching Authority dated Dec. 13, 2018 in International Application No. PCT/IB2018/000437 (pp. 1-18).

International Search Report and the Written Opinion of the International Searching Authority dated Apr. 8, 2010 in International Application No. PCT/US2010/022622, now published as WO 2010/088541. (3 pages).

International Preliminary Report on Patentability dated Aug. 11, 2011 in International Application No. PCT/US2010/022622, now published as WO 2010/088541. (11 pages).

International Search Report and the Written Opinion of the International Searching Authority dated Mar. 25, 2011 in International Application No. PCT/US2011/023228, now published as WO 2011/094712. (9 pages).

International Preliminary Report on Patentability dated Jul. 31, 2012 in International Application No. PCT/US2011/023228. (7 pages).

Extended European Search Report dated Jul. 2, 2014 in European Application No. 11737838.0. (6 pages).

Extended European Search Report dated Mar. 4, 2015 in European Application No. 10736487.9. (6 pages).

International Search Report dated Apr. 8, 2010 in International Application No. PCT/US2010/022607, which claims priority to U.S. Appl. No. 61/148,372, filed Jan. 29, 2009 and U.S. Appl. No. 61/229,023, filed Jul. 28, 2009. (3 pages).

International Preliminary Report on Patentability dated Aug. 2, 2011 in International Application No. PCT/US2010/022607, which claims priority to U.S. Appl. No. 61/148,372, filed Jan. 29, 2009 and U.S. Appl. No. 61/229,023, filed Jul. 28, 2009. (9 pages).

International Search Report dated Jul. 31, 2009 in International Application No. PCT/US2009/046664, which claims priority to U.S. Appl. No. 61/059,590, filed Jun. 6, 2008. (3 pages).

International Preliminary Report on Patentability dated Dec. 6, 2010 in International Application No. PCT/US2009/046664, which claims priority to U.S. Appl. No. 61/059,590, filed Jun. 6, 2008. (8 pages).

(56) References Cited

OTHER PUBLICATIONS

Vascular Access 2006, American Journal of Kidney Disease, vol. 48 No. 1, Jul. 2006, S180-S182.
Form PCT ISA 206—International Application No. PCT/IB2018/000437; International Filing Date: Apr. 4, 2018 (10 pages).
Jennings, et al., "The Venous Window Needle Guide, a hemodialysis cannulation device for salvage of uncannulatable arteriovenous fistulas", Journal of Vascular Surgery, Oct. 2014, vol. 60, No. 4, pp. 1024-1032.

* cited by examiner

SUBCUTANEOUS VASCULAR ACCESS PORTS AND RELATED SYSTEMS AND METHODS

CROSS-REFERENCE TO RELATED APPLICATIONS

This application is a continuation of U.S. patent application Ser. No. 14/792,486, filed on Jul. 6, 2015, titled METHODS FOR IMPLANTING SUBCUTANEOUS VASCULAR ACCESS PORTS, which is a continuation of U.S. patent application Ser. No. 12/697,192, filed on Jan. 29, 2010, titled SUBCUTANEOUS VASCULAR ACCESS PORTS AND RELATED SYSTEMS AND METHODS, corresponding to U.S. Pat. No. 9,072,880, which claims the benefit under 35 U.S.C. § 119(e) of U.S. Provisional Patent Application No. 61/148,372, titled VASCULAR ACCESS METHODS, APPARATUS AND SYSTEMS, filed on Jan. 29, 2009, and of U.S. Provisional Patent Application No. 61/229,023, titled SURGICALLY IMPLANTED DIRECT VASCULAR ACCESS PORT METHOD AND APPARATUS, filed on Jul. 28, 2009, the entire contents of each of which are hereby incorporated by reference herein.

STATEMENT REGARDING FEDERALLY SPONSORED RESEARCH OR DEVELOPMENT

The invention was made with support from the U.S. Government under Grant No. SBIR R43 CA 139608 and Grant No. SBIR R44 CA 139608, which were awarded by the National Institutes of Health. The U.S. Government has certain rights in the invention.

TECHNICAL FIELD

The present disclosure relates to subcutaneous vascular access ports and related systems and methods.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
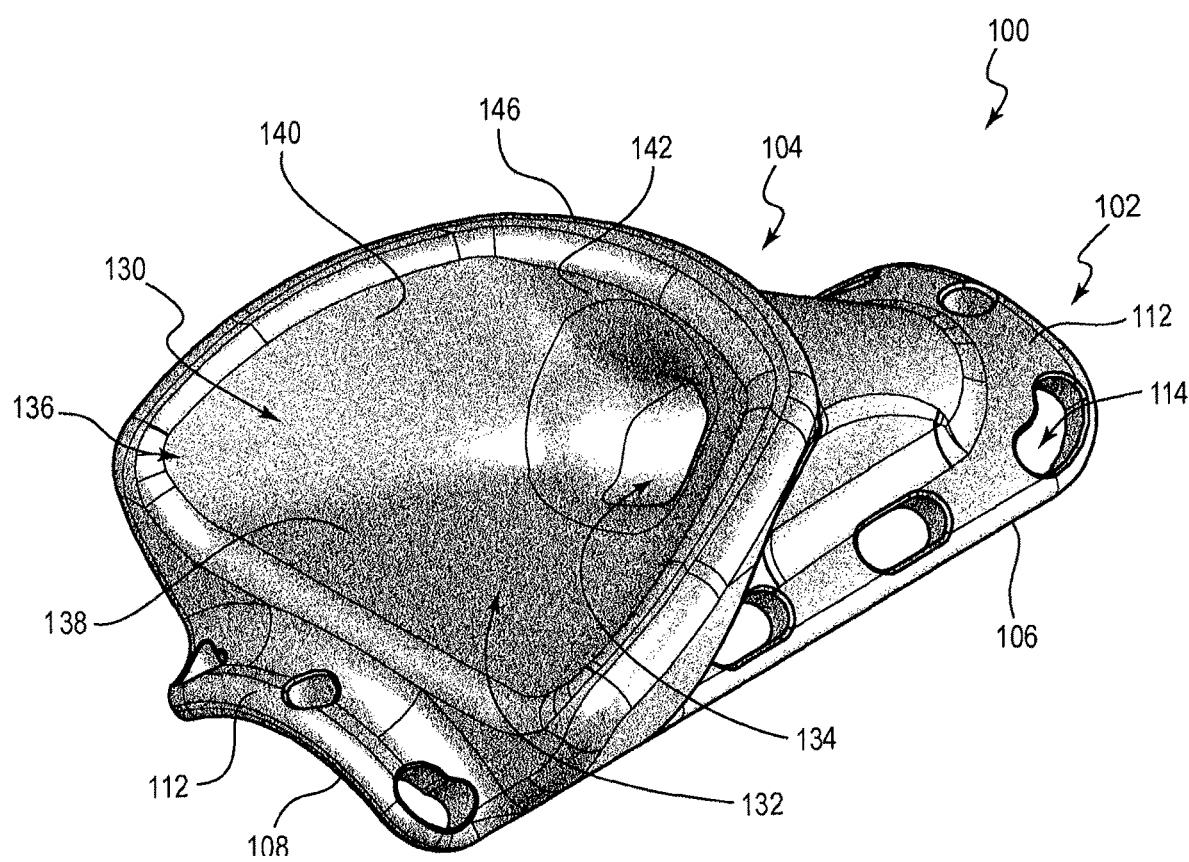
FIG. 1 is a perspective view of an embodiment of a vascular access port.
Figure 2:
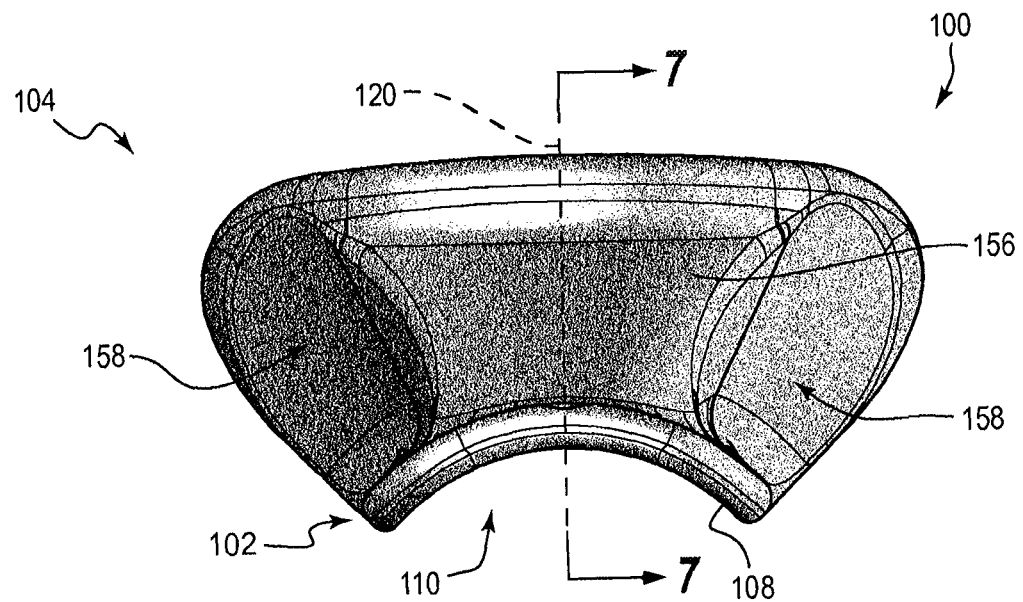
FIG. 2 is a front elevation view thereof.

Certain embodiments of vascular access ports described herein are configured to be implanted subcutaneously in a patient for relatively long or indefinite periods. The vascular access ports can be implanted in any suitable manner and can be substantially fixed relative to a vessel wall once implanted. For example, in some implantation methods, a bottom surface of a vascular access port placed in contact with the tunica adventitia of a vessel and the port is secured to the vessel via one or more sutures that extend through at least a portion of every layer of the vessel. In further embodiments, a portion of the tunica adventitia is separated or removed from a blood vessel such that the bottom surface of a port is relatively close to the tunica media layer of the blood vessel, and the port is secured to the vessel via one or more sutures that extend through at least a portion of the tunica adventitia layer and substantially entirely through the media and the tunica intima layers. The surface of the port that contacts the vessel wall can comprise an opening through which an access device, such as a needle, can be inserted into a lumen of the blood vessel. The vascular access ports can be well-suited for buttonhole cannulation techniques in which buttonhole access sites are created in vessel walls and/or are used to access the vessels. The term "buttonhole" is used herein in its ordinary sense in the field of vascular access (e.g., in the field of hemodialysis), particularly in the context of cannulation techniques, and the term can include single-site cannulation holes that are approximately the same size as access devices that are inserted therethrough (e.g., needles or other cannulation devices), and that can permit relatively easy insertion of the access devices as compared with other areas along a vessel wall. Similarly, the ports can be well-suited for the creation and/or use of tracts through the skin of a patient through which the buttonholes can be repeatedly accessed. These and other features and advantages of various embodiments of vascular access ports, of systems that employ the ports, and of methods of implanting and using the ports will be apparent from the disclosure herein.

FIGS. 1-7 illustrate an embodiment of a vascular access port 100. The vascular access port 100 includes a base 102 and a body 104. In the illustrated embodiment, the base 102 and the body 104 are integrally formed as a unitary piece, and the body 104 extends away from the base 102. The base 102 is elongated in a longitudinal direction. In particular, the illustrated base 102 defines a substantially rectangular perimeter 106 that extends a greater distance in a longitudinal direction than it does in a transverse direction (see, e.g., FIG. 5). The edges and corners of the rectangular perimeter 106 can be rounded, which can prevent trauma to surrounding tissue when the vascular access port 100 is implanted.

The base 102 can include a base surface or bottom surface 108 that is configured to face a vessel when the vascular access port 100 is coupled to the vessel. The bottom surface 108 can be configured to conform to a contour of a wall of the vessel. For example, the bottom surface 108 of the base 102 can be bowed in the transverse direction and can have a radius of curvature that is substantially the same as a radius of curvature of an outer surface of a vessel to which the vascular access port 100 is to be attached. The bowed bottom surface 108 can define a cavity 110 (see FIGS. 2 and 3) into which at least a portion of a circumference of a vessel can be received. In the illustrated embodiment, the width and the curvature of the bottom surface 108 are such that the cavity 110 is sized to receive a substantial portion of the circumference of a vessel therein. Such a configuration can permit the bottom surface 108 to form a stable contact with the vessel. Other suitable arrangements are also possible, as discussed below.

The base 102 can include one or more connection flanges 112 that extend about a least a portion of a periphery of the base 102. In the illustrated embodiment, a first connection flange 112 extends about a front end of the base 102 and a second connection flange 112 is at a back end of the base 102. One or more attachment channels or attachment passages 114 can extend through the connection flanges 112. The attachment passages 114 can be configured to permit one or more ties or attachment devices 116 to extend therethrough so as to attach the vascular access port 100 to a vessel (see, e.g., FIGS. 8, 9C, 10F, 11A, and 12), as discussed further below. Any suitable attachment devices 116 may be used, such as one or more sutures, pinch rings, hooks, or wires. Accordingly, in some embodiments, one or more of the attachment passages 114 may be referred to as suture holes. As further discussed below, in the illustrated embodiment, the base 102 includes a centrally situated attachment passage 114 at each of the front and rearward ends thereof.

Figure 3:
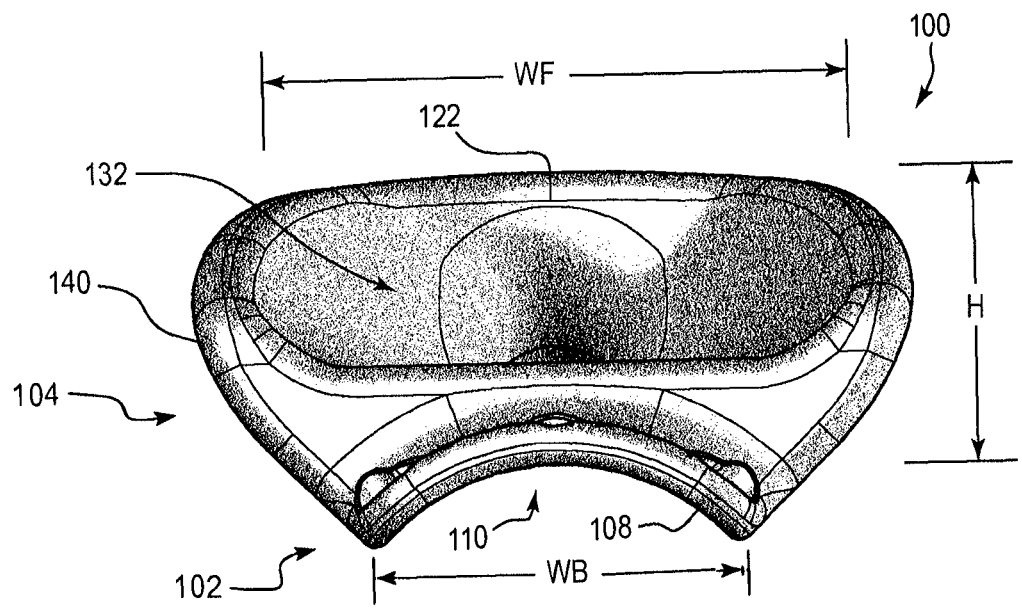
FIG. 3 is a rear elevation view thereof.
Figure 4:
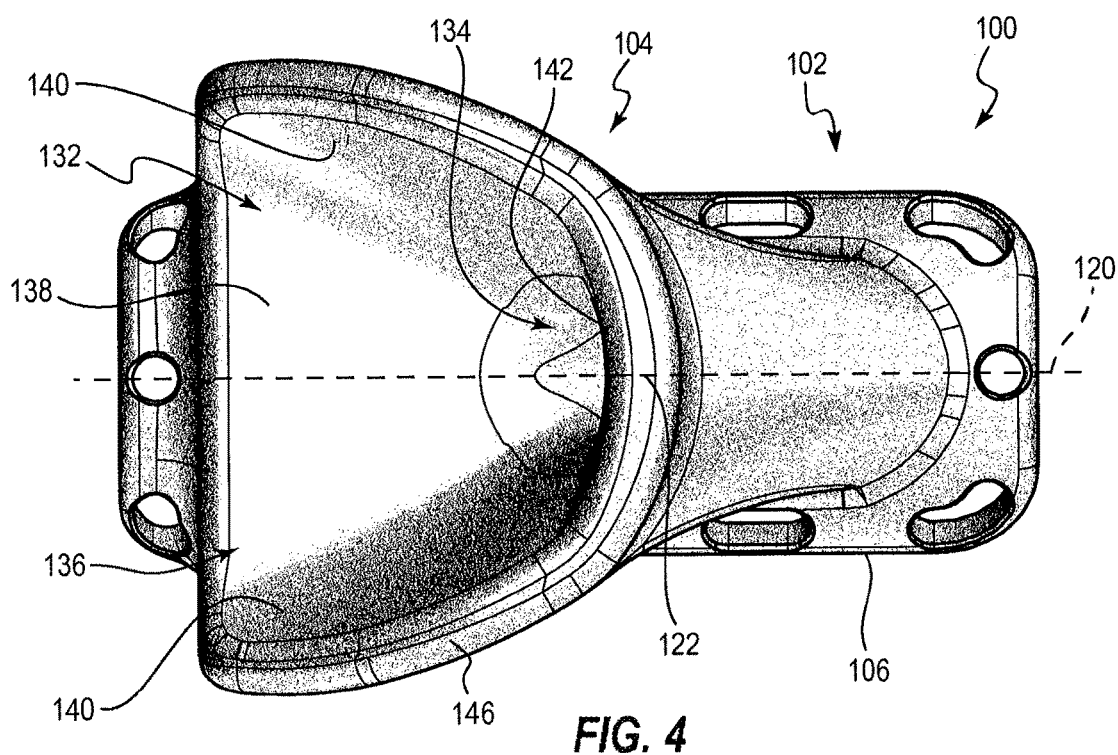
FIG. 4 is a top plan view thereof.
Figure 6:
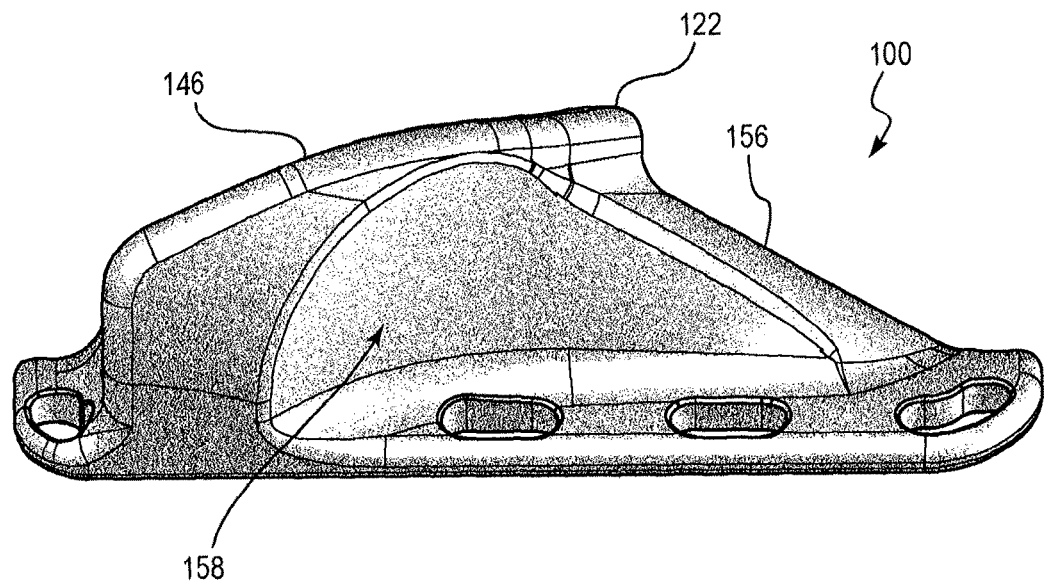
FIG. 6 is a right side elevation view thereof, wherein a left side elevation view is a mirror image of the right side elevation view.

The body 104 can extend upwardly from the base 102. In the illustrated embodiment, the body rises upwardly along a central vertical longitudinal plane 120 (see FIGS. 2 and 4) of the vascular access port 100. With reference to FIG. 4, the body 104 can expand outwardly from the central vertical longitudinal plane 120 and can widen in a rearward direction. Additionally, as shown in FIGS. 3, 4, and 6, a pinnacle region 122 of the body 104 can be positioned along the central vertical longitudinal plane 120 and at approximately a longitudinal center of the body 104. It is noted that directional terms, such as bottom, front, and rearward, are used relative to the orientation of the vascular access port 100 shown in FIG. 1. Such directional terms are not intended to limit the possible orientations of the vascular access port 100 within a patient. For example, in some embodiments, the front end of the vascular access port 100 may be oriented upstream from the rearward end thereof when the port 100 is coupled to a vessel, whereas in other embodiments, the front end may be oriented downstream from the rearward end.

Figure 5:
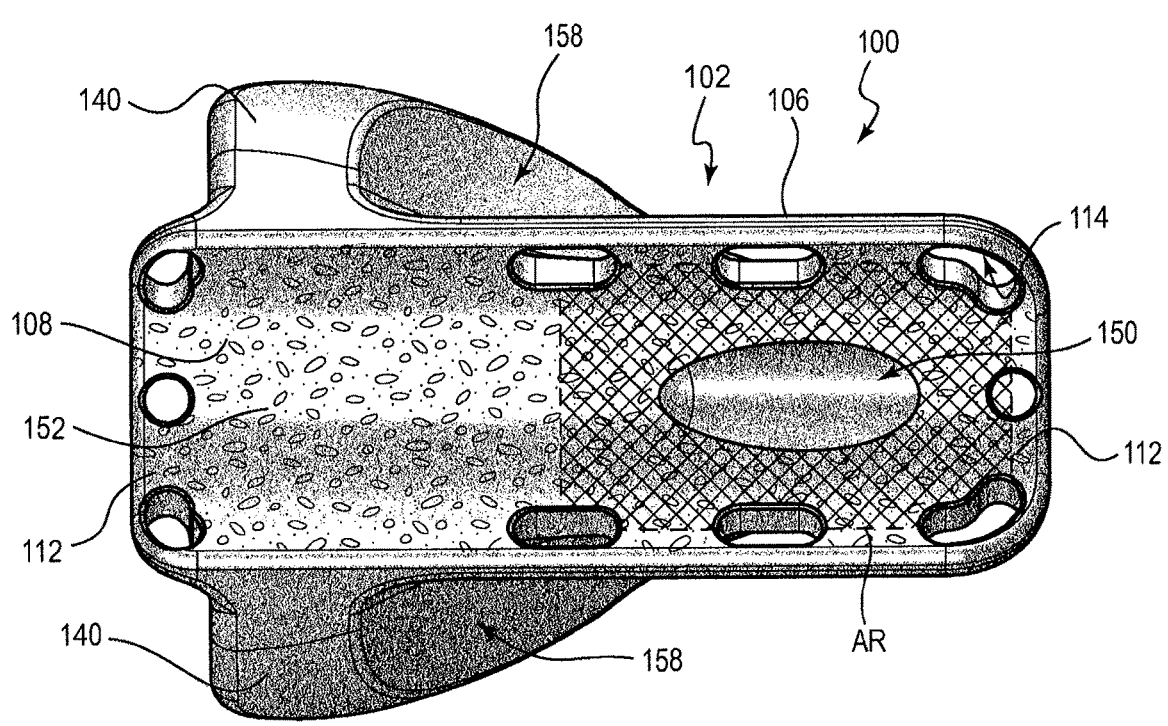
FIG. 5 is a bottom plan view thereof.
Figure 7:
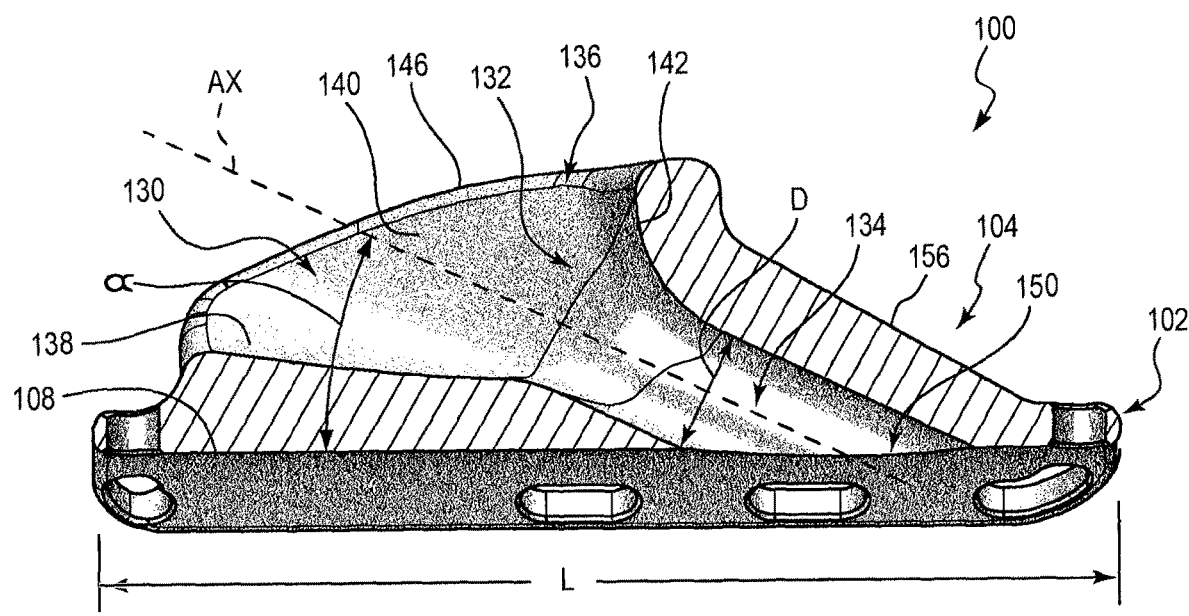
FIG. 7 is a cross-sectional view of the vascular access port of FIG. 1 taken along the view line 7-7 in FIG. 2.

A guidance passageway 130 can extend through the body 104. In the illustrated embodiment, the guidance passageway 130 includes a funnel region 132 and a channel 134. The funnel region 132 defines a relatively large entry mouth 136, which extends about or circumscribes the proximal end or proximal opening thereof, and the funnel region 132 narrows from the entry mouth 136 in a forward and downward direction. In the illustrated embodiment, a forward end of the funnel region 132 transitions into the channel 134. The funnel region 132 can include a base surface 138 that projects rearwardly from the channel 134 and that flares outwardly in the rearward direction. As shown in FIG. 7, the base surface 138 of the funnel region 132 can be angled upwardly (in a rearward direction) relative to the bottom surface 108 of the base 102. The funnel region 132 can further include wings 140 that each curve upwardly and outwardly from the base surface 138 and that are each joined to a backstop portion 142 at a forward end thereof. As shown in FIGS. 4 and 5, the wings 140 can extend outwardly past the perimeter 106 of the base 102 so as to provide for a wide entry mouth 136 of the funnel region 132. The backstop portion 142 can rise upwardly from an upper surface of the channel 134 and may include a surface that is directed substantially vertically. The backstop portion 142 can span the channel 134, and at least a portion thereof can be positioned directly above the channel 134.

The funnel region 132 can fully encompass an entrance end of the channel 134 and can encourage a tip of an access device 144, such as a needle (see FIG. 11B), to enter the channel 134. The funnel region 132 thus can serve as an enlarged target area that can assist in directing an access device 144 to a desired portion of a vessel, as discussed further below. The funnel region 132 can comprise a material that can prevent or discourage a tip of an access device 144 from embedding therein or removing a portion thereof as the tip moves toward the channel 134. For example, in various embodiments, the funnel region 132 can comprise titanium, stainless steel, a rigid plastic, or a similar material.

At least a portion of the entry mouth 136 of the funnel region 132 can include a palpation projection 146, such as a palpation ridge. In the illustrated embodiment, the palpation projection 146 is substantially U-shaped and extends over the wings 140 and the backstop portion 142 of the funnel region 132, and the pinnacle region 122 of the body 104 is located at a forward end of the palpation projection 146. The palpation projection 146 can be rounded or radiused so as to be free from sharp edges that could lead to tissue erosion. As further discussed below, the palpation projection 146 can be used to locate the vascular access port 100 and/or confirm an orientation thereof when the port 100 is positioned subcutaneously in a patient.

The entry mouth 136 of the funnel region 132 may be used to assist in achieving hemostasis after removal of an access device 144 from the vascular access port 100. To this end, the palpation projection 146 may substantially define a plane, in some embodiments. As shown in FIG. 6, the palpation projection 146 of the illustrated embodiment is nearly or substantially planar, as it is not perfectly planar due to a slight curvature in the longitudinal direction. The palpation projection 146 also exhibits a slight curvature in the transverse direction, as can be seen in FIG. 3. Moreover, in the illustrated embodiment, a rearward edge of the entry mouth 136 smoothly transitions into the palpation projection 146 at either end thereof and is only slightly below the substantially planar region defined by the palpation projection 146. Accordingly, as further discussed below, a seal can readily be formed about a periphery of the entry mouth 136 of an implanted vascular access port 100 by pressing tissue that surrounds the port 100 against the entry mouth 136.

With reference to FIG. 7, the channel 134 can extend through the base 102, and a bottom end of the channel 134 can define an opening 150 in the bottom surface 108 of the base 102. The opening 150 may be referred to as a distal opening 150 of the guidance passageway 130. The channel 134 can be configured to constrain movement of one or more access devices 144 inserted individually therethrough along a predetermined or repeatable path toward the opening 150. Accordingly, when the vascular access device 100 is fixed relative to a vessel, the channel 134 and the opening 150 can cause the one or more access devices 144 to cannulate the same portion of the vessel. In certain embodiments, the channel 134 defines a substantially constant inner diameter D along a length thereof, which can constrain the movement of an access device 144 that has an outer diameter that is slightly smaller than the diameter D. For example, in the illustrated embodiment, the channel 134 is substantially cylindrical and can constrain movement of a substantially cylindrical access device 144 (e.g., a fistula needle) that has an outer diameter slightly smaller than the diameter D (see FIG. 11B). The diameter D and/or the length of the channel 134 can be selected to achieve a desired amount of constraint for a given access device 144.

With continued reference to FIG. 7, the channel 134 can define a central axis AX, which can define an acute angle α relative to the bottom surface 108. For example, in the illustrated embodiment, the axis AX and a longitudinal line along the bottom surface 108 form the angle α. In FIG. 7, the longitudinal line is represented in FIG. 7 by a line L that defines a longitudinal length of the base 10. When the vascular access port 100 is connected to a vessel, the longitudinal line L can be substantially parallel to a longitudinal axis of a lumen of the vessel (see FIG. 11A). Accordingly, in the illustrated embodiment, the channel 134 can constrain movement of an access device 144 along a path that is both nonparallel and non-orthogonal to the lumen of the vessel. In particular, the channel 134 can constrain movement of the access device 144 along a path that is at or is approximately at the angle α relative to the lumen of the vessel. In various embodiments, the angle α can have a value that is no greater than about 15, 20, 25, 30, 35, 45, or 60 degrees; can have a value that is no less than about 10, 15, 20, 25, 30, 35, 45, or 60 degrees; or can have a value that is within a range of from about 30 degrees to about 60 degrees, from about 15 degrees to about 45 degrees, or from about 20 degrees to about 35 degrees. As further discussed below, some protocols for the creation and use of buttonhole cannulation sites can require introduction of a needle into a vessel at a designated acute angle. Accordingly, certain embodiments of the vascular access port 100 can be configured for use with such protocols, and the angle α can be selected to correspond with the angle designated by the protocol.

As previously discussed, the diameter D defined by the channel 134 can be larger than a diameter of an access device 144 that is inserted through the channel 134. In some embodiments, the channel 134 is larger than the access device 144 by a sufficient amount to allow the access device 144 to pass through it easily or with little or no resistance. Reduction or elimination of insertion and removal forces between an access device 144 and the channel 134 can assist in maintaining a secure attachment between the vascular access port 100 and a vessel over the course of multiple insertion and removal events. Moreover, in the illustrated embodiment, the channel 134 is open, unobstructed, clear, free, or vacant. Stated otherwise, the channel 134 is devoid of closure apparatus, such as, for example, septums, valves, obturators, etc., which could be used to selectively open the channel 134 prior to or during insertion of an access device 144 therein, or which could be used to selectively close the channel 134 during or after removal of an access device 144 therefrom. The term "closure apparatus," as used herein, is directed to mechanical, electromechanical, or other synthetic, foreign, or non-native devices or systems that may be manufactured outside of a patient and introduced into a patient, but does not include natural or patient-generated materials that may close the channel 134, such as, for example, clotted blood, tissue ingrowth, or vascular structures, such as a neointima or a pseudo vessel wall.

In certain embodiments, a configuration of the channel 134, or more generally, the guidance passageway 130, can remain unchanged upon insertion of an access device 144 therein or removal of an access device 144 therefrom, which may result, at least in part, from an absence of closure apparatus within the channel 134 or the guidance passageway 130. More generally, a configuration of the vascular access port 100 can remain unchanged upon insertion of an access device 144 therein or removal of an access device 144 therefrom. Stated otherwise, in certain embodiments, no portion of one or more of the channel 134, the guidance passageway 130, and the vascular access port 100 may be deformed, rotated, translated, pivoted, expanded, contracted, or otherwise moved relative to remaining portions of one or more of the channel 134, the guidance passageway 130, and the vascular access port 100. Any resistive forces to the insertion or removal of an access device 144 that might be provided by closure apparatus thus are absent during use of the vascular access port 100. Methods by which hemostasis may be achieved via the vascular access port 100 in the absence of closure apparatus are discussed below.

Manufacture of embodiments of the vascular access port 100 can be facilitated by their lack of closure apparatus. For example, in the illustrated embodiment, the vascular access port 100 comprises a unitary piece and/or comprises a single material, and it is devoid of moving parts. Likewise, in the illustrated embodiment, the guidance passageway 130 is defined by a single unitary piece and/or by a single material, and it is devoid of moving parts. Other or further embodiments may comprise multiple parts that are fixedly attached to each other in a non-separable fashion. Embodiments of the vascular access port 100 can be manufactured via any suitable method, such as machining, die casting, injection molding, etc., and may comprise any suitable biocompatible material, such as, for example, titanium, stainless steel, rigid plastic, etc. In some embodiments, the vascular access port 100 comprises a resorbable material. For example, in various embodiments, the vascular access port 100 can comprise one or more of caprilactone and glycolide (e.g., Panacryl, in proportions of about 90% and 10%, respectively); ε-caprolactone; cellulose; ethylene oxide with propylene oxide (e.g., Pleuronic F-108); ethylene oxide with block polymer (e.g., DynaGraft proloxamer); glycolide, dioxanone, and trimethylene carbonate (e.g., Biosyn, in proportions of about 60%, 14%, and 26%, respectively); glycolide and ε-caprolactone (e.g., Monocryl); hyaluronic acid ester (e.g., Hyaff); poly(butylene-terephthalate)-co-(polyethyleneglycol) (e.g., Poly-active, Osteo-active); polydioxanon (e.g., PDS); polyethyleenoxyde, polyglactin (e.g. Vicryl, Vicryl Rapide, Vicryl Plus, Polysorb); poly-glecapron (e.g., Monocryl); polyglycolic acid (e.g., Dexon); polyglyconate (e.g., Maxon); polyglyceride (e.g., Trilucent); polylactic acid (e.g., PLLA); poly L-lactic acid (PLLA) and polyglycolic acid (PGA) (e.g., in proportions of about 82% and 18%, respectively); poly L-lactic acid (PLLA) and copolymer (e.g., Lactosorb); poly-L-lactide, poly-D-lactide, and polyglycolide; polyvinylalcohol (e.g., Bioinblue); polysaccharide; and propylene oxide.

In other embodiments, the vascular access port 100 can be formed of a combination of materials. For example, in some embodiments, the guidance passageway 130 can be formed of a material that remains rigid indefinitely, or for a relatively long period, such as titanium, stainless steel, or a first type of resorbable material, and other portions of the vascular access port 100 can comprise a resorbable material, such as, for example, a second type of resorbable material that is resorbed within the body of a patient much quicker than is the first type of resorbable material.

With reference to FIG. 5, the bottom surface 108 of the base 102 can include any suitable ingrowth-inducing covering 152, which can facilitate integration or ingrowth of tissue in order to provide or enhance an attachment between a vessel and the vascular access port 100. In some embodiments, the ingrowth-inducing covering comprises a porous or roughened texture, which can be formed in any suitable manner. For example, in some embodiments, the texture is provided by compaction and sintering of metallic beads or powders, such as titanium beads, onto the bottom surface 108. In some embodiments, the beads may have a diameter of about 5 thousandths of an inch (i.e., approximately 0.13 millimeters) or smaller. In other or further embodiments, the ingrowth-inducing covering 152 can be formed by machining, sandblasting, laser etching, or injection molding of the bottom surface 108, or by attaching to the bottom surface 108 a fabric, such as polyester, Dacron®, or e-PTFE.

The ingrowth-inducing covering 152 can extend over the entire bottom surface 108 of the base 102, as shown in the illustrated embodiment, or over a significant portion thereof. In some embodiments, it can be desirable for the ingrowth-inducing covering 152 to cover a region that is forward of and/or that encompasses the opening 150 so as to provide a secure attachment between a vessel and the base 102 in this region, which can assist in ensuring that access devices 144 inserted through the opening 150 are consistently and repeatedly directed to the same portion of the vessel. For example, an attachment area AR may be defined over which it is desirable to provide a secure attachment to a vessel. The attachment area AR may be encompassed by a series of attachment passages 114 through which one or more attachment devices 116 may be advanced through the sidewall of a vessel into the lumen of a vessel to couple the vascular access device 100 to a vessel. The attachment area AR likewise may be covered by the ingrowth-inducing covering 152 which can provide a further connection between the vascular access port 100 and an outer layer of the vessel (e.g., the adventitia or media). The attachment area AR can surround the opening 150, as shown. The attachment area AR may also be referred to as an attachment region.

In some embodiments, the base 102 can be provided with an adhesive (not shown) in addition to or instead of the ingrowth-inducing covering 152 to provide a secure attachment between the base 102 and a vessel. For example, in some embodiments, the adhesive can comprise cyanoacrylate or fibrin glue.

It can be desirable for the vascular access port 100 to be configured for sufficiently secure attachment to a vessel such that the port 100 remains fixed relative to the vessel when it is influenced by forces from a needle or other access device 144. For example, attachment devices 116 coupled to the attachment passages 114, tissue attached to the ingrowth-inducing covering 152, and/or a bond provided by adhesives can resist relative longitudinal movement between the vascular access port 100 and the vessel when a tip of the access device 144 is urged forwardly along the funnel region 132 or forwardly within the channel 134. Similarly, such attachment features can resist relative rotational movement between the vascular access port 100 and the vessel when a tip of the access device 144 presses downwardly on either of the wings 140.

In some embodiments, it can be desirable to constrain the ingrowth-inducing covering 152 to the bottom surface 108 of the base 102, such as when it is desired to discourage, inhibit, or prevent the body 104 from attaching to surrounding tissue when the vascular access port 100 is implanted in a patient. For example, vessels can be somewhat mobile relative to surrounding tissue, and it may be more desirable for the vascular access port 100 to remain fixed relative to a vessel rather than relative to the tissue that surrounds the vessel. Accordingly, in some embodiments, the body 104 is relatively smooth. In other embodiments, at least a portion of the body 104 can comprise an ingrowth-inducing covering 152.

In some embodiments, at least a portion of the vascular access port 100 can include a covering (not shown), such as a coating and/or an embedded portion, that comprises one or more materials or agents that provide antiseptic, antimicrobial, antibiotic, antiviral, antifungal, anti-infection, or other desirable properties to the vascular access port 100, such as the ability to inhibit, decrease, or eliminate the growth of microorganisms at or near a surface of the port. For example, in various embodiments, the vascular access port 100 can comprise one or more of silver, platinum, gold, zinc, iodine, phosphorus, bismuth, alexidine, 5-flurouracil, chlorhexidine, sulfadiazine, benzalkonium chloride, heparin, complexed heparin, benzalkonoium chloride, 2,3 dimercaptopropanol, ciprofloxacin, cosmocil, cyclodextrin, dicloxacillin, EDTA, EGTA, myeloperoxidase, eosinophil peroxidase, fusidic acid, hexyl bromide, triclosan, polymyxin B, isopropanol, minocycline rifampin, minocycline EDTA, octenidine, orthophenyl phenol, triclocarban, triclosan, cephazolin, clindamycin, dicloxacillin, fusidic acid, oxacillin, rifampin, antibodies, peptides, polypeptides, free fatty acids, and oxidative enzymes. In some embodiments, the coating and/or the embedded material may be separate or independent from (e.g., non-coextensive with) the ingrowth-inducing covering 152. For example, in some embodiments, the ingrowth-inducing covering 152 is constrained to the base 102 of the vascular access port 100, whereas an antimicrobial covering is constrained to the body 104 of the vascular access port 100.

In the illustrated embodiment, a forward face 156 of the body 104 rises smoothly from the base 102 and is angled rearwardly. As shown in FIG. 7, in some embodiments, the forward face 156 may generally follow a contour of the channel 134 and may be substantially parallel thererto. For example, the forward face 156 can be convexly rounded in a manner similar to the channel 134. The body 104 can smoothly transition from the forward face 156 into depressions 158 at either side thereof, which can provide for a relatively smaller surface area of the body to which tissue might attach. The depressions 158 also can reduce the material costs associated with manufacture of the vascular access port 100.

Various parameters of the vascular access port 100 can be adjusted or selected to achieve a desired performance. For example, with reference to FIG. 3, a maximum width WF of the funnel region 132 can be greater than a maximum width WB of the base 102. Such an arrangement may be desirable where the vascular access port 100 is configured to be coupled with a relatively small vessel, or where a relatively large target area otherwise is desired. In various embodiments, the width WF is no less than about 1.0, 1.25, 1.50, 1.75, or 2.0 times the value of the width WB.

In some embodiments, the width WB of the base 102 can be approximately the same as or smaller than a width of a vessel to which the vascular access port 100 is configured to be attached. In various embodiments, the width WB of the base 102 can be no less than about 6, 7, 8, 9, 10, 11 or 12 millimeters, or can be no more than about 6, 7, 8, 9, 10, 11, or 12 millimeters.

In some embodiments, a height H of the vascular access port 100 can be adjusted or selected depending on the depth at which the port 100 is to be implanted within the patient. For example, some embodiments of the vascular access port 100 may be well-suited for use with a shallow vessel, such as a vein associated with an arteriovenous fistula in a forearm, whereas other embodiments may be well-suited for use with deeper vessels, such as the basilic vein in the upper arm. The depth at which the port 100 is located beneath a surface of the skin of the patient also can vary from patient to patient due to differences in anatomy. Sites at which various embodiments of the vascular access port 100 can be implanted include the cephalic, basilic, femoral, jugular, subclavian, or other suitable veins; arteries; fistulas; the stomach; other organs; or, more generally, any suitable structure where a walled membrane encircles or encapsulates a region.

In some embodiments, it can be desirable for an implanted vascular access port 100 to be beneath the surface of the skin of a patient by a sufficient amount to prevent tissue erosion, yet not so deep that palpation of the vascular access port 100 is difficult or provides insufficient information regarding the position or orientation of the port. In various embodiments, a minimum distance between a surface of the skin of a patient and an implanted port is no more than about 3, 4, 5, or 6 millimeters, is no less than about 3, 4, 5, or 6 millimeters, or is about 3, 4, 5, or 6 millimeters.

The height H can be defined as a minimum distance between the pinnacle region 122 and the bottom surface 108 of the base 102, and the height H can be selected, adjusted, or otherwise configured so as to achieve a desired depth of the vascular access port 100 beneath the surface of the skin of a patient. In various embodiments, the height H can be no greater than about 2, 3, 4, 5, 6, 7, 8, 9, 10, 11, 12, 13, 14, or 15 millimeters, or can be no less than about 2, 3, 4, 5, 6, 7, 8, 9, 10, 11, 12, 13, 14, or 15 millimeters. In other or further embodiments, the height H can be no more than about 0.5, 0.75, 1.0, 1.5, 2.0, 2.5, 3.0, or 3.5 times the width WB of the base 102, or can be no less than about 0.5, 0.75, 1.0, 1.5, or 2.0, 2.5, 3.0, or 3.5 times the width WB of the base 102. In other or further embodiments, the angle α, as defined above, can vary with the height H. For example, in some embodiments, the angle α increases with increasing height H.

It will be appreciated that various features of the embodiments of the vascular access port 100 discussed above can be altered or modified. For example, in some embodiments, the base 102 and the body 104 comprise separate pieces that are joined to each other. For example, the base 102 may comprise a relatively compliant material that can readily change shape so as to conform to a surface of a vessel, while at least a portion of the body 104 (e.g., the funnel region 132) can comprise a relatively rigid material. In other or further embodiments, the cavity 110 defined by the base 102 can be sized to receive any portion of a circumference of a vessel therein. Different sizes and configurations of the guidance passageway 130 are also possible, as further discussed below.

The vascular access port 100 can be implanted in a patient and used in any suitable methods. As mentioned above, it can be desirable to secure the vascular access port 100 to a vessel in such a manner that the bottom opening 150 defined by the guidance passageway 130 is fixed relative to the vessel, which can allow the guidance passageway 130 and/or the opening 150 to repeatedly direct an access device to the same portion of the vessel.

Figure 8:
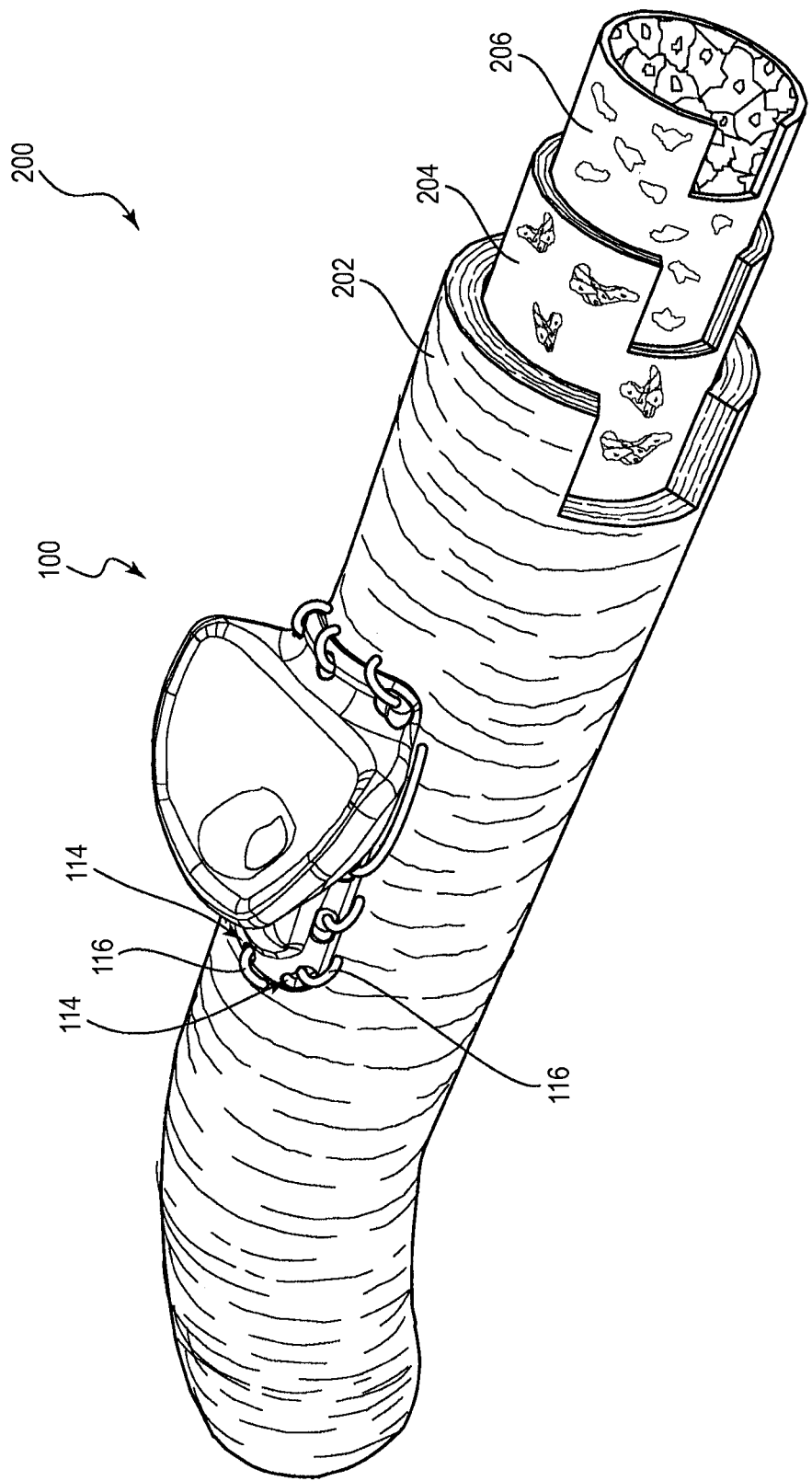
FIG. 8 is a perspective partial cutaway view of the vascular access port of FIG. 1 coupled with a vessel.

FIG. 8 depicts an example of one such arrangement. The vascular access port 100 is fixedly and directly secured to a vessel 200, which comprises three layers: the tunica adventitia (or adventitia) layer 202, the tunica media (or media) layer 204, and the tunica intima (or intima) layer 206. The term "direct," when used herein with reference to securing or attaching a vascular access port 100 to the vessel 200, means that some portion of the vascular access port 100 is in abutting contact with the vessel 200 and is fixedly attached thereto. In the illustrated embodiment, an attachment device 116 comprises a running suture that extends through each attachment passage 114 of the vascular access port 100. One or more loops of the suture can extend through all three layers 202, 204, 206 of the vessel 200.

In certain embodiments, it can be desirable to ensure that one or more attachment devices 116 extend through more layers of the vessel 200 than just the adventitia layer 202 (or a portion thereof), or stated otherwise, through the media and/or the intima layers 204, 206. For example, it has been found that attachment of certain ports solely to the adventitia layer 202 (i.e., without attachment to other tissues) can result in mobility of the ports relative to the media and intima layers 204, 206. The ports may shift longitudinally and/or laterally relative to the inner layers 204, 206 of the vessel 200 from such activities as palpation of the ports during cannulation procedures or various day-to-day occurrences. Such mobility of a vascular access port can potentially result in the creation of multiple puncture sites in the vessel 200 over the course of repeated cannulations, which can weaken the vessel wall over time and potentially result in an aneurysm, vessel stenosis, hematoma, and/or bleeding.

FIGS. 9A-9E depict various stages of an illustrative method for implanting a vascular access port 100 in a patient 210 such that the vascular access port 100 provides direct access to a vessel within the patient 210. The term "patient" is used broadly herein and includes any animal subject who can or does undergo some process or procedure, whether provided by another or self-administered, and the term is not limited to an individual within a healthcare facility. The vascular access port 100 may be used with any suitable vessel, such as an artery 212, a vein 214 (both shown in FIG. 9A), or an artificial graft (see FIG. 14B). As previously discussed, the vessel may be at any of a variety of positions within the patient 210, such as the neck, the upper arm, the forearm, or the leg, and it may be located at a relatively deep or shallow position relative to the skin 216 of the patient. Numerous uses of an implanted port 100 are possible, including, for example, hemodialysis, chemotherapy, antibiotic therapy, total parenteral nutrition, pain management, aquapheresis, plasmapheresis, hydration, or long-term therapies of any suitable variety. In the illustrated method, a vascular access port 100 is shown being implanted in a forearm of the patient 210—specifically, the vascular access port 100 is shown being connected to a vein 214 that is associated with an arteriovenous fistula 218 for use in hemodialysis. It is noted that the vein 214 is a three-layered vessel such as the vessel 200 depicted in FIG. 8, and thus may be referred to hereafter as a vessel 200 to illustrate the more general applicability of the procedures discussed.

Figure 9A:
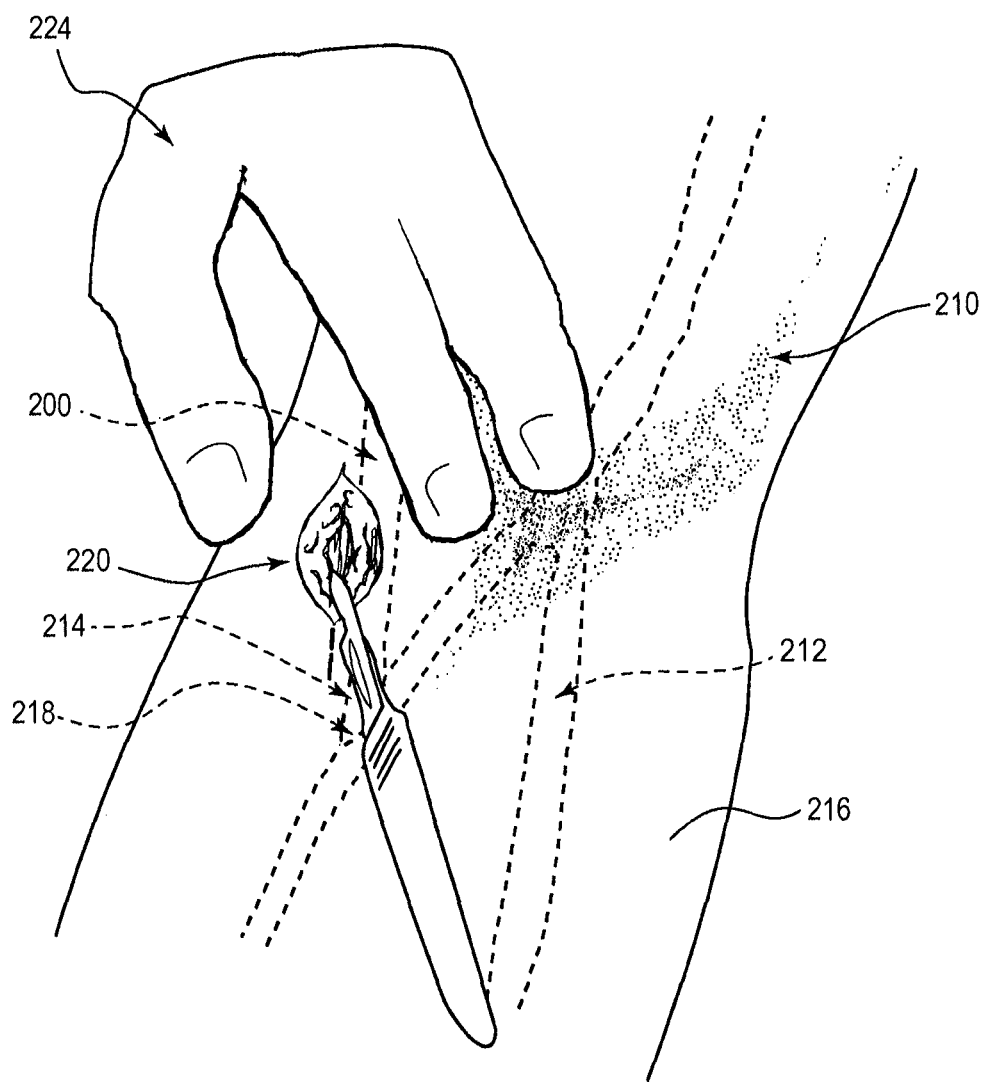
FIG. 9A is a perspective view of a stage of an illustrative method of implanting an embodiment of a vascular access port in a patient depicting the creation of an incision.

With reference to FIG. 9A, an incision 220 can be made in the skin 216 of the patient 210. In the illustrated embodiment, the incision 220 can be from about 4 centimeters to about 5 centimeters in length. The incision 220 can extend substantially parallel to the vessel 200, but can be offset relative thereto (i.e., is not directly over the vessel 200). In the illustrated embodiment, the incision 220 is offset from a position directly over the vessel 200 by a distance of from about 2 centimeters to about 3 centimeters. As discussed further with respect to FIG. 9E, such an orientation of the incision 220 can facilitate access to the vascular access port 100 after the implantation procedure is complete. In other methods, the incision 220 can be directly over the vessel 200 and/or at an angle or entirely transverse relative thereto. The incision 220 can be made by a practitioner 224 using any suitable techniques and instruments.

Figure 9B:
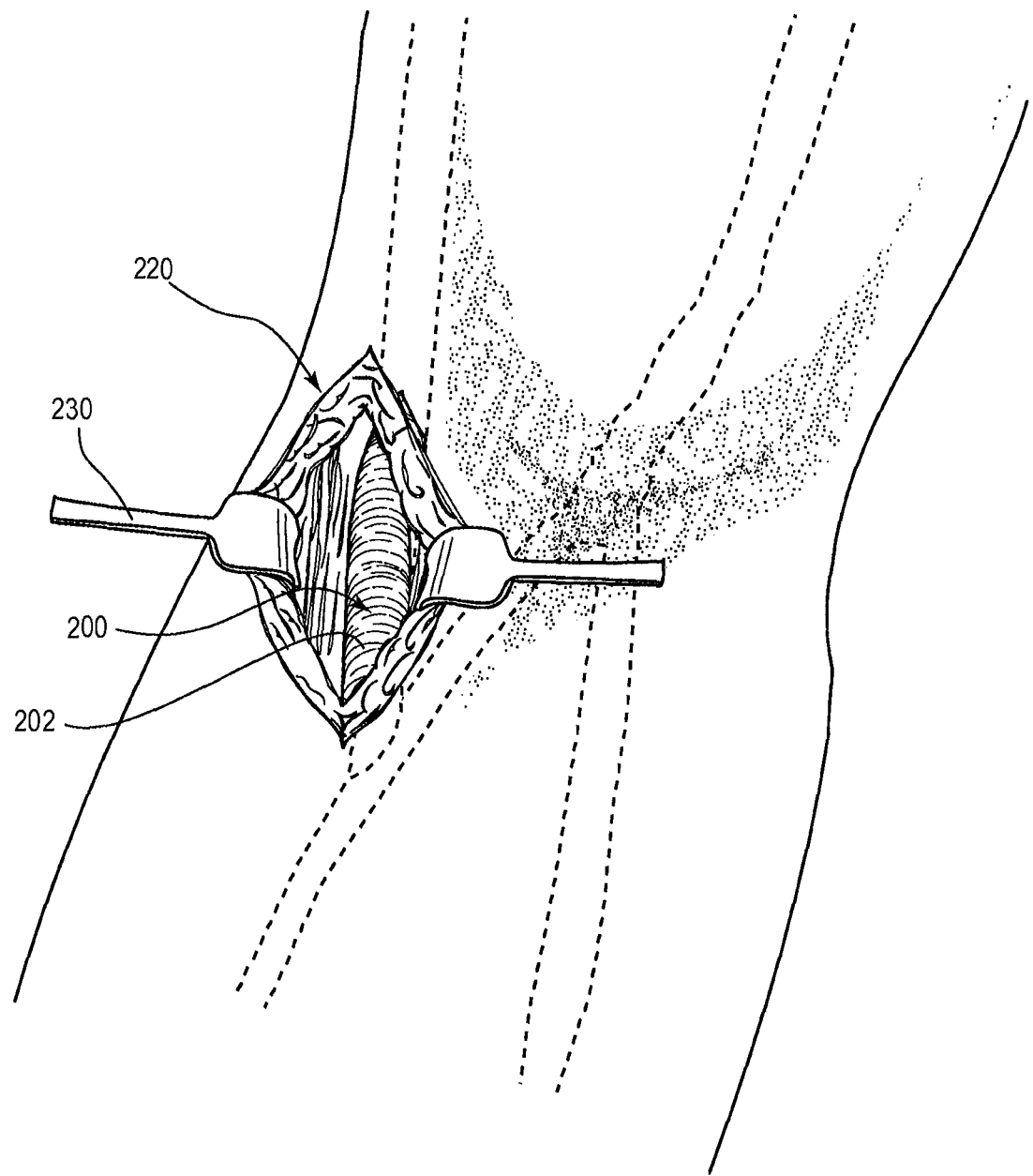
FIG. 9B is a perspective view of another stage of the method of FIG. 9A in which a vessel is exposed.
Figure 9C:
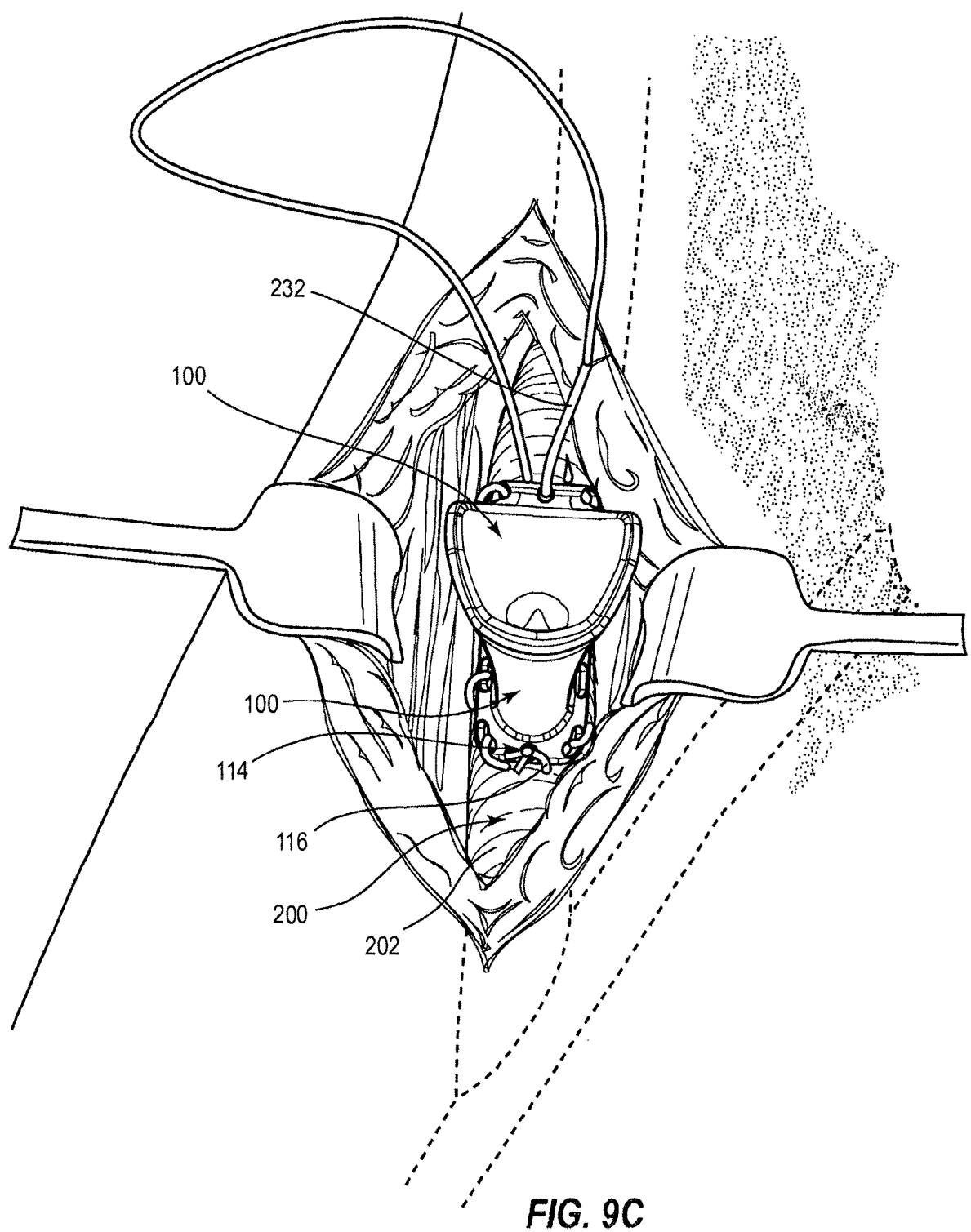
FIG. 9C is a perspective view of another stage of the method of FIG. 9A in which an attachment is made between the vascular access port and the vessel.

With reference to FIG. 9B, the vessel 200 can be exposed by removing, partially removing, or separating skin, fat, and fascial layers from the adventitia layer 202 of the vessel 200 at the site of the incision 220. Exposure of the vessel 200 can be maintained in any suitable manner, such as by the use of tissue spreaders 230. With reference to FIG. 9C, an initial attachment of the vascular access port 100 to the vessel 200 can be achieved at the front end or the back end of the vascular access port 100. In some procedures, an attachment device 116 can be inserted through all three layers 202, 204, 206 (see FIG. 8) of the vessel 200 and through an attachment passage 114 at each of the front and back ends of the vascular access port 100 along a lateral center of the port 100 prior to use of any of the remaining attachment passages 114. Initial attachment of the front end and/or the back end of the vascular access port 100 can assist in ensuring that a desired orientation of the vascular access port 100 is achieved and maintained during the course of the implantation procedure.

As previously mentioned, any suitable attachment device (or devices) 116 may be used in securing the vascular access port 100 to the vessel 200. The attachment devices 116 can include, for example, one or more sutures, pinch rings, hooks, or wires. Once an attachment device 116 is in a desired position, it can be securely tied, crimped, twisted, or otherwise fastened.

In the illustrated embodiment, the attachment device 116 comprises a running suture, which can be looped through multiple attachment passages 114. In the illustrated embodiment, a single running suture 116 is used to secure the vascular access port 100 to the vessel 200. In other embodiments, the suture 116 may extend through fewer passages 114 and one or more additional sutures 116 may be used. For example, as previously discussed, in some embodiments, a separate suture 116 is secured at each end of the vascular access port 100 prior to providing sutures in any of the remaining attachment passages 114.

Various options are available for securing one or more sutures 116 in place. For example, in some procedures, a suture needle 232 can be inserted through the wall of the vessel 200 at a position near an attachment passage 114, and can then pass through the attachment passage 114 after having passed through the vessel wall. A suture 116 associated with the suture needle 232 can then be tied using a surgical knot and the excess suture trimmed. In other procedures, a suture 116 can be positioned at a desired location within the wall of the vessel 200 such that at least one leg thereof protrudes from the adventitia layer 202. The protruding leg of the suture 116 can be received through a desired attachment passage 114 of the vascular access port 100 as the port 100 is brought into contact with the vessel 200. The suture 116 can then be tied and trimmed. Either approach may be used to secure sutures 116 through any desired number of attachment passages 114 of the vascular access port 100. Any other suitable suturing or attachment technique may be used. In some embodiments, only a portion of the available attachment passages 114 are used.

Figure 9D:
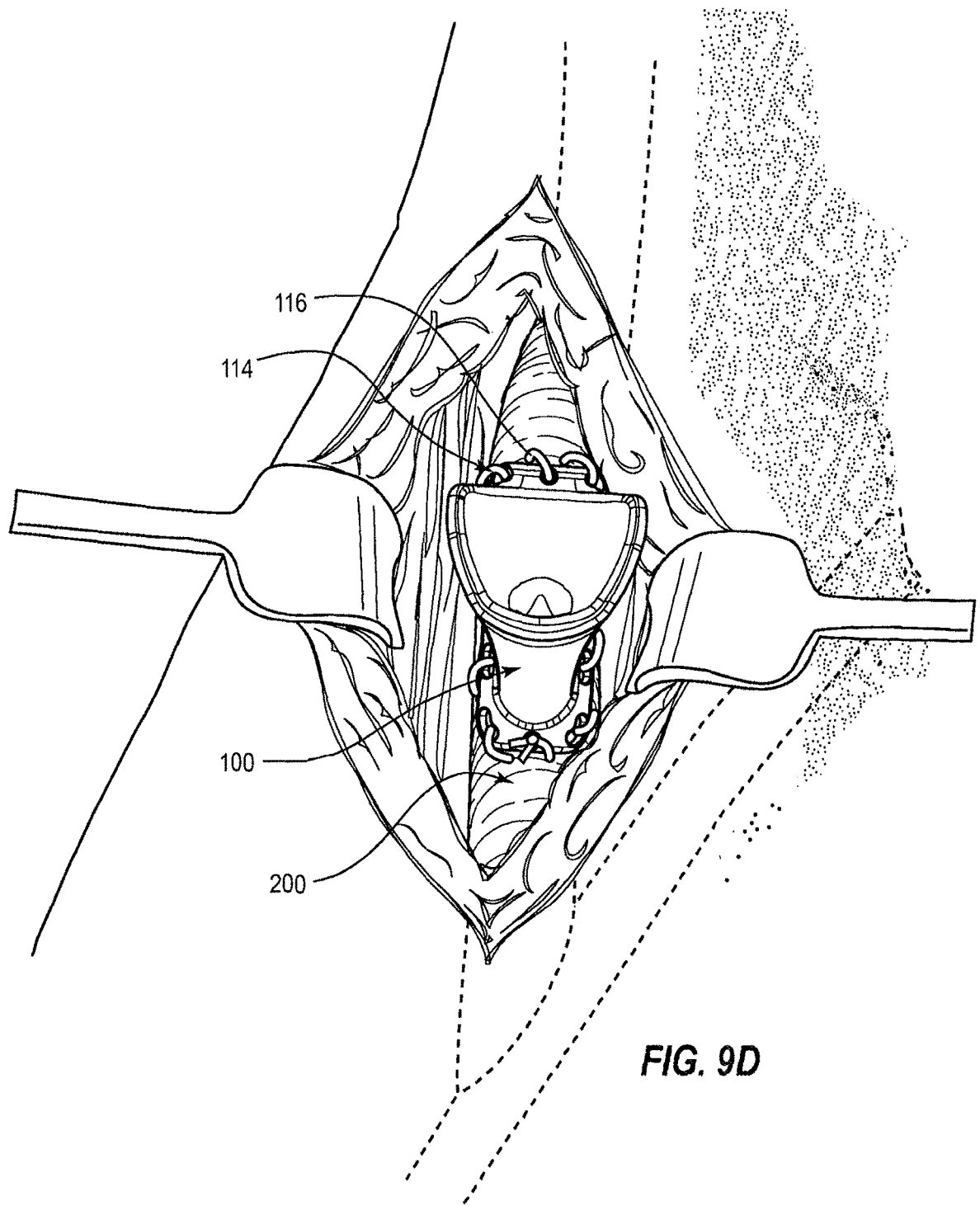
FIG. 9D is a perspective view of another stage of the method of FIG. 9A in which additional attachments have been made between the vascular access port and the vessel.

With reference to FIG. 9D, additional sutures 116 can be used to secure the vascular access port 100 to the vessel 200 via any or all of the remaining attachment passages 114, as desired. In some embodiments, the attachment passages 114 are filled, such as with silicone, so as to prevent ingrowth of tissue. In other embodiments, the attachment passages 114 are left open, which can permit ingrowth of tissue therein or therethrough.

Figure 9E:
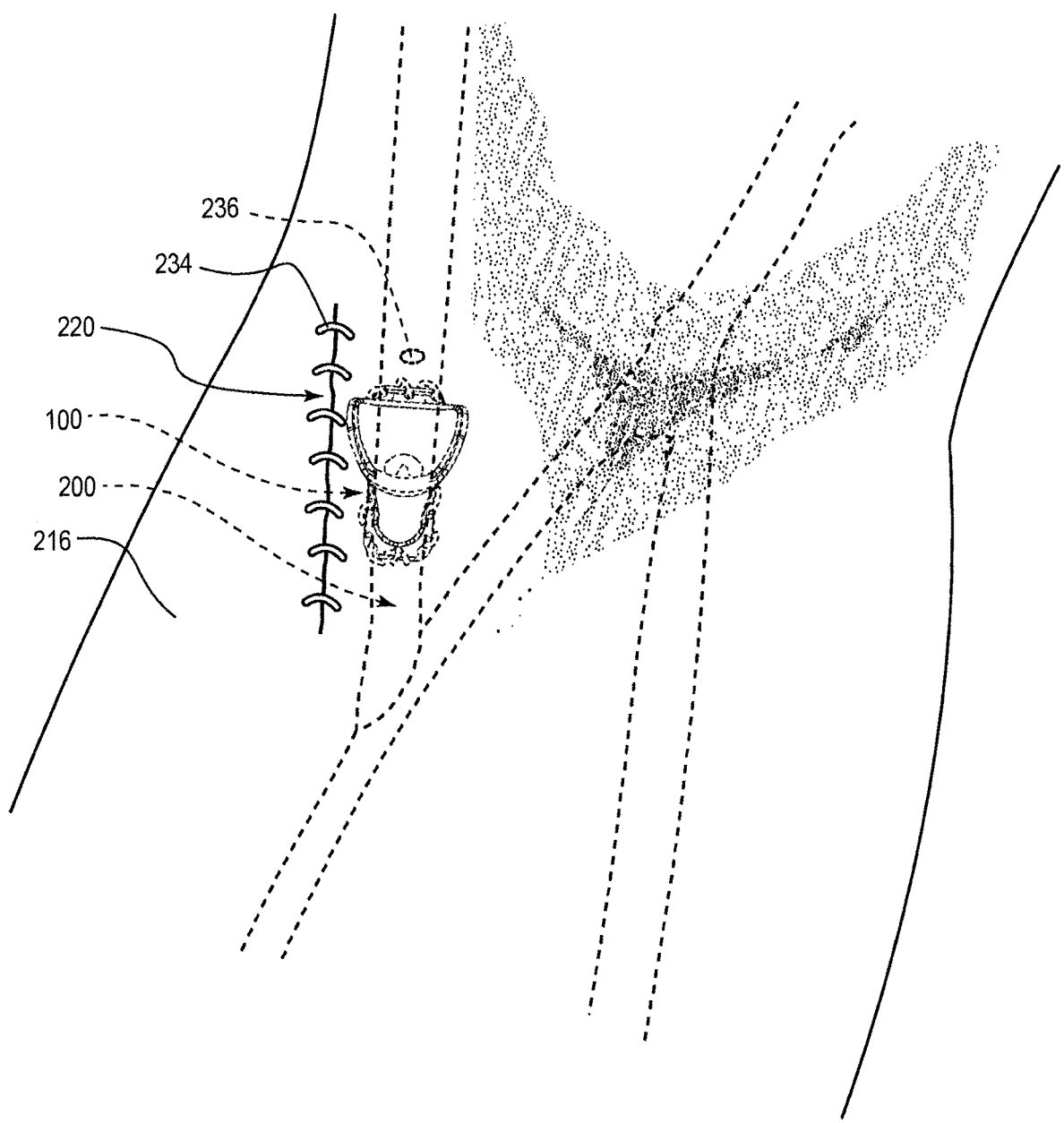
FIG. 9E is a perspective view of another stage of the method of FIG. 9A in which the incision has been closed.

With reference FIG. 9E, the site of the incision 220 can be closed in any suitable manner, such as, for example, via one or more sutures 234. As previously mentioned, the incision 220 can be offset from a position that is directly above the vascular access port 100. In such arrangements, an access device 144 can be inserted through the skin 216 to the vascular access port 100 via a surface insertion site 236 with little or no interaction with the site of the incision 220, or stated otherwise, without contacting any or much scar tissue at or beneath the surface of the skin 216. In certain cases, this may assist in the creation of an insertion tract that extends from the surface insertion site 236 to the vascular access port 100, as discussed further below.

In certain embodiments, it can be desirable to wait for a period of days or weeks after implantation of the vascular access port 100 before accessing the vessel 200 thereby. The waiting period can provide sufficient time for tissue ingrowth at the appropriate areas of the vascular access port 100, which can provide a more secure connection between the vascular access port 100 and the vessel 200.

FIGS. 10A-10G depict various stages of another illustrative method for implanting a vascular access port 100 in the patient 210 such that the vascular access port 100 provides direct access to the vessel 200 within the patient 210. Although the methods shown in FIGS. 9A-9E and 10A-10G are depicted relative to the same site within the patient 210, it is to be understood that the methods also may be used at other sites.

Figure 10A:
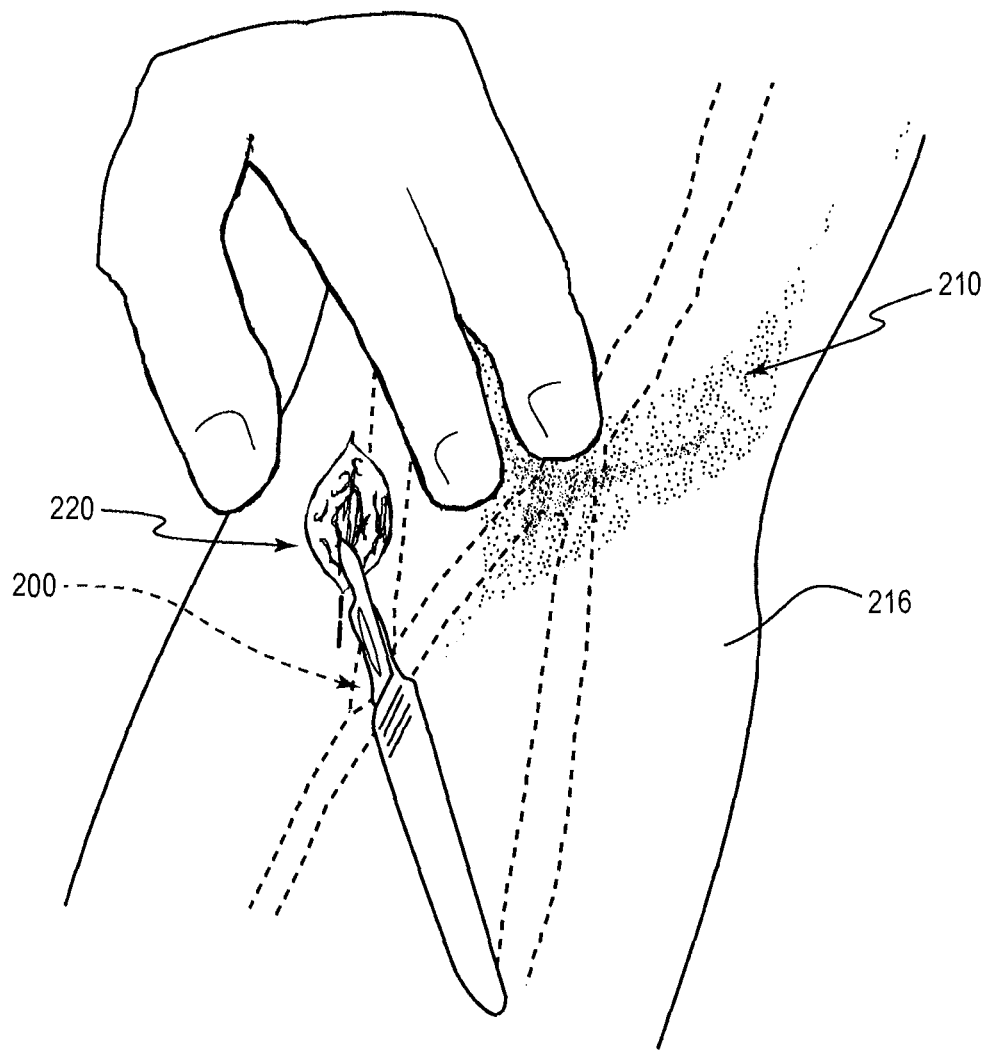
FIG. 10A is a perspective view of a stage of another illustrative method of implanting an embodiment of a vascular access port depicting the creation of an incision in the skin of a patient.

With reference to FIG. 10A, an incision 220 can be made in the skin 216 of the patient 210, which in some embodiments can be from about 4 centimeters to about 5 centimeters in length. The incision 220 can extend substantially parallel to vessel 200 and can be offset relative thereto. In some embodiments, the offset can be by a distance of from about 2 centimeters to about 3 centimeters.

Figure 10B:
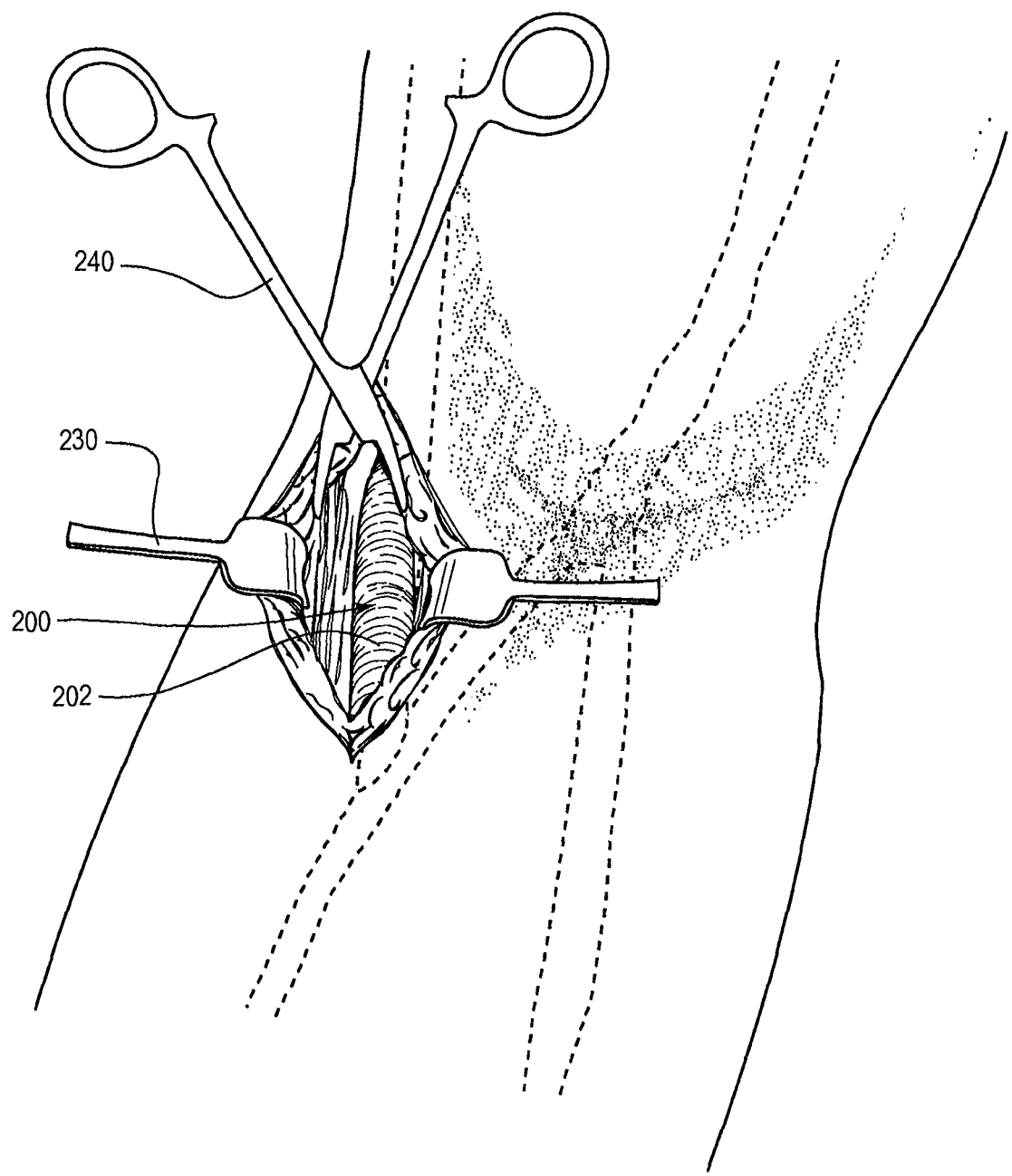
FIG. 10B is a perspective view of another stage of the method of FIG. 10A in which adventitia of a vessel is isolated.

With reference to FIG. 10B, the vessel 200 can be exposed by removing, partially removing, or separating skin, fat, and fascial layers from the adventitia layer 202 of the vessel 200 at the site of the incision 220. In some cases, a hemostat 240 can assist in this process. Exposure of the vessel 200 can be maintained in any suitable manner, such as by the use of tissue spreaders 230.

Figure 10C:
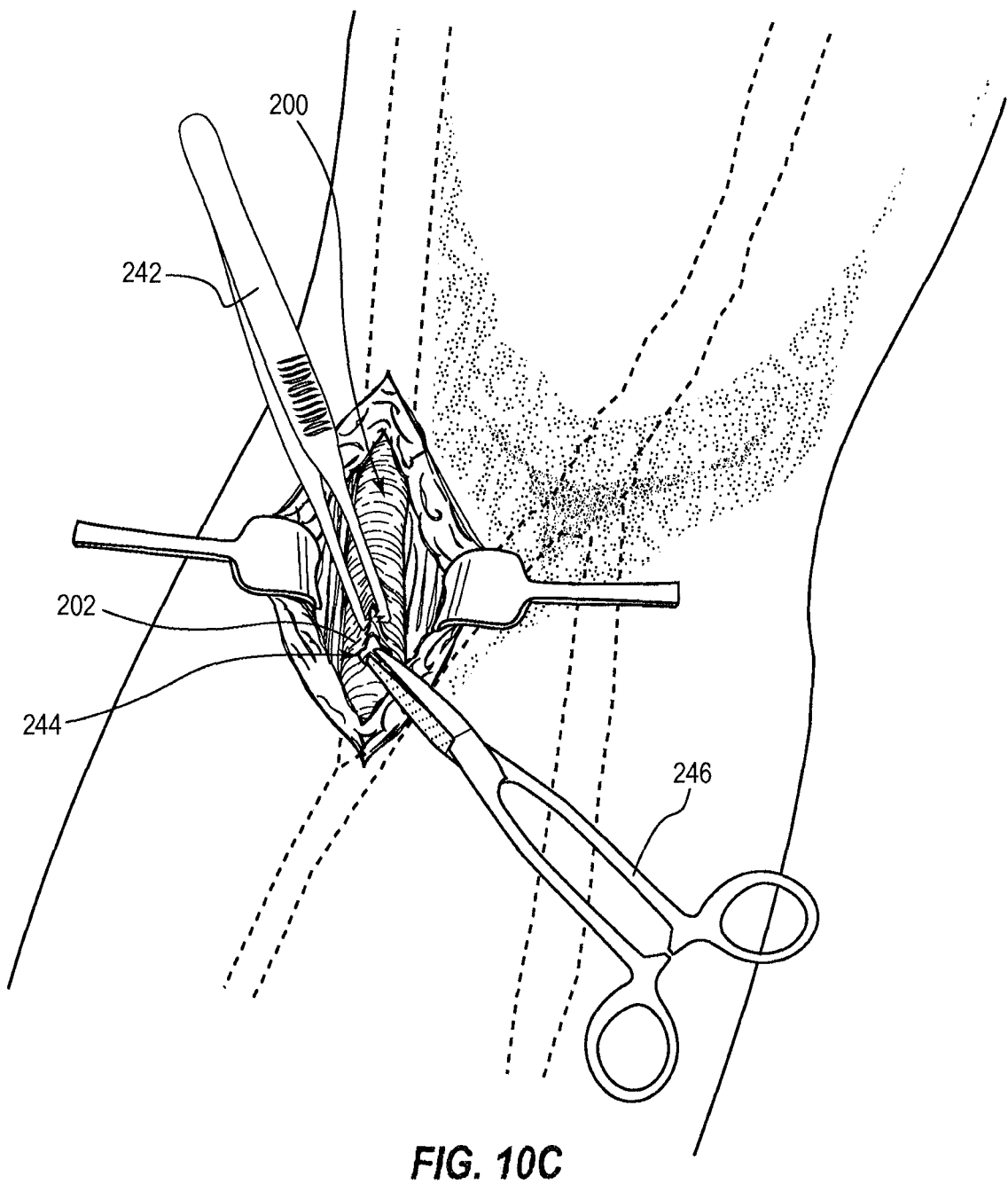
FIG. 10C is a perspective view of another stage of the method of FIG. 10A in which in incision is made in the adventitia.

With reference to FIG. 10C, a portion of the adventitia 202 can be isolated or separated from other portions of the vessel 200 in any suitable manner, such as via one or more forceps 242. Each set of forceps 242 can be used to capture or gather up a portion of the adventitia 202 and/or fascia layers or fat that may not have been removed or spread apart by the tissue spreaders 230.

With reference to FIG. 10C, while the portion of adventitia 202 is being held in its separated state, a small incision 244 can be made therein in any suitable manner, such as via a scalpel or via scissors 246.

Figure 10D:
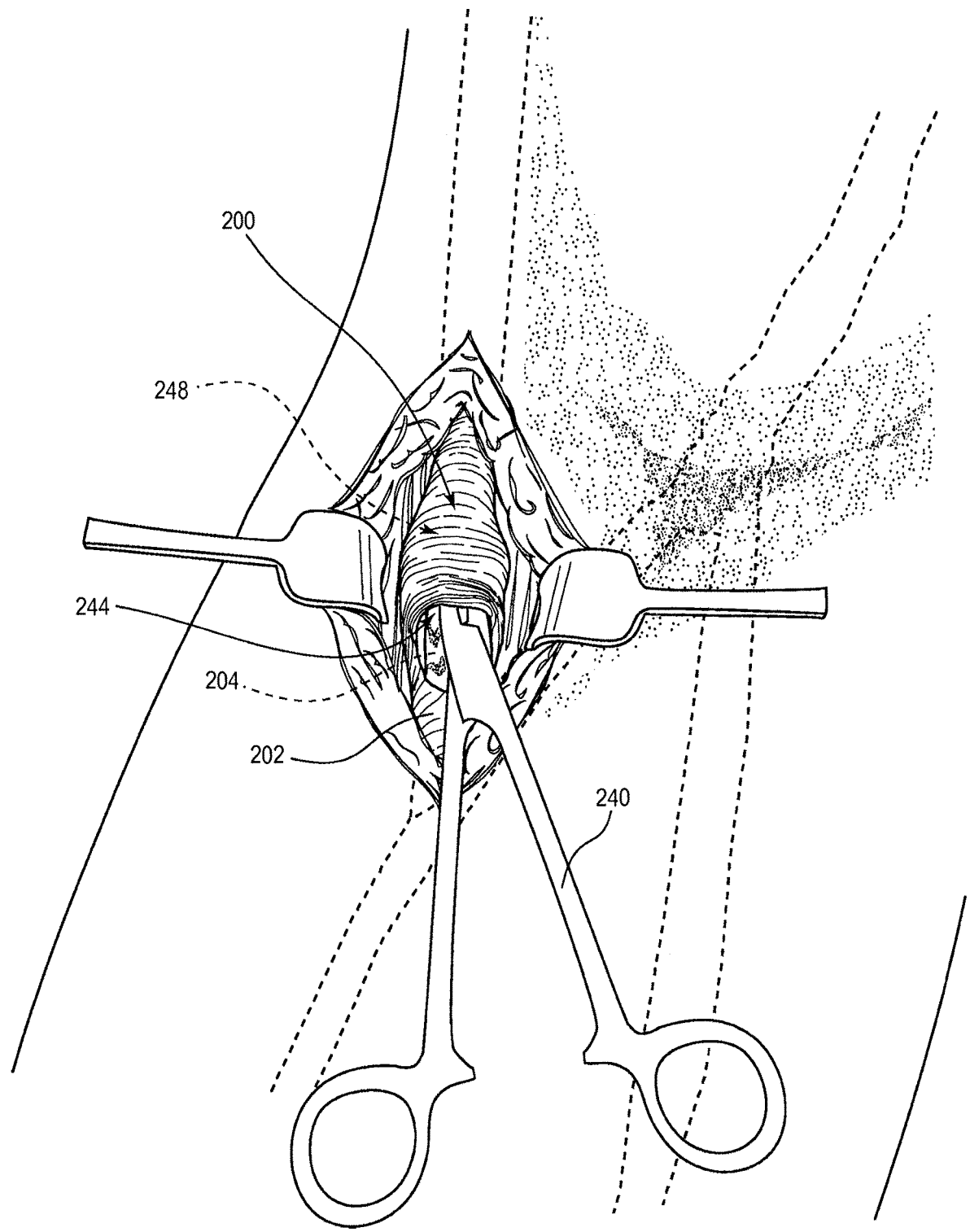
FIG. 10D is a perspective view of another stage of the method of FIG. 10A in which a pocket is formed in the adventitia.

With reference to FIG. 10D, a hemostat 240 can be inserted through the incision 244 so as to slide between the isolated adventitia 202 and the remaining layers of the vessel 200. In instances, it can be difficult to separate all of the adventitia 202 from the media layer 204 of the vessel 200. This, in the illustrated embodiment, the media layer 204 is shown, but is obscured by a thin layer of adventitia 202. The hemostat 240 can be used to bluntly dilate a pocket 248 within the adventitia 202 layer. Although not depicted, in some cases, the forceps 242 may be used to maintain control of the adventitia 202 during formation of the pocket 248.

In certain embodiments, the pocket 248 can be sufficiently large to receive the vascular access port 100 therein, while in others, the pocket 248 can be slightly smaller than the vascular access port 100. In some embodiments, the pocket 248 can have a length of no more than about 2.0, 2.5, 3.0, or 3.5 centimeters, and can have a width of no more than about 70, 80, or 90 percent of a width of the outer diameter of the media layer 204.

Figure 10E:
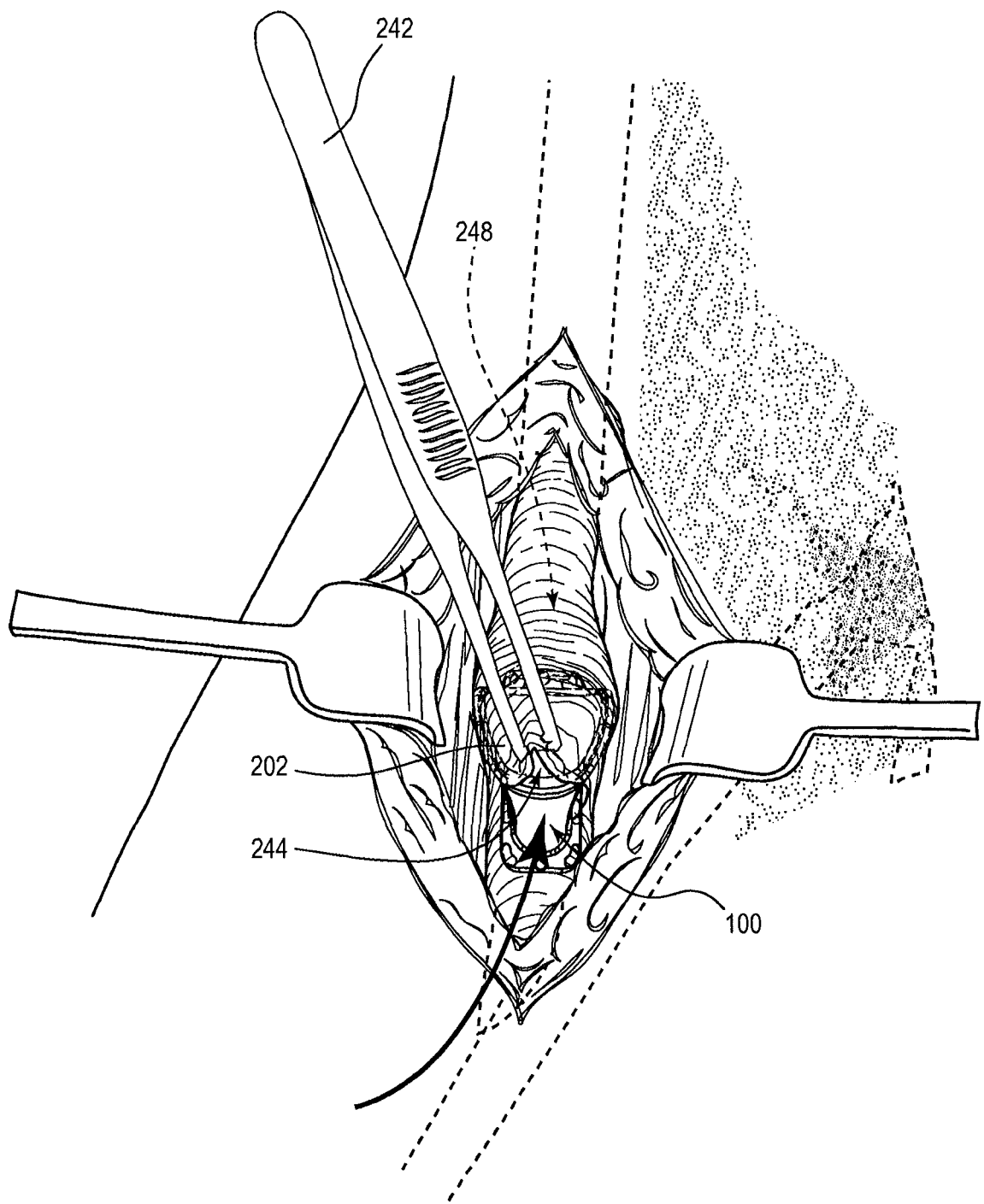
FIG. 10E is a perspective view of another stage of the method of FIG. 10A in which an embodiment of a vascular access port is inserted into the pocket.

With reference to FIG. 10E, the vascular access port 100 can be inserted through the incision 244 into the pocket 248. In some cases, the forceps 242 or other clamping devices are used to maintain control of the adventitia 202 during insertion of the vascular access port 100. The vascular access port 100 can be introduced into the pocket 248 either rearward end first, as shown, or forward end first, and the port 100 can be pushed to the end of the pocket 248 opposite the incision 244.

Figure 10F:
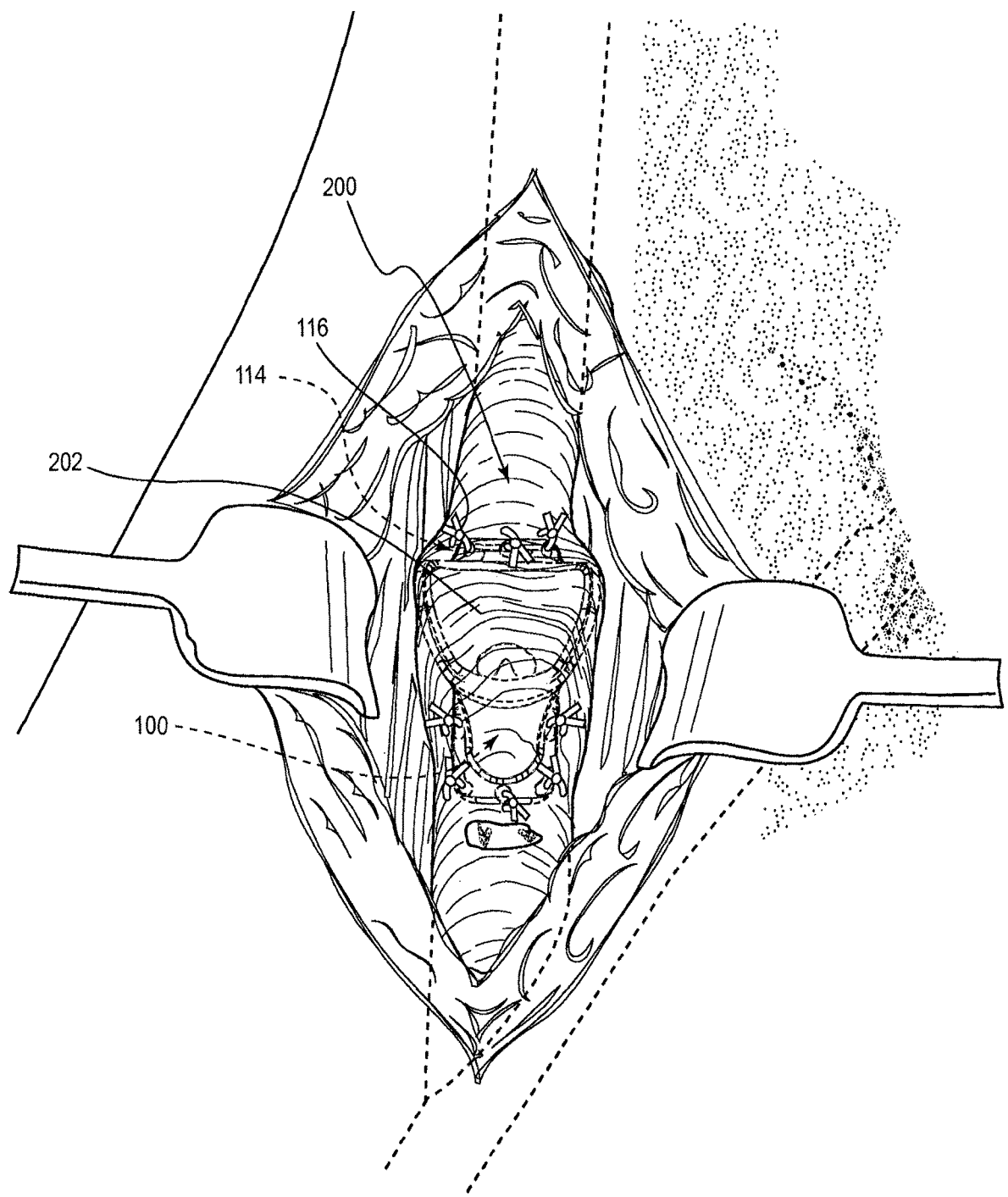
FIG. 10F is a perspective view of another stage of the method of FIG. 10A in which attachments have been made between the vascular access port and the vessel.

With reference to FIG. 10F, the adventitia 202 can cover all or substantially all of the implanted vascular access port 100 when it is within the pocket 248. Sutures 116 can be advanced through the adventitia 202, through the attachment passages 114, and through the remaining portion of the adventitia layer 202, as well as through the entirety of the media and intima layers 204, 206 to attach the vascular access port 100 to the vessel 200. Suture knots thus may be tied outside of the adventitia 202. In other embodiments, the sutures 116 do not pass through the separated portion of the adventitia 202 and may be tied prior to being covered by the adventitia 202.

Figure 10G:
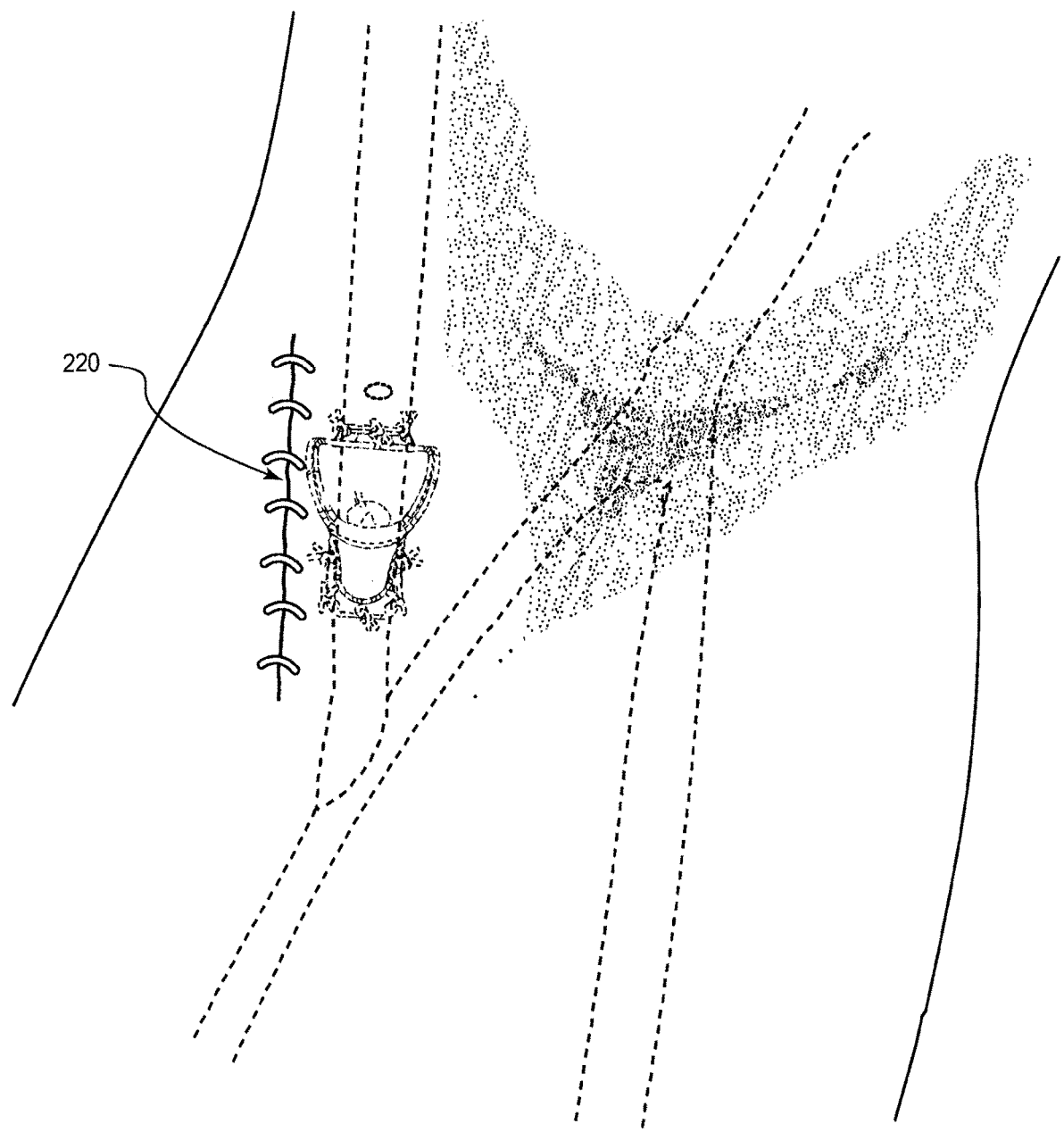
FIG. 10G is a perspective view of another stage of the method of FIG. 10A in which the incision in the skin of the patient has been closed.

FIG. 10G depicts the site of the incision 220 in a closed configuration. The incision 220 can be closed in any suitable manner, such as in any of the manners described above with respect to FIG. 9E.

With reference again to FIGS. 10C-10F, in other methods, at least a portion of the adventitia 202 can be removed rather than forming the pocket 248 therein. The vascular access port 100 may be placed atop a thin layer of the adventitia 202 at a site from which the at least a portion of adventitia 202 has been removed, and sutures 116 may be directly inserted through the attachment passages 114 and through the thinned adventitia layer 202, the media layer 204, and the intima layer 206. The vascular access port 100 may, at least initially, be less stable relative to the vessel 200 when it is implanted in this manner, rather than when it is inserted into the pocket 248.

FIGS. 11A-11E depict various procedures that may be performed relative to an implanted vascular access port 100. As will be discussed, the vascular access port 100 can facilitate the creation of a buttonhole. The vascular access port 100 likewise can facilitate use of the buttonhole once it is formed. These and/or other advantages of the vascular access port 100 will be apparent from the disclosure that follows.

Additionally, as previously mentioned, tissue may grow into or attach to various areas of the vascular access port 100. For example, vessel tissue may grow into the ingrowth-inducing covering 152. In some embodiments, skin tissue may grow into at least a portion of the guidance passageway 130, although such ingrowth is not shown in FIGS. 11A-11E.

Figure 11A:
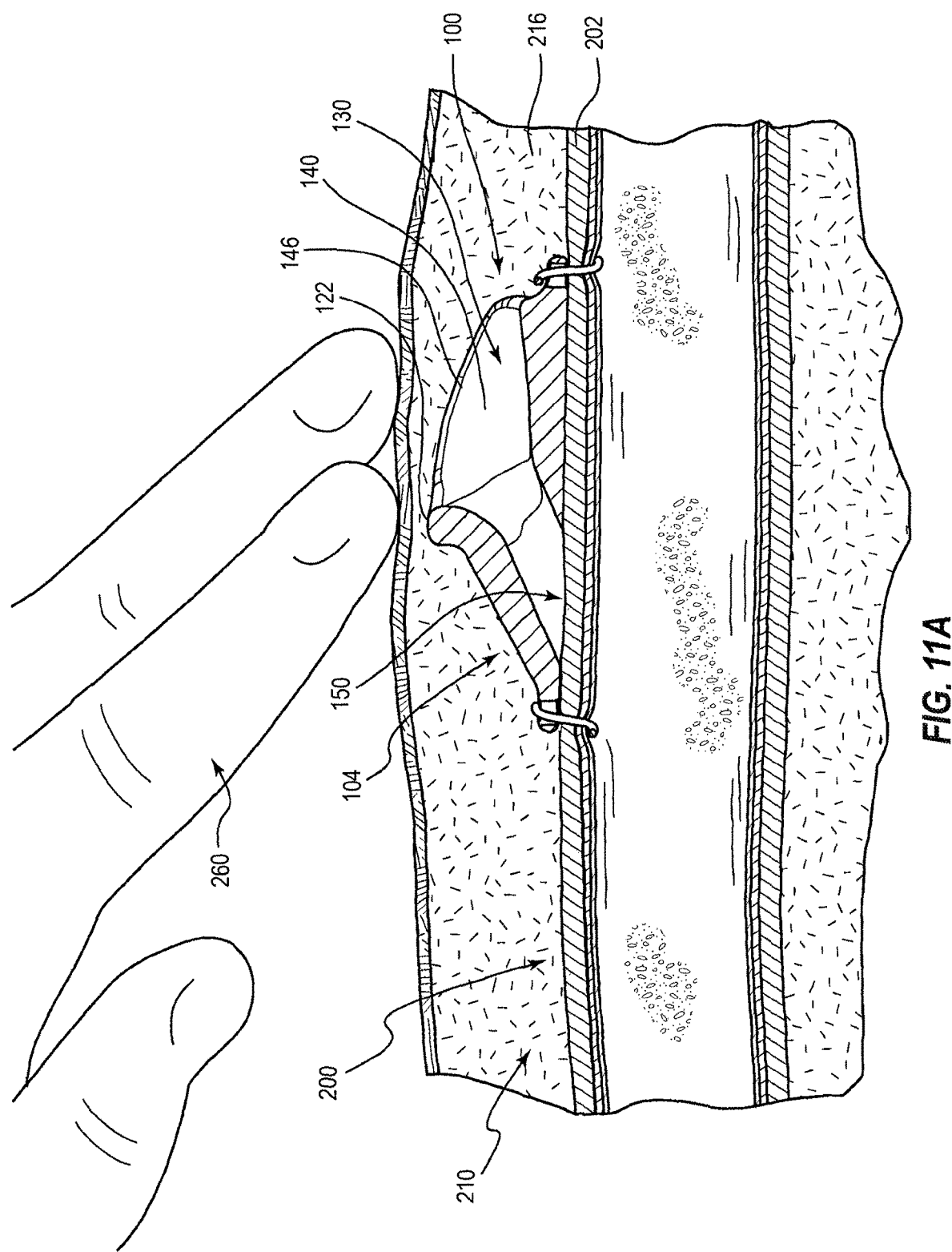
FIG. 11A is a cross-sectional view of a palpations stage of an illustrative method relating to the creation and use of a buttonhole access site to access a lumen of a vessel.

FIG. 11A depicts an embodiment of the vascular access port 100 that has been implanted in the patient 210 in any suitable manner, such as via the method depicted in FIGS. 9A-9E. The opening 150 of the guidance passageway 130 is at or adjacent to the vessel 200. Specifically, in the illustrated embodiment, the opening 150 is at the adventitia layer 202 of the vessel 200.

In the stage that is shown, a clinician 260 palpates the skin 216 to locate and determine the orientation of the vascular access port 100. The term "clinician" is used broadly herein and includes any individual who conducts a process or procedure relative to an implanted access port 100, whether that individual is the individual in whom the access port 100 is implanted (e.g., a patient) or someone else, and the term is not limited to an individual within a healthcare facility. In the illustrated embodiment, the clinician 260 is using fingers to contact the skin 216 located above the pinnacle region 122 of the palpation projection 146. In other instances, the clinician 260 can palpate any other suitable portion of the body 104 to determine the location (e.g., depth) and orientation of the port 100. For example, the clinician 260 may use one or more fingers and/or a thumb to contact the skin 216 that is over or beside other portions of the palpation projection 146, or to squeeze the skin 216 that is at either side of the wings 140. In still other or further embodiments, a clinician may visually determine a location and orientation of the port 100. Prior or subsequent to the stage shown in FIG. 11A, the clinician 260 can clean a surface of the skin with any suitable antiseptic so as to reduce the risk of introducing pathogens into the bloodstream of the patient.

Figure 11B:
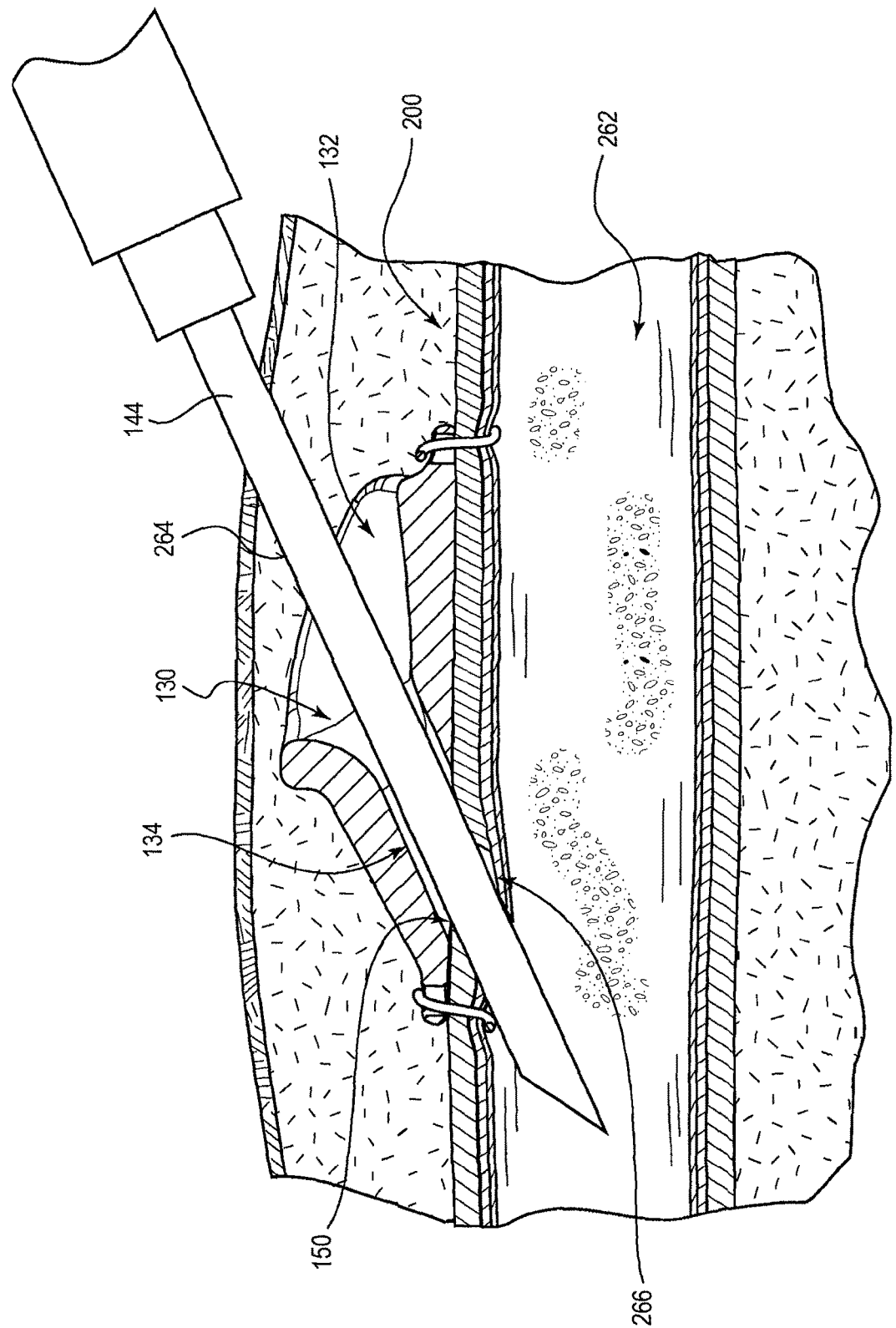
FIG. 11B is a cross-sectional view of another stage of the method of FIG. 11A in which a needle having a sharp tip is inserted into the lumen of the vessel via an embodiment of a vascular access port.

FIG. 11B illustrates an embodiment of an access device 144 directly accessing a lumen 262 of the vessel 200 via the vascular access port 100 for a first time. Although the fingers of the clinician 260 are not shown in FIG. 11B, the clinician 260 may continue to palpate the vascular access port 100 while inserting the access device 144 into the skin and the vascular access port 100. This can aid in achieving a desired alignment of the access device 144 with the guidance channel 130. The clinician 260 also may make minor adjustments to an orientation of the vascular access port 100 by applying pressure thereto.

The access device 144 can comprise any suitable device configured for fluid communication between a position outside of the skin 216 and the vessel lumen 262 when the device has been introduced into the lumen 262 via the vascular access port 100. For example, in various embodiments, the access device 144 can comprise a needle or a catheter. In many embodiments, the access device 144 can be relatively rigid so as to be able to readily pass through the skin 216. Accordingly, in some embodiments, the catheter may be an over-the-needle catheter.

Standard needles that are presently used in hemodialysis or other procedures may be used with embodiments of the vascular access port 100, which may facilitate use of such ports. For example, standard protocols for making and using buttonholes in vessels via known freehand methods may be readily adapted to "device-assisted" buttonhole techniques that employ the vascular access ports 100, and this can take place without alteration to the instruments called for by the existing protocols.

As the procedural stage depicted in FIG. 11B represents an initial access of the vessel lumen 262, the access device 144 is shown as having a sharp tip, which can allow the access device 144 to more readily be inserted through the unbroken skin so as to form an insertion tract 264, and also through an insertion site 266 of the vessel 200. As further discussed below, however, other embodiments of an access device 144 that have blunt ends may be used after one or more access events with a sharp-ended access device 144 have occurred. For example, as discussed hereafter, a sharp access device 144 can be used for a given number of access events until a sufficiently defined insertion tract 264 has been formed through the skin of a patient, and a blunt access device 144 can be used thereafter. For example, a sharp access device 144 can be used for 1, 2, 3, 4, 5, 6, 7, 8, 9, or 10 access events; at least 1, 2, 3, 4, 5, 6, 7, 8, 9, or 10 access events; no more than 2, 3, 4, 5, 6, 7, 9, or 10 access events; or within a range of from 1 to 10, from 2 to 9, from 3 to 8, or from 4 to 7 access events prior to the use of a blunt access device 144. Use of the vascular access port 100 can allow for a small number of initial access events with a sharp-ended access device 144 before a blunt-ended access device 144 may be used, which may result from an ability of the vascular access port 100 to consistently and repeatedly direct an access device 144 to the same insertion site in a vessel.

In certain embodiments, the access device 144 can comprise a needle sized from 14 gauge to 20 gauge. As previously mentioned, the diameter and length of the channel 134 can be configured to direct the access device 144 to a specific region of the vessel 200. This may be achieved by a relatively close fit between the channel 134 of the vascular access port 100, which can provide for a predictable orientation at which the access device 144 will exit the channel 134 through the opening 150. In some instances, it may be desirable for the channel 134 to be sized such that at least a small amount of space exists between an inner wall thereof and an access device 144 when the access device 144 is inserted therein. This can prevent or reduce binding of the access device 144 within the channel 134, which may be more likely to occur if tissue has grown into at least a portion of the channel 134. In some embodiments, a balancing or optimization may be achieved with respect to the spacing between the channel 134 and an access device 144 such that a sufficiently tight fit is achieved to allow the vascular access device 144 to be directed repeatedly to substantially the same area of the vessel 200 and to achieve hemostasis when the vascular access device 144 is inserted into the vessel 200 while inhibiting, reducing the occurrence of, or preventing binding of the vascular access device 144 within the channel 134. In various embodiments, an inner diameter of the channel 134 is larger than an outer diameter of an access device 144 with which it is configured to be used by an amount within a range of from about 0.25 gauge to about 3.0 gauge, from about 0.5 gauge to about 2.0 gauge, from about 0.75 gauge to about 1.5 gauge, or from about 0.75 gauge to about 1.25 gauge; by an amount that is no less than about 0.25, 0.5, 0.75, 1.0, 1.25, 1.5, 1.75, 2.0, 2.5, or 3.0 gauge; or by an amount that is no greater than about 0.25, 0.5, 0.75, 1.0, 1.25, 1.5, 1.75, 2.0, 2.5, or 3.0 gauge. In some embodiments, the channel 134 is about 1 gauge larger than access devices 144 with which it is configured to be used. For example, in the illustrated embodiment, the channel 134 may be sized at approximately 14 gauge and the access device 144 can comprise a 15 gauge fistula needle.

Other configurations for the channel 134 and the access device 144 are also possible. For example, one or more of the channel 134 and the access device 144 may have geometries other than cylindrical. In certain of such embodiments, the geometries of the channel 134 and of the access device 144 may be complementary to each other, whereas in other embodiments, a cross-sectional shape of the channel 134 may be different from a cross-sectional shape of the access device 144.

As previously mentioned, some protocols for the creation and use of buttonhole cannulation sites can require introduction of a needle into a vessel at a designated acute angle. In some embodiments, the angle α defined by the channel 134 (see FIG. 7) can be matched to this specified angle, and the channel 134 can constrain the access device 144 to enter the vessel 200 at the angle α, such that the vascular access port 100 can be configured for use with such protocols.

Figure 11C:
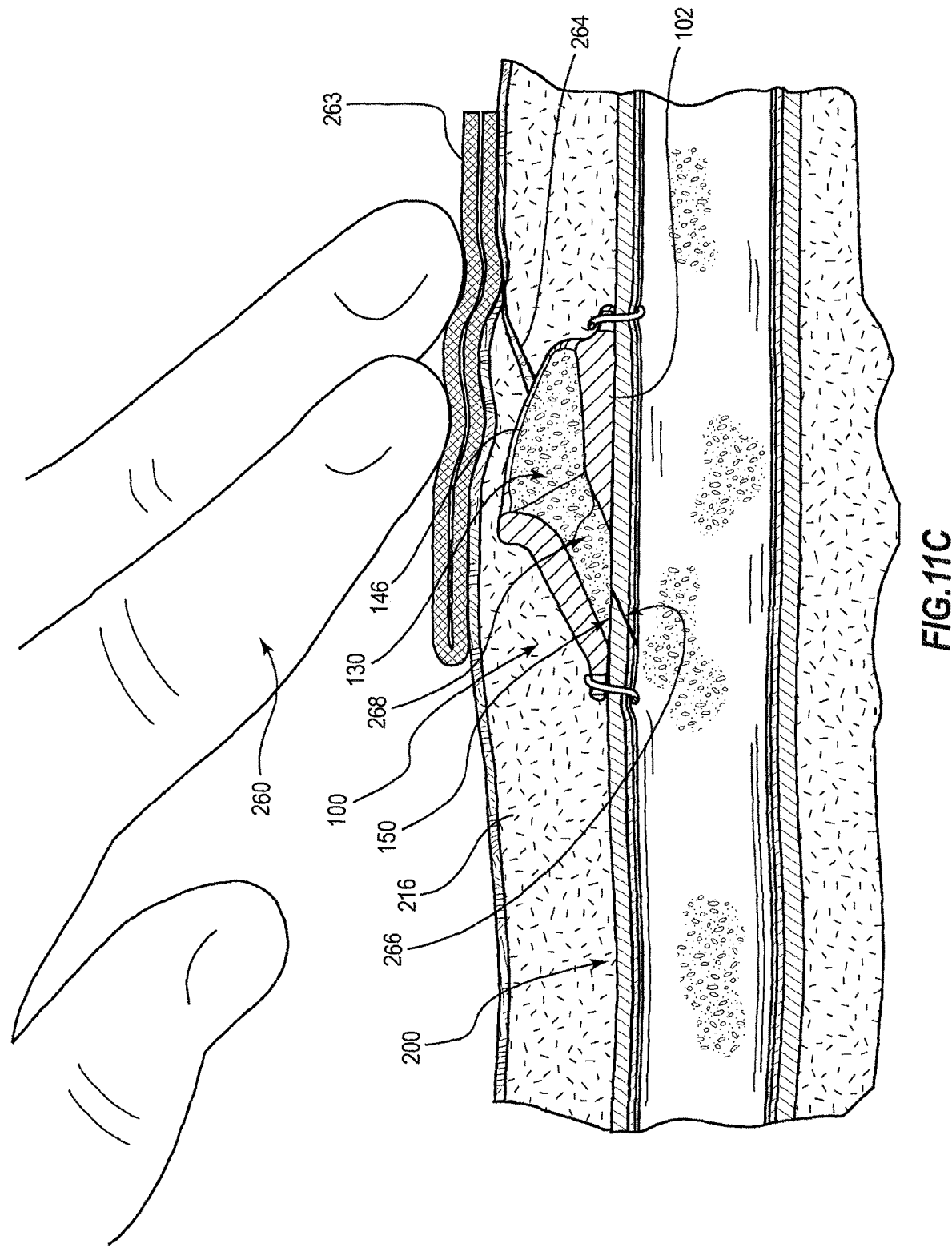
FIG. 11C is a cross-sectional view of another stage of the method of FIG. 11A in which pressure is applied to the skin of the patient.

FIG. 11C illustrates a stage of the procedure after removal of the access device 144. The insertion site 266 is shown in a closed state, in which it is allowed to heal. Prior to closure and healing of the insertion site 266, however, blood 268 can be permitted to exit thereby, and may fill the guidance passageway 130 and the insertion tract 264. The practitioner 260 can apply pressure above the vascular access port 100 to close the insertion tract 264 until bleeding subsides at the surface of the skin 216. For example, the practitioner 260 can apply pressure while simultaneously applying a pad 269 (e.g., gauze) to the upper end of the insertion tract 264. As previously mentioned, the entry mouth 136 of the guidance passageway 130 can be configured to assist in achieving hemostasis. For example, the entry mouth 136 may be relatively planar, and application of pressure above the entry mouth 136 can cause tissue surrounding the guidance passageway 130 to effectively seal the guidance passageway 130 about the entry mouth 136. In some embodiments, a two-finger technique may be used to close the insertion tract 264 while applying pressure to the tissue positioned above the guidance passageway 130. In some embodiments, pressure may be applied for a period of no more than about 5, 6, 7, 8, 9, or 10 minutes in order to achieve hemostasis.

A relatively tight attachment between the vascular access port 100 and the vessel 200, such as may be achieved by tissue ingrowth within the attachment area AR (see FIG. 5) likewise can assist in reaching hemostasis. For example, tissue ingrowth about the opening 150 can inhibit or prevent blood 268 from seeping outwardly between the base 102 of the vascular access port 100 and the vessel 200.

The procedures discussed with respect to FIGS. 11A-11C can be repeated multiple times. For example, with reference again to FIG. 11B, a second access device 144 having a sharp tip can be inserted through the insertion tract 264 toward the vascular access port 100 for a second insertion event. However, during the time between the first and second access events and/or as a result of palpation of the vascular access port 100 during the second access event, the vascular access port 100 and the vessel 200 to which it is attached may have shifted relative to the insertion tract 264 such that the channel 134 is no longer aligned with the insertion tract 264. As the access device 144 is advanced through the insertion tract 264, the tip of the access device 144 can contact the funnel region 132. The funnel region 132 then can direct the tip of the access device 144 into the channel 134 as the access device 144 is further advanced through the insertion tract 264. In some cases, this redirection of the tip of the access device 144 relative to the vascular access port 100 may urge the insertion tract 264 and the channel 134 into alignment with each other. Once the tip of the access device 144 enters the channel 134, the channel 134 directs the tip of the access device 144 to the insertion site 266 of the vessel 200. The vascular access port 100 thus can direct the access device 144 to the same insertion site 266 via which the vessel lumen 262 was accessed in the first access event.

Figure 11D:
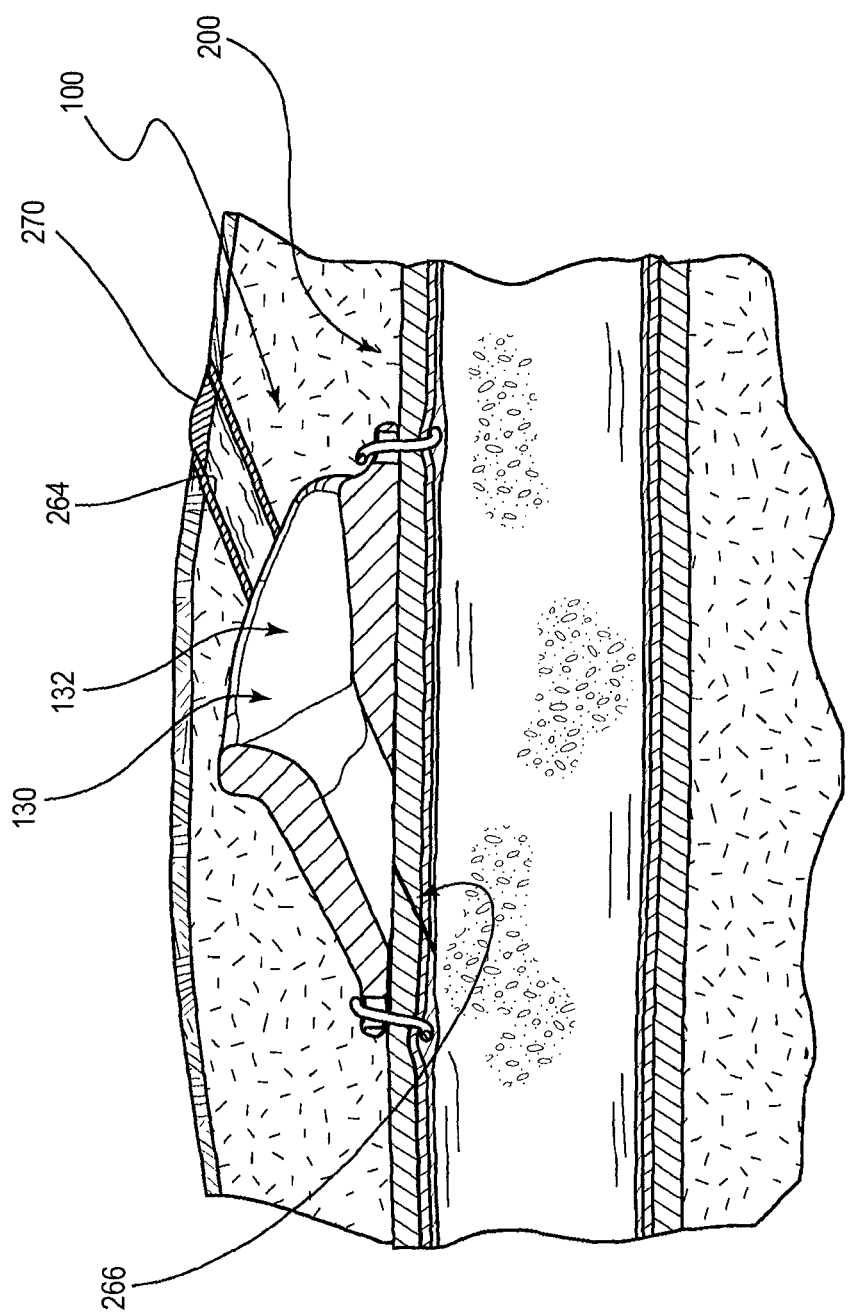
FIG. 11D is a cross-sectional view of another stage of the method of FIG. 11A in which an insertion tract and a buttonhole access site have been formed.

FIG. 11D depicts the insertion tract 264 and the insertion site 266 after multiple access events. As shown, the insertion tract 264 may become more well-defined over time, which may, for example, result from the formation of scar tissue or connective tissue. Similarly, the insertion site 266 may become more well-defined over time such that it may become easier to insert an access device 144 therethrough. Such an insertion site 266 through a vessel wall can be referred to as a buttonhole access site, or more commonly, as a buttonhole. Accordingly, the insertion site 266 may also be referred to herein as a buttonhole 266. In some embodiments, the well-defined insertion tract 264 and/or the buttonhole 266 may be established after 6, 7, 8, 9, or 10 access events.

In other embodiments, the insertion tract 264 and the buttonhole 266 can be formed by inserting an over-the-needle catheter (not shown) through the vascular access port 100. The needle portion can be removed and the catheter portion can be left in place until the insertion tract 264 is well-defined. The catheter then can be removed.

As previously discussed, in some instances, the vascular access port 100 may shift relative to the insertion tract 264 between access events. However, in certain embodiments, the funnel region 132 of the guidance passageway 130 is sufficiently large that a distal end of the insertion tract 264 opens into, or extends through at least a portion of, the funnel region 132 despite any such shifting. Accordingly, the vascular access port 100 may act as a mobile extension of the insertion tract 264, which is configured to ensure that access devices 144 are consistently aligned with and directed to the buttonhole 266, despite any relative movement between the insertion tract 264 and the vascular access port 100. In some instances, however, relatively little shifting may occur between the insertion tract 264 and the vascular access port 100, and an access device 144 may be inserted through the insertion tract 264 and directly into the channel 134 with little or no contact with the funnel region 132.

FIG. 11D also illustrates that a scab 270 may form over the insertion tract 264 between access events. The scab 270 may be removed prior to an access event. In other embodiments, a synthetic covering may be provided over or in place of the scab 270.

Figure 11E:
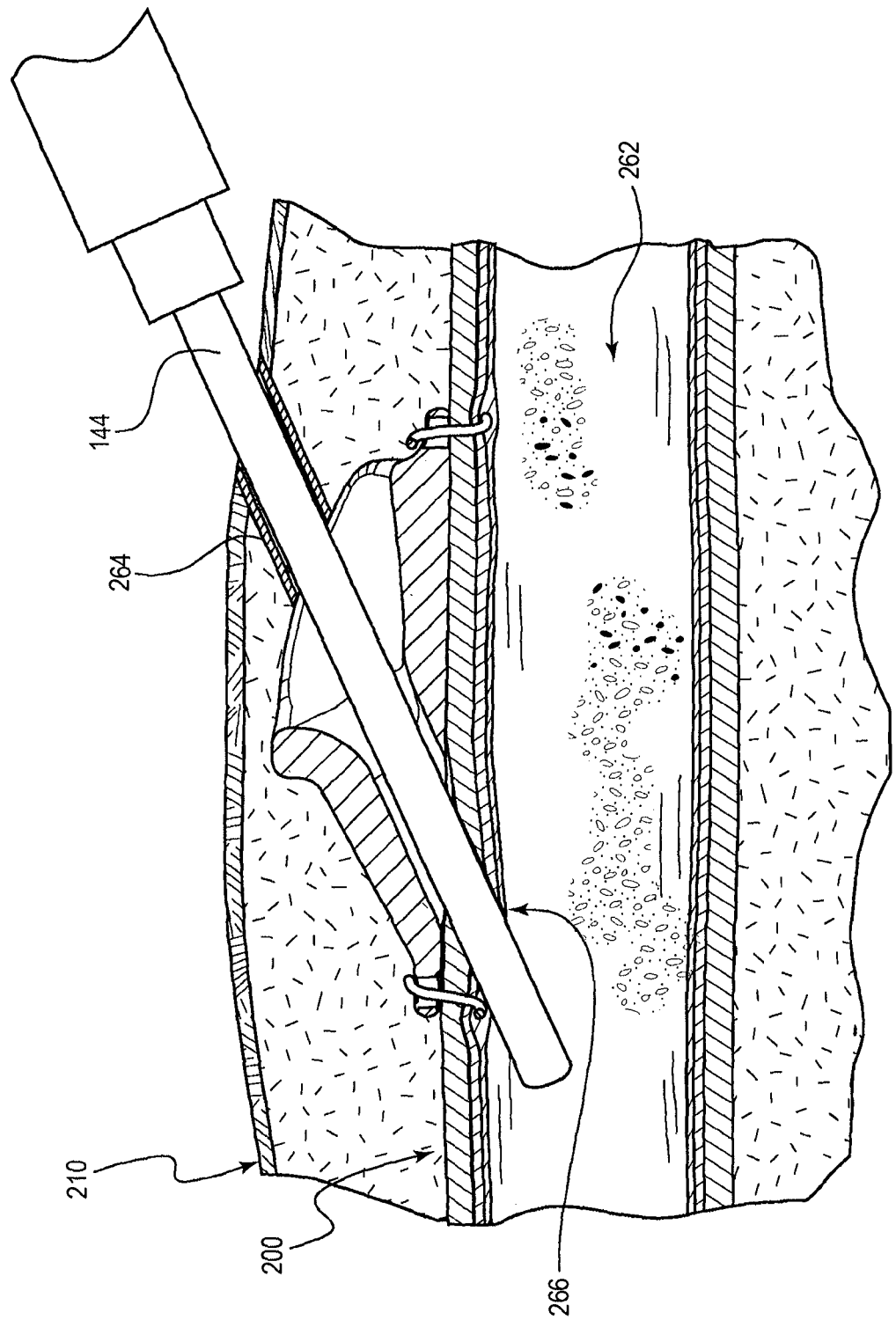
FIG. 11E is a cross-sectional view of another stage of the method of FIG. 11A in which a needle having a blunt tip is inserted into the lumen of the vessel via the insertion tract, the vascular access port, and the buttonhole access site.

FIG. 11E illustrates the use of an access device 144 having a blunt distal end after proper formation of the insertion tract 264 and the buttonhole 266. The blunt end of the access device 144 can guide the device 144 through the insertion tract 264 and through the buttonhole 266, and may do so in a less traumatic or more comfortable manner for the patient 210. Use of a blunt-tipped access device 144 also can reduce the risk of striking through an opposing side of the vessel 200.

As previously mentioned, in some embodiments, an over-the needle catheter can be used with an implanted vascular access port 100. In certain procedures, a needle/catheter assembly can be inserted through the insertion tract 264 into the vessel 200 (e.g., the jugular vein) and then the catheter can be advanced through the vessel to the desired position (e.g., the superior vena cava for certain central venous system applications). An infusion or other desired procedure can then be conducted. The catheter can be removed from the patient after completion of the procedure.

Figure 12:
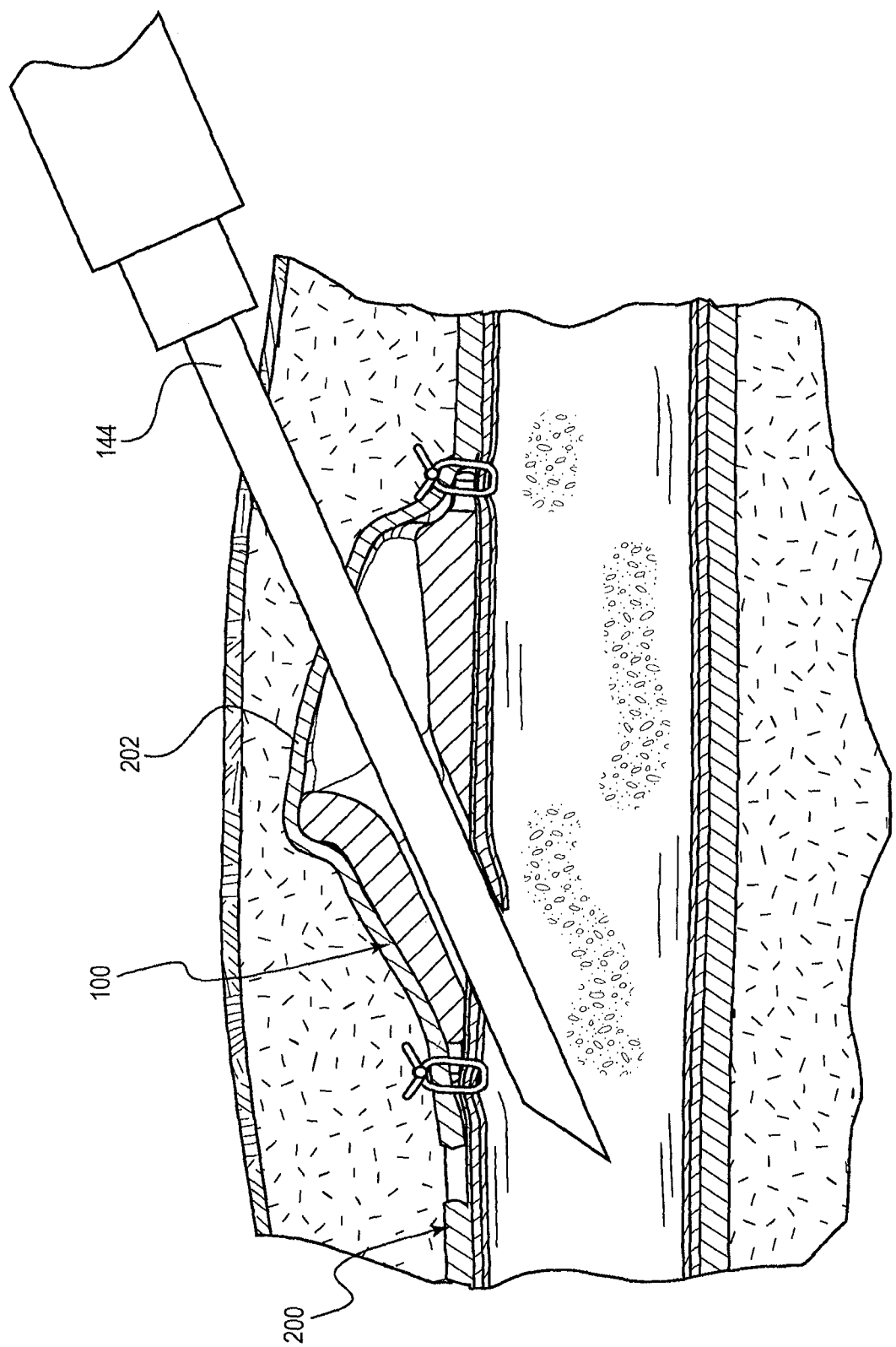
FIG. 12 is a cross-sectional view of a stage of another illustrative method relating to the creation and use of a buttonhole access site to access a lumen of a vessel.

FIG. 12 depicts an embodiment of the vascular access port 100 that has been implanted in the patient 210 via a method such as that depicted in FIGS. 10A-10G. A portion of the adventitia layer 202 of the vessel 200 thus extends over the vascular access port 100. Accordingly, when an access device 144 is inserted into the vessel 200 via the access port 100, it passes through the adventitia layer 202 before entering the vascular access port 100. Otherwise, procedures for creating and using buttonholes can be similar to those described above with respect to FIGS. 11A-11E.

Figure 13:
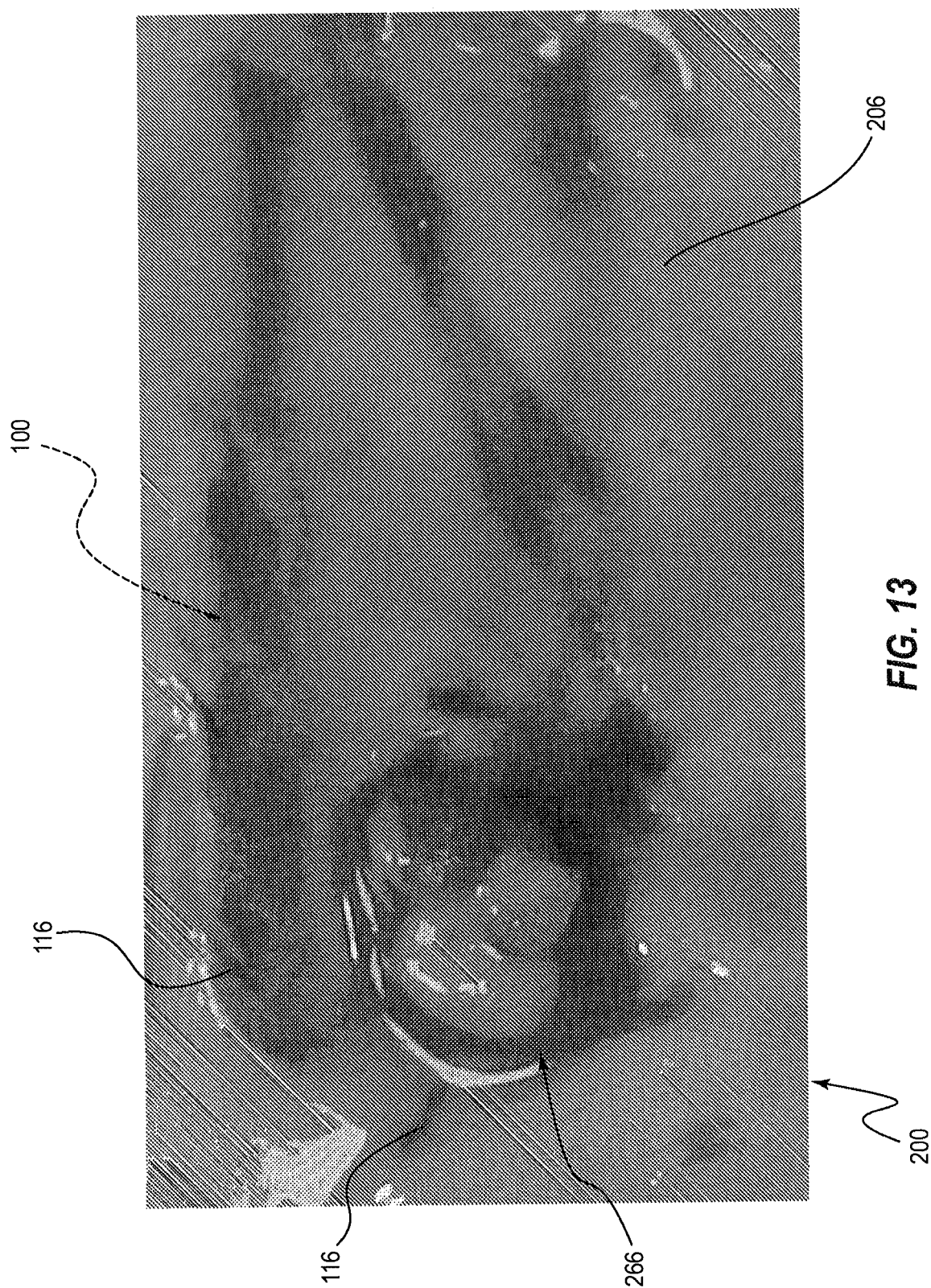
FIG. 13 is a bottom plan view of a filleted vessel that bears an embodiment of a buttonhole access site that has been created via an embodiment of a vascular access port.

FIG. 13 depicts an illustrative example of an embodiment of a buttonhole access site 266 in a vessel 200 that was formed by repeated insertion of access devices 144 through an embodiment of a vascular access port 100. FIG. 13 is a photograph of a filleted portion of the vessel 200, and is shown from a bottom plan view thereof (i.e., a view directed toward the intima layer 206). A contour of the vascular access port 100 is visible in the photograph, as are portions of a running suture 116 that extend through the initima layer 206.

In this particular example, the vascular access port 100 was implanted in a sheep for a period of 9 weeks. After a waiting period to permit for tissue ingrowth, a sharp needle was inserted through the vascular access port 100 to access the vessel 200. Six (6) additional access events were conducted thereafter using a sharp needle, followed by twelve (12) access events using a blunt needle. Accordingly, a total of nineteen (19) cannulations were performed. The access events were conducted at a frequency of three per week.

Figure 14A:
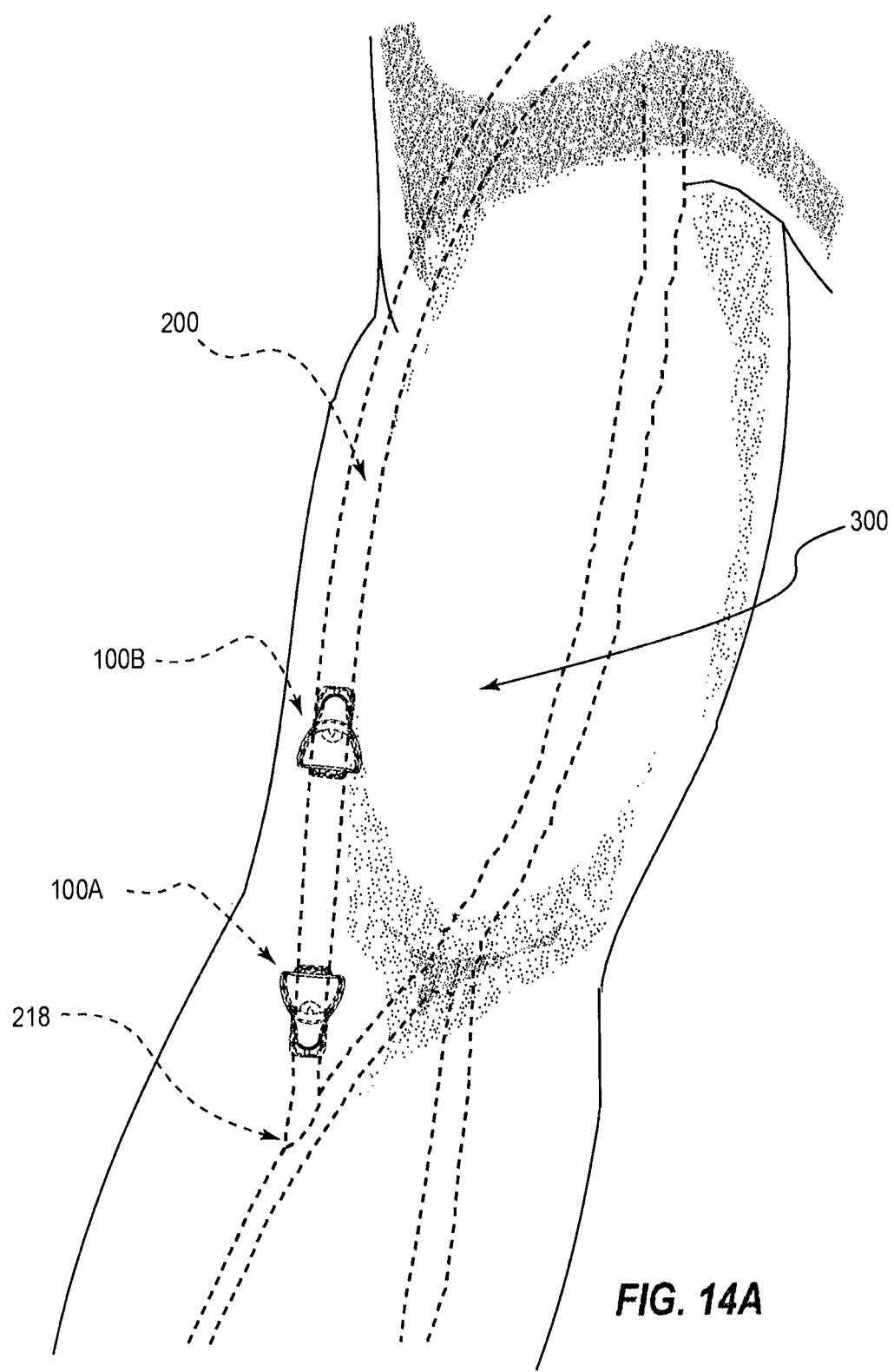
FIG. 14A is a perspective view of an embodiment of a vascular access system that can be used for hemodialysis.

FIG. 14A depicts an embodiment of a hemodialysis system 300 that includes two vascular access ports 100A, 100B. Both of the ports 100A, 100B are shown attached to a vessel 200 that is associated with an arteriovenous fistula 218. One port 100A is directed upstream such that a forward end thereof points in a direction opposite to the flow of blood through the vessel 200, and the other port 100B is directed downstream such that a forward end thereof points in the direction of the blood flow through the vessel 200. A fistula needle may be introduced into each of the ports 100A, 100B and hemodialysis performed. The first port 100A can be an uptake port through which blood is removed from the vessel 200 and delivered to a hemodialysis machine, and the second port 100B can be a return port through which filtered blood is returned to the vessel 200 from the hemodialysis machine.

In other embodiments, the hemodialysis system 300 can comprise only a single vascular access port 100A or 100B. Hemodialysis may be conducted thereby via any suitable method, such as a single-needle hemodialysis technique.

In still other embodiments, the hemodialysis system 300 includes more than two vascular access ports 100A, 100B. A clinician thus can rotate among the ports 100A, 100B, thereby leaving one or more of the ports unused during any given hemodialysis session.

Figure 14B:
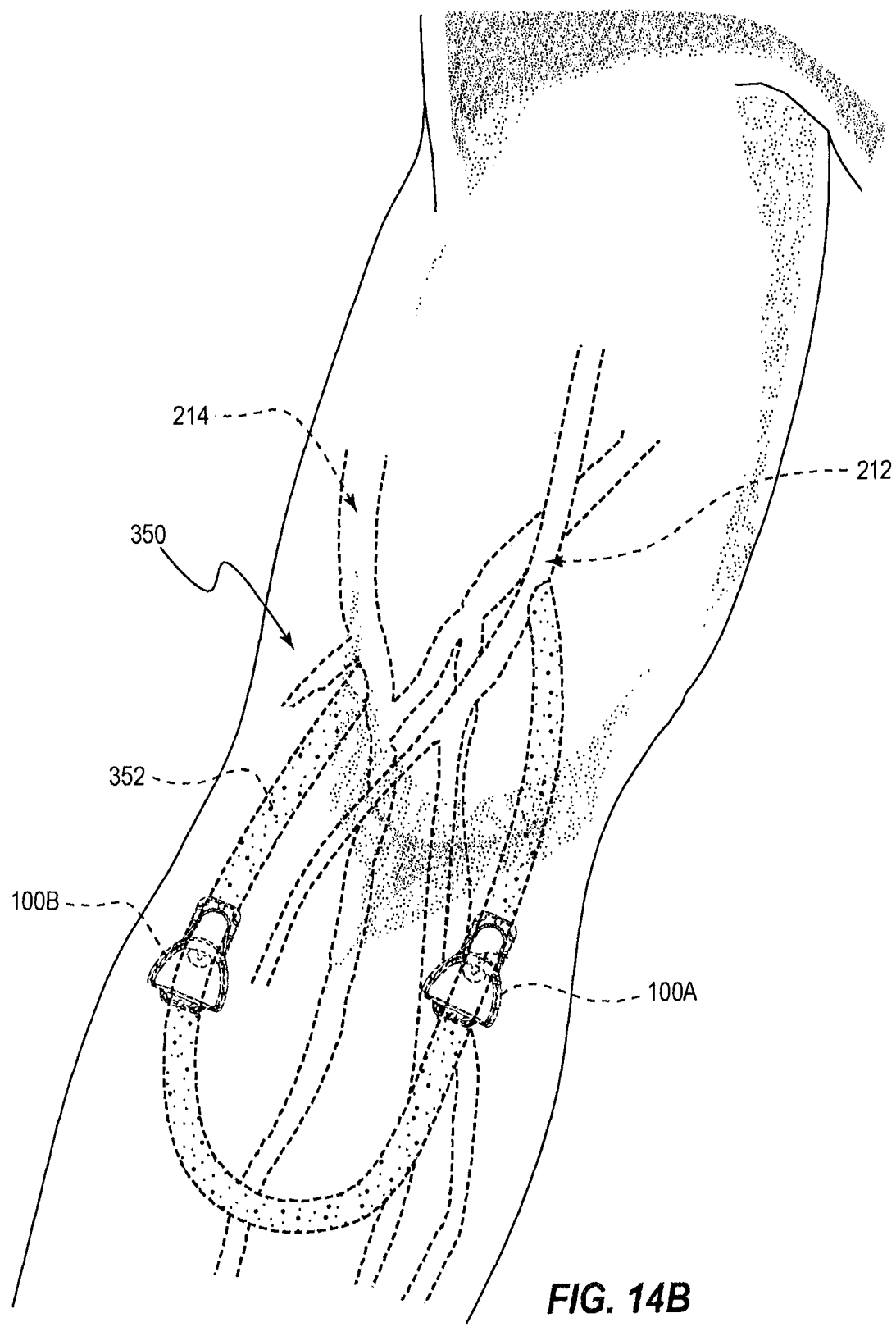
FIG. 14B is a perspective view of another embodiment of a vascular access system that can be used for hemodialysis.

FIG. 14B depicts another embodiment of a hemodialysis system 350. The illustrated embodiment includes two vascular access ports 100A, 100B, but more or fewer ports are possible. Both of the ports 100A, 100B are shown attached to an artificial graft vessel 352 that serves as a shunt between an artery 212 and a vein 214. The graft vessel 352 can comprise any suitable material, such as e-PTFE. The ports 100A, 100B can be attached to the graft vessel 352 prior to its implantation, or may be attached to the graft vessel 352 after it has been implanted. The hemodialysis system 350 can function similarly to the system 300 described above, with the port 100A serving as an uptake port and the port 100B serving as a return port.

Figure 15:
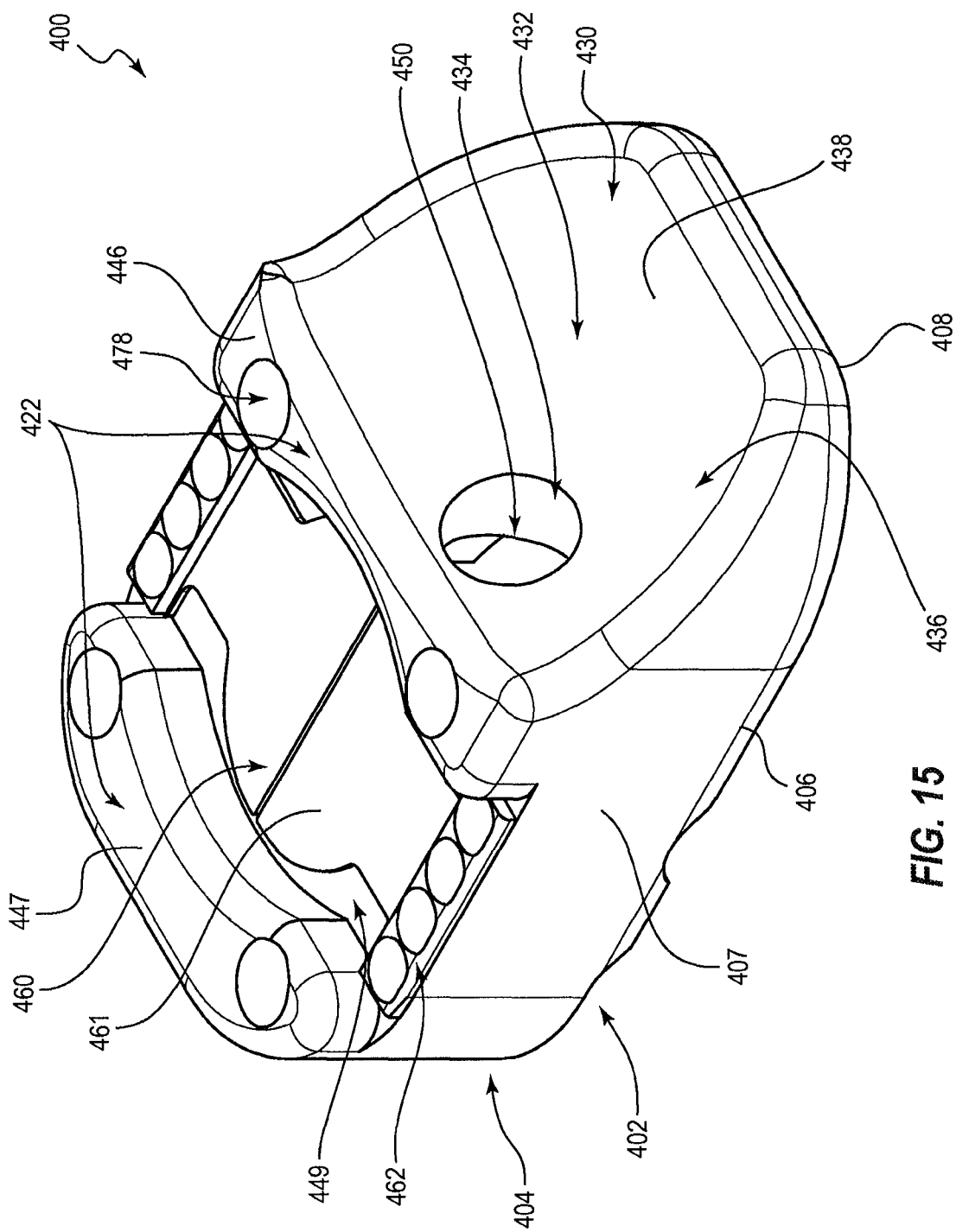
FIG. 15 is a top perspective view of another embodiment of a vascular access port.
Figure 16:
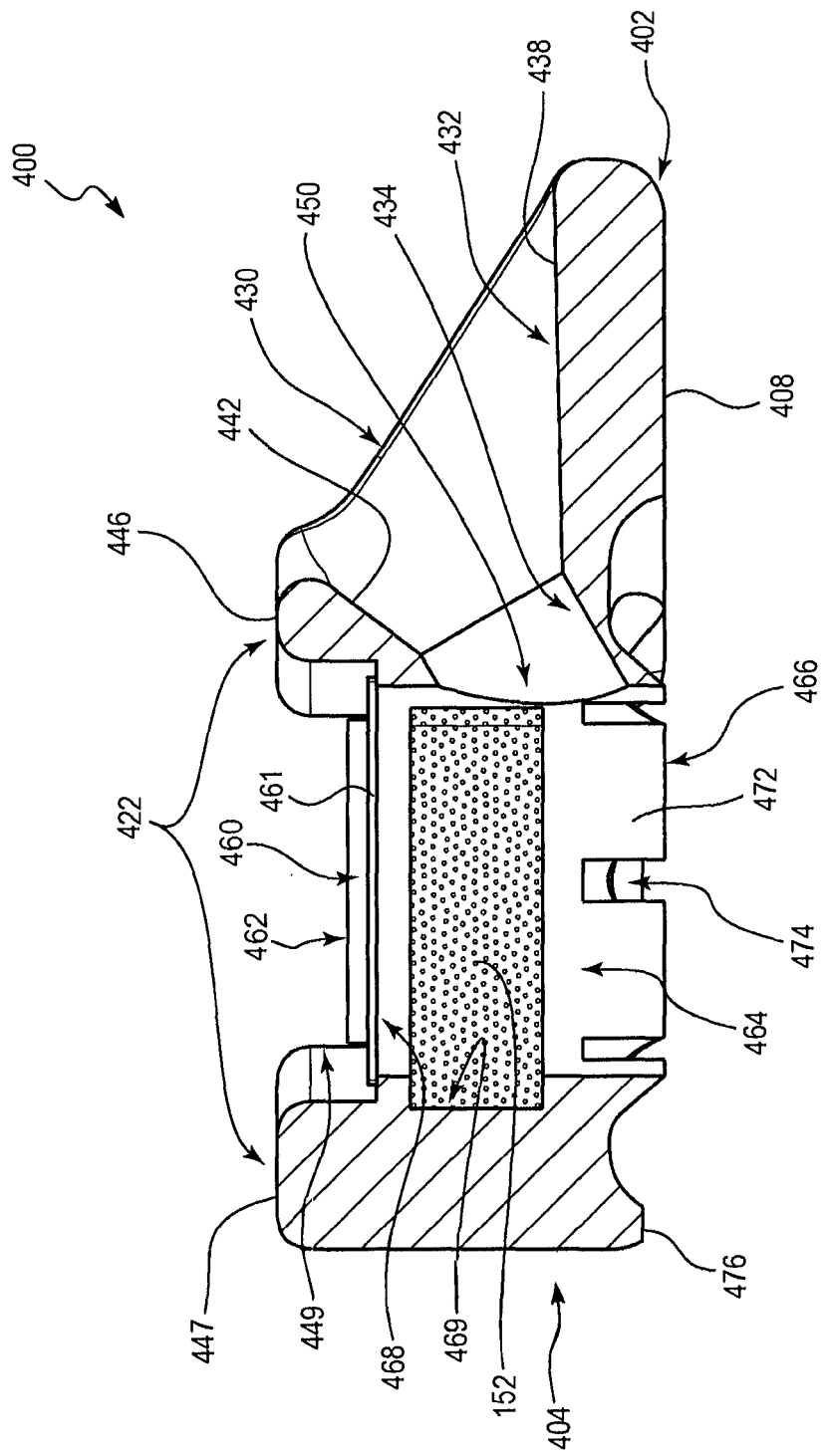
FIG. 16 is a cross-sectional view of the vascular access port of FIG. 15.
Figure 17:
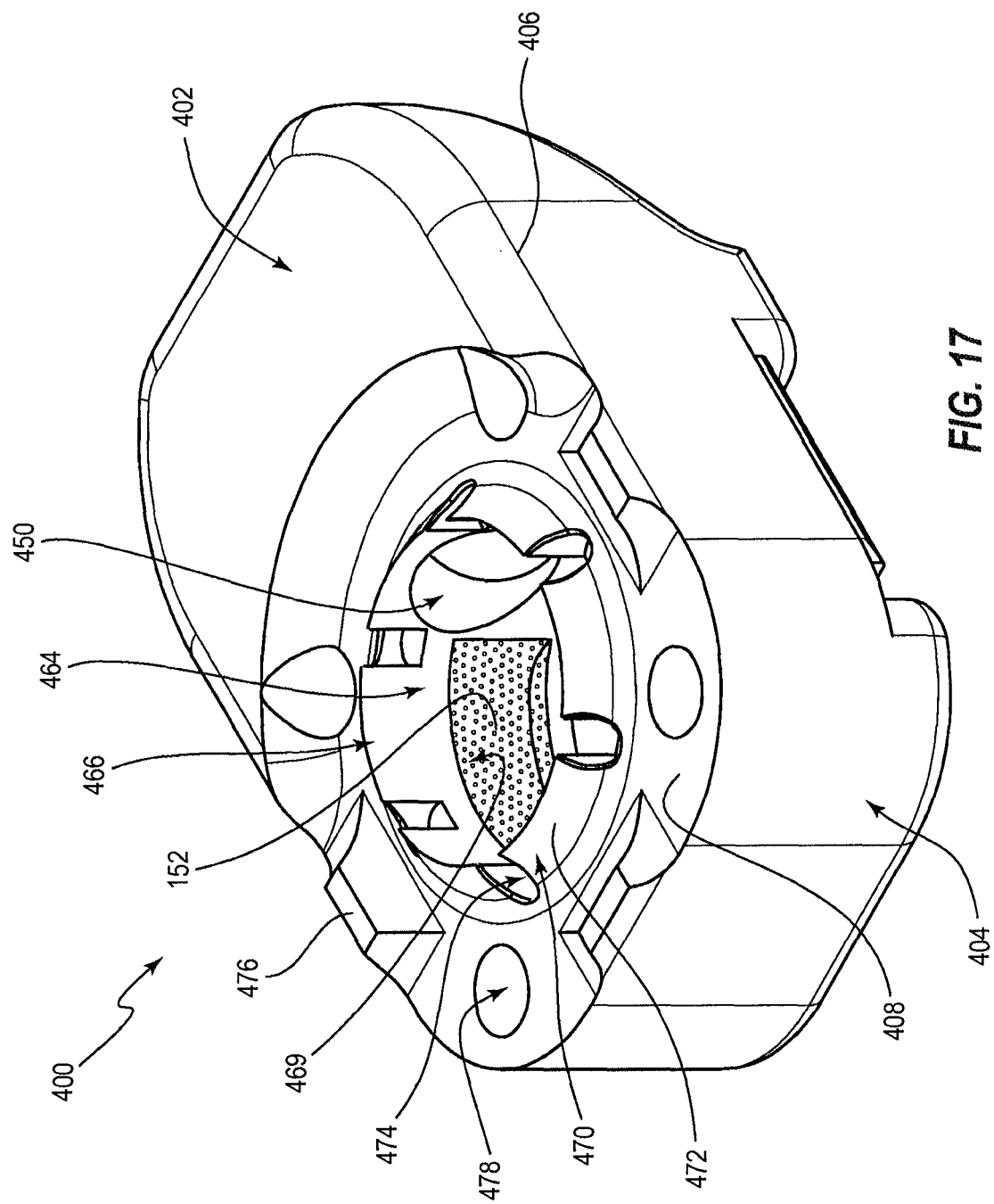
FIG. 17 is a bottom perspective view of the vascular access port of FIG. 15.

FIGS. 15-17 illustrate another embodiment of a vascular access port 400, which can resemble the vascular access port 100 described above in certain respects. Accordingly, like features are designated with like reference numerals, with the leading digits incremented to "4." Relevant disclosure set forth above regarding similarly identified features thus may not be repeated hereafter. Moreover, specific features of the vascular access port 400 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the vascular access port 400. Any suitable combination of the features and variations of the same described with respect to the vascular access port 100 can be employed with the vascular access port 400, and vice versa. This pattern of disclosure applies equally to further embodiments depicted in subsequent figures and described hereafter.

Moreover, additional embodiments of vascular access ports are described in U.S. patent application Ser. No. 12/697,167, titled VASCULAR ACCESS PORTS AND RELATED METHODS, which is being filed with the U.S. Patent and Trademark Office concurrently herewith and of which the entire contents are hereby incorporated by reference herein. Any suitable combination of the features and variations of the same described with respect to the vascular access ports of the present disclosure can be employed with the vascular access ports set forth in the aforementioned co-pending U.S. Patent Application, and vice versa.

Furthermore, apparatus and methods for implanting embodiments of the vascular access port 400 are described below. Additional apparatus and methods that may suitably be used for this purpose are described in co-pending U.S. patent application Ser. No. 12/480,678, titled TISSUE MANAGEMENT METHODS, APPARATUS, AND SYSTEMS, which was filed on Jun. 8, 2009 and of which the entire contents are hereby incorporated by reference herein. Any suitable combination of the features and variations of the same described with respect to the implantation apparatus and methods of the present disclosure can be employed with the implantation apparatus and methods set forth in U.S. patent application Ser. No. 12/480,678, and vice versa.

The vascular access port 400 can include a base 402 and a body 404 that extends away from the base 402. The base 402 is elongated in a longitudinal direction. In particular, the illustrated base 402 defines a substantially rectangular perimeter 406 that extends a greater distance in a longitudinal direction than it does in a transverse direction. The edges and corners of the rectangular perimeter 106 can be rounded, which can prevent trauma to surrounding tissue when the vascular access port 400 is implanted.

The base 402 can include a base surface or bottom surface 408 that is configured to face a vessel when the vascular access port 400 is coupled to the vessel. The bottom surface 408 is described further below. An outer surface 407 of the body 404 can extend upwardly from the base 402. In particular, the outer surface 407 may extend upwardly from the perimeter 406 of the base 402. In the illustrated embodiment, the outer surface 407 is substantially perpendicular to a plane defined by the bottom surface 408. The body 404 can terminate at an uppermost end thereof at a pinnacle region 422. In the illustrated embodiment, the pinnacle region 422 defines a plane, which can be substantially parallel to the plane defined by the bottom surface 408.

The vascular access port 400 can include a guidance passageway 430, which can resemble the guidance passageway 130 described above. The guidance passageway 430 can include an entry mouth 436 at a proximal end thereof, a funnel region 432, a channel 434, and a distal opening 450. The funnel region 432 can narrow from the entry mouth 436 toward the channel 434 so as to guide an access device 144 toward the channel 434. The entry mouth 436 can be configured to assist in achieving hemostasis, such as in the manners described above. For example, in the illustrated embodiment, the entry mouth 436 is substantially planar (see FIG. 16). The channel 434 can define an angle relative to the bottom surface 408. For example, a central or longitudinal axis of the channel 434 can define any of the angles α described above.

The funnel region 432 can include a base surface 438 that projects rearwardly from the channel 434 and that narrows in the rearward direction. As shown in FIG. 16, the base surface 138 of the funnel region 432 can be angled slightly upwardly (in a rearward direction) relative to the bottom surface 408 of the base 402. The funnel region 432 also can include a backstop portion 442 similar to the backstop portion 142 described above, although the backstop portion 442 is more angled relative to the vertical.

The body 404 can include two palpation projections or ridges 446, 447, which can be oriented substantially transversely. The palpation projections 446, 447 can be spaced from each other by a recess 449 that also runs in a substantially transverse direction. A seal or sealing device 460 can be received within the recess 449 when in a closed state, as shown. The palpation projections 446, 447 thus can act as a barrier to the sealing device 460 when it is closed, which can inhibit, reduce, or prevent surrounding tissue from moving over, moving against, or otherwise interfering with the sealing device 460 when the vascular access port 400 is implanted in a patient, such as may occur via ordinary events (e.g., movement or bumping of the implantation site by a patient) or via intentional palpation of one or more of the palpation projections 446, 447.

The sealing device 460 can be configured to transition from an open state to a closed state, and can seal a portion of the vascular access port 400 when in the closed state. The sealing device 460 can include any suitable closure device, such as, for example, one or more doors, ports, or flaps 461. In the illustrated embodiment, the flaps 461 are fixedly attached to the vascular access port 400 at one end thereof and are able to move relative to the port 400 at an opposite end thereof. In some embodiments, a portion of a flap 461 can be integrally formed with the port 400, or the flap 461 can be formed as separate piece of which a portion is attached to the port 400 via any suitable method (e.g., adhesives, fasteners, welds, etc.). In the illustrated embodiment, each of the outer ends of the flaps 461 is attached to the body 404 of the port 400 via an anchoring device 462, which includes a laser-welded titanium band.

In the illustrated embodiment, each flap 461 is configured to rotate about a hinge region at or adjacent to the anchoring device 462. For example, the flaps 461 can comprise a shape memory alloy (e.g., nickel titanium) or some other resilient material having a natural state that corresponds with the closed state illustrated in FIGS. 15 and 16. Accordingly, as discussed further below, the flaps 461 can be held in an open position to permit implantation devices to extend through the vascular access port 400 during an implantation procedure, and upon removal of the implantation devices, the flaps 461 can return to their natural or closed state.

When in the closed state, the one or more flaps 461 can seal an upper end of the body 404. For example, in the illustrated embodiment, the inner edges of the flaps 461 create a substantially fluid-tight seal with each other and bottom surfaces of the flaps 461 create a substantially fluid-tight seal with a portion of the body 404 that defines a base wall of the recess 449. Other suitable arrangements for sealing the vascular access port 400 are also possible.

With reference to FIGS. 16 and 17, the vascular access port 400 can define an implantation passageway or primary passageway 464, which can extend through both the base 402 and the body 404. In the illustrated embodiment, a longitudinal axis of the primary passageway 464 is substantially perpendicular a plane defined by the bottom surface 408. In other embodiments, a longitudinal axis of the primary passageway 464 can be at a non-perpendicular angle (e.g., an acute angle) relative to the bottom surface 408.

The primary passageway 464 and the guidance passageway 430 can be connected to each other. For example, in the illustrated embodiment, the guidance passageway 430 is joined with the primary passageway 464 in a substantially y-shaped configuration in which the guidance passageway 430 terminates at the primary passageway 464. Stated otherwise, the primary passageway 464 and the guidance passageway 430 can be in fluid communication with each other via the opening 450. In the illustrated embodiment, the channel 434 is spaced from the bottom surface 408 of the port 400 and is configured to direct an access device 144 into the primary passageway 464 via the opening 450, which is positioned in a sidewall that defines the primary passageway 464. The primary passageway 464 can have a lower opening 466, which can be positioned at the bottom surface 408, and an upper opening 468, which can be selectively sealed by the flaps 461 as described above.

In other embodiments, the guidance passageway 430 can be joined with the primary passageway 464 in a substantially x-shaped configuration in which the guidance passageway 430 intersects and extends through the primary passageway 464. In certain of such embodiments, multiple openings may extend through the bottom surface 408 of the vascular access port 400; for example, the lower opening 466 of the primary passageway 464 and a distal opening of the guidance passageway 430 each can extend through the bottom surface 408 of the vascular access port 400 at a different position. In still other embodiments, the guidance passageway 430 may be fully separate from the primary passageway 464, and each passageway 430, 464 can define a separate opening in the bottom surface 408 of the vascular access port 400. Other arrangements of the passageways 430, 464 are also contemplated.

The primary passageway 464 can include a tissue ingrowth region 469. In the illustrated embodiment, the ingrowth region 469 comprises a recessed groove that can be covered with any suitable ingrowth-inducing covering 152. In the illustrated embodiment, the ingrowth region 469 is recessed relative to an inner wall that defines the primary passageway 464. Such an arrangement can facilitate insertion and removal of components of the implantation assembly 500 through the primary passageway 464 and/or otherwise inhibit or prevent interaction between the ingrowth-inducing covering 152 and the components during their insertion and removal.

With continued reference to FIGS. 16 and 17, the bottom surface 408 can extend inwardly from the perimeter 406 of the base 402 and can terminate at the lower opening 466 of the primary passageway 464. In the illustrated embodiment, a rearward end of the bottom surface 408 is substantially planar. In other embodiments, at least a portion of the bottom surface 408 can be bowed in a transverse direction so as to more closely conform to a surface of a vessel wall in a manner such as discussed above with respect to the bottom surface 108.

The bottom surface 408 can include an attachment area or attachment region 470 that encompasses the bottom opening 466. The attachment region 470 can be configured to assist in attaching the vascular access port 400 to a vessel, and can be configured to provide a hemostatic seal about the opening 466, as discussed further below. In the illustrated embodiment, the attachment region 470 includes a plurality of outward extensions, projections, or everting members 472. The everting members 472 can be substantially wedge-shaped, which, as discussed below, can assist in the eversion of a vessel wall. An attachment recess 474 separates each set of adjacent everting members 472 from each other.

The bottom surface 408 also can define one or more stops 476, which can project downwardly or away from the body 404. Additionally, one or more connection passages or connection channels 478 can extend upwardly from the bottom surface 408. In the illustrated embodiment, the connection channels 478 extend fully through both the base 402 and the body 404 (see FIG. 1). The features described in the present paragraph can be configured to cooperate with an attachment clip to secure the vascular access port 400 to a vessel, as discussed hereafter.

In some embodiments, at least a portion of the bottom surface 408 includes an ingrowth-inducing covering, such as the ingrowth inducing covering 152 discussed above. In other or further embodiments, at least a portion of the body 404 can include an ingrowth-inducing covering at an exterior surface thereof.

Figure 18:
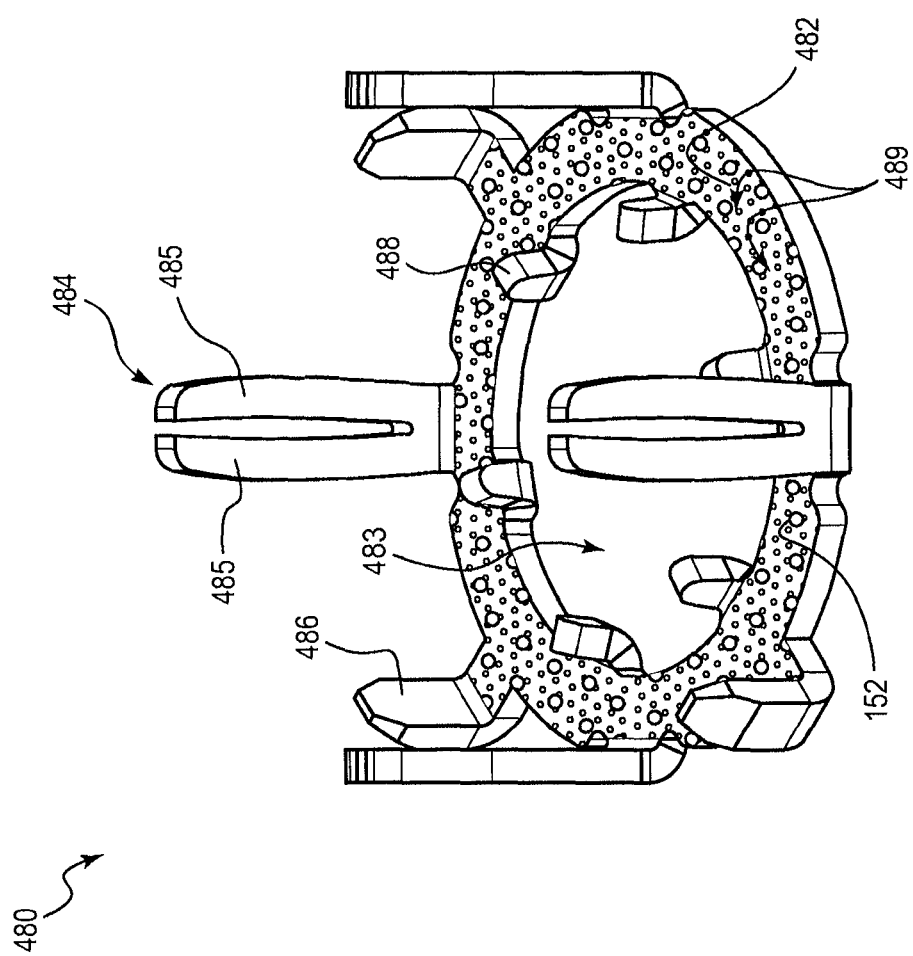
FIG. 18 is a top perspective view of an embodiment of a clip that can be coupled with the vascular access port of FIG. 15.

FIG. 18 illustrates an embodiment of a clip 480 that is compatible with the vascular access port 400. The clip 480 can comprise any suitable material, such as, for example, stainless steel, and can be formed in any suitable manner, such as, for example, machining (e.g., electrical discharge machining), laser cutting, or progressing metal bending. The clip 480 may be referred to as an attachment device.

The clip 480 includes a base ring 482, which is substantially circular in the present embodiment. Any suitable size and shape of the base ring 482 is contemplated. For example, in some embodiments, the base ring 482 may be oval-shaped. The size of the base ring 482 can be configured to interact in a desired manner with a vessel to which the vascular access port 400 is to be attached. For example, in some embodiments an outer diameter of the base ring 482 may be slightly larger than, no larger than, approximately the same as, or smaller than an outer diameter of the vessel with which the vascular access port 400 is configured to be coupled. The base ring 482 can define an opening 483 at an interior thereof.

The clip 480 can include a plurality of features that extend upwardly from the base ring 482. For example, one or more connection posts 484 can project upwardly from the base ring 482. In the illustrated embodiment, four connection posts 484 extend upwardly from an outer edge of the base ring 482, and adjacent posts 484 are spaced from each other at 90 degree intervals. More or fewer connection posts 484 may be used, and the posts 484 may be arranged at other positions relative to each other. In the illustrated embodiment, each connection post 484 comprises two resilient prongs 485, which can be configured to provide outwardly directed forces when flexed toward each other. In other embodiments, more than two prongs 485 may be associated with a given connection post 484. Other arrangements for the connection posts 484 are contemplated.

One or more retention posts 486 likewise can extend from the base ring 482. In the illustrated embodiment, the retention posts 486 project outwardly somewhat before projecting upwardly such that they are further from an axial center of the base ring 482 than are the connection posts 484. The retention posts 486 can have tips that are angled or chamfered in multiple directions, as in the illustrated embodiment, or that are rounded or radiused, which can aid in initially inserting the clip 480 into a temporary retention device, which is discussed below. The illustrated embodiment includes three retention posts 486 that are constrained to approximately one half of the base ring 482 and that are spaced from each other by approximately 90 degrees. The portion of the base ring 482 that is devoid of retention posts 486 can be configured to be positioned adjacent to the rearward end of the vascular access device 400, or beneath the guidance channel 430 (see, e.g., FIGS. 19 and 23A).

One or more grips or teeth 488 likewise can extend from the base ring 482. In the illustrated embodiment, six teeth 488 extend upwardly from an interior edge of the base ring 482. Adjacent teeth 488 are spaced from each other by about 60 degrees. More or fewer teeth 488 may be used, and the teeth 488 may be arranged at other positions relative to each other.

At least a portion of the clip 480 can include an ingrowth-inducing covering 152, which can encourage tissue ingrowth to secure the clip 480 to a wall of a vessel. In the illustrated embodiment, the ingrowth-inducing covering 152 extends over an upper surface of the base ring 482, and also extends over a lower surface thereof (see FIG. 19). In other embodiments, the covering 152 may extend only over one of the upper and lower surfaces of the base ring 482. One or more holes 489 may extend through the base ring 482 to permit tissue to grow therethrough so as to enhance the attachment of the vascular access port 400 to a vessel.

Figure 19:
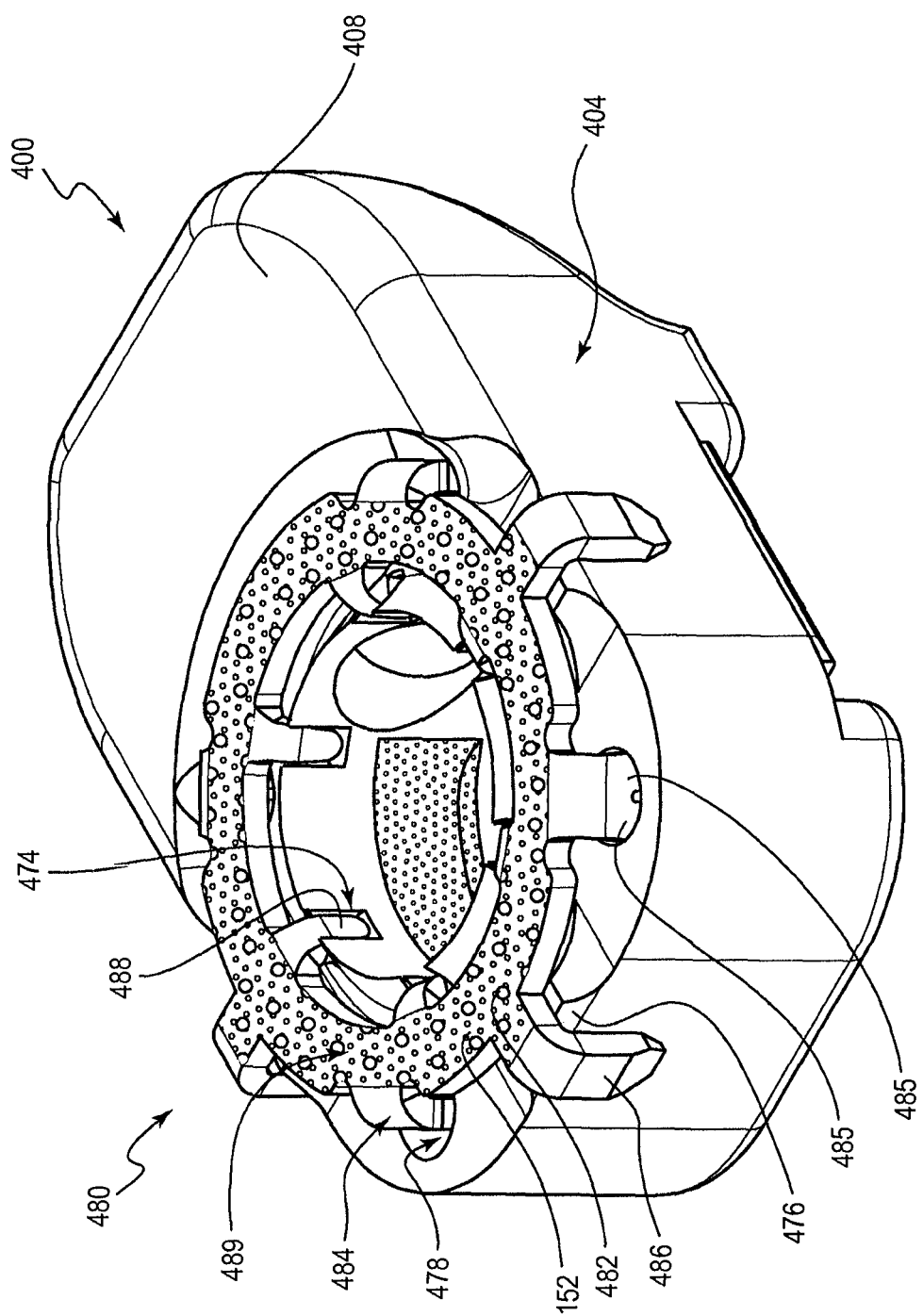
FIG. 19 is a bottom perspective view of the vascular access port of FIG. 15 coupled with the clip of FIG. 18.

FIG. 19 illustrates the clip 480 connected with the vascular access port 400. The stops 485 can interact with the outward projection portions of the retention posts 486 to prevent the base ring 482 from contacting the bottom surface 408 of the vascular access port 400. Additionally, the retention posts 486 are spaced from the body 404 of the vascular access port 400.

The connection posts 484 are received within and frictionally engage the connection channels 478. In some embodiments, the connection channels 478 define a substantially constant inner diameter such that the force by which the resilient prongs 485 maintain a connection between the clip 480 and the vascular access port 400 is substantially constant as the prongs 485 are advanced deeper within the connection channels 478. In other embodiments, an inner diameter of the connection channels 478 may decrease with increasing distance from the bottom surface 408 such that the retention or connection forces increase as the prongs 485 are advanced deeper into the channels 478.

The teeth 488 of the clip 400 are received within the attachment recesses 474 of the vascular access port 400. In the illustrated embodiment, the attachment recesses 474 are relatively deep, narrow, and parallel to each other. The sidewalls of the attachment recess 474 may be spaced so as to allow a portion of a vessel wall to fit between them and the teeth 488 without unduly crushing or otherwise damaging the vessel wall when the clip 480 is coupled with the vascular access port 400, as further discussed below. Accordingly, in the illustrated embodiment, the teeth 488 can cooperate with the attachment recesses 474 to capture, grip, or retain a wall of a vessel, as discussed below. In other embodiments, the sidewalls of the attachment recesses 474 may be spaced further from each other at an entry end thereof and/or may be more rounded (see, e.g., FIG. 25). In still other embodiments, there may be less or even no spacing between the teeth 488 and the sidewalls of the attachment recesses 474, and/or the teeth 488 can be configured to puncture the vessel wall when the teeth 488 are received within the attachment recesses 474.

Figure 20:
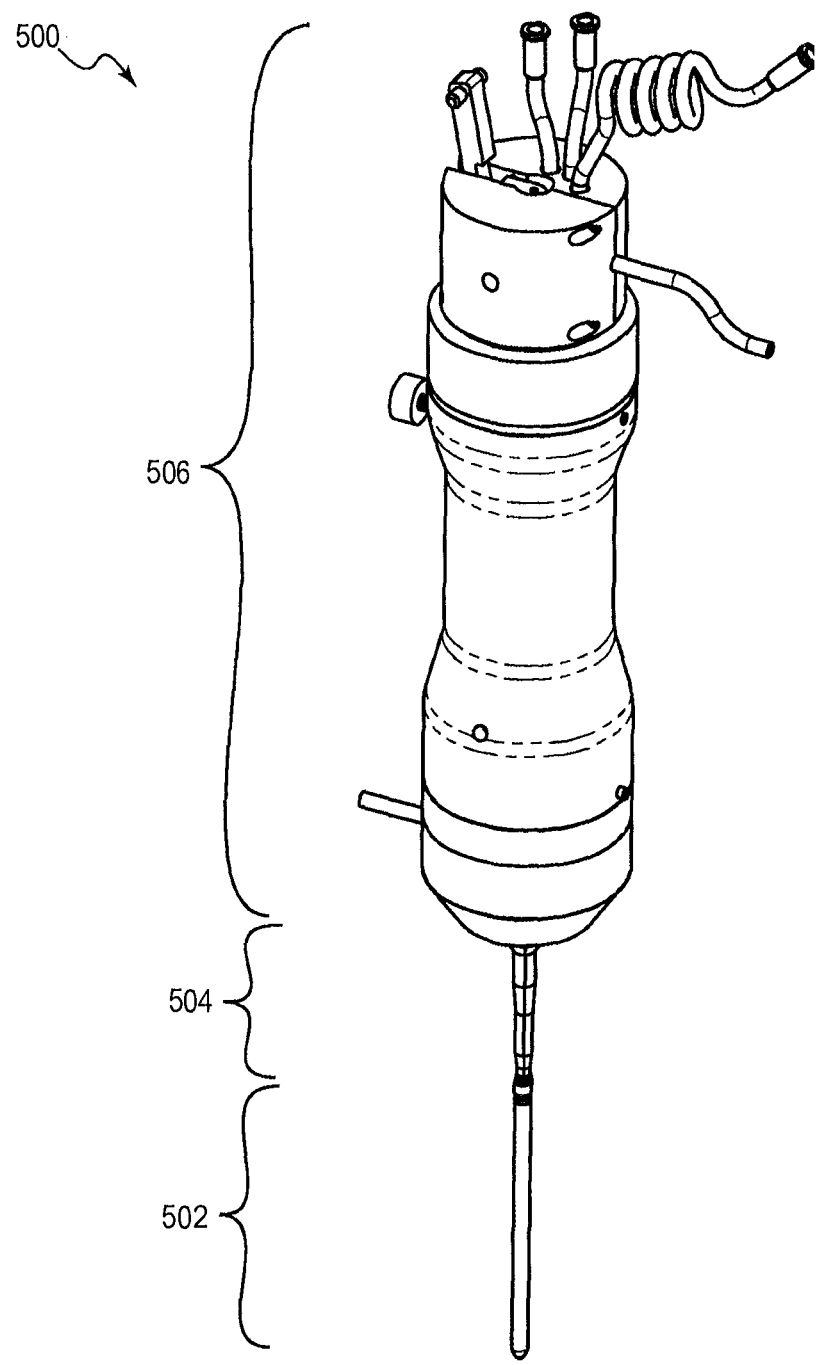
FIG. 20 is a perspective view of an embodiment of a percutaneous implantation assembly that can be used to implant the vascular access port of FIG. 15 within a patient.
Figure 21:
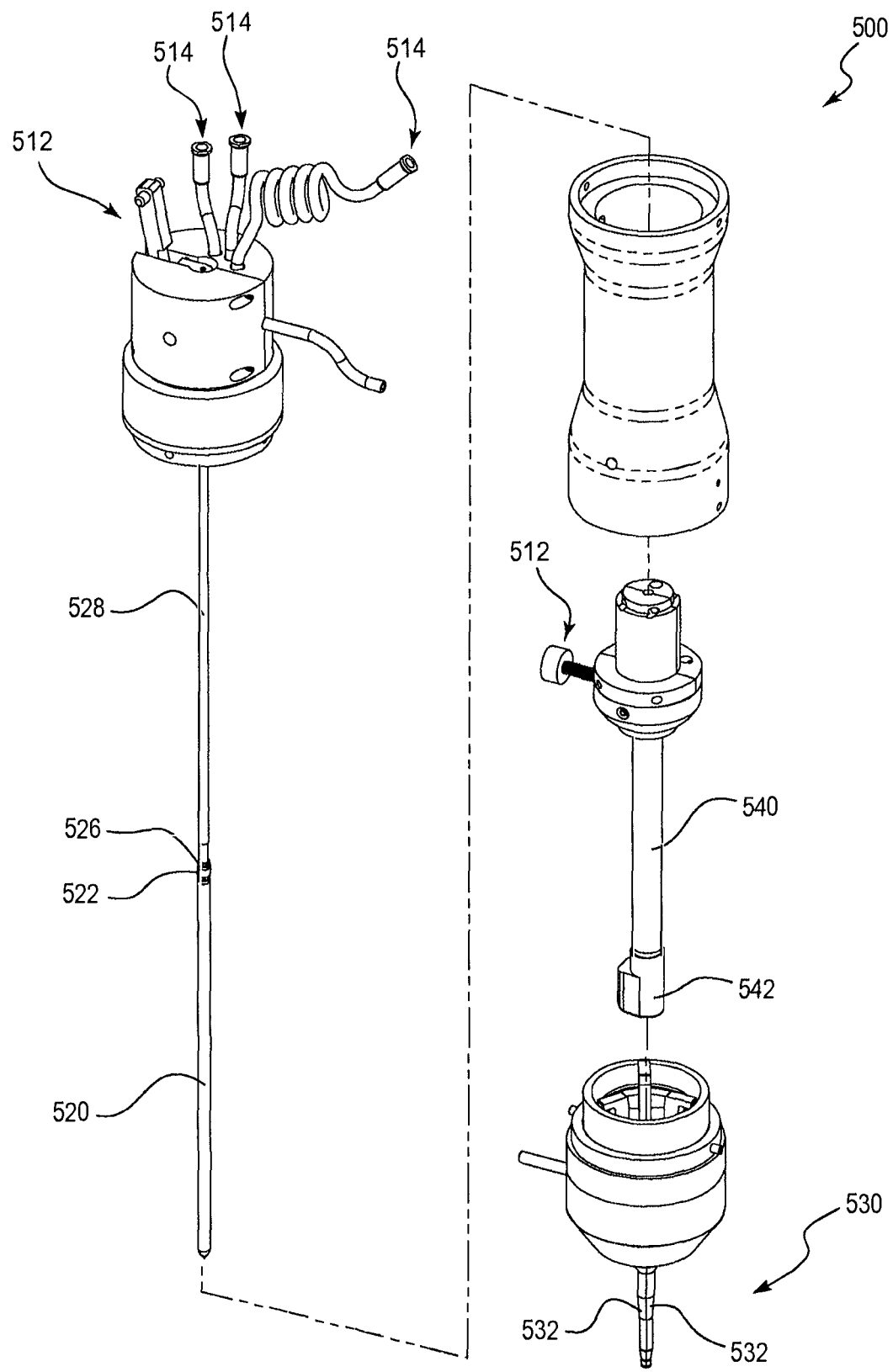
FIG. 21 is a partially exploded perspective view of the percutaneous implantation assembly of FIG. 20.

FIGS. 20 and 21 illustrate an embodiment of a percutaneous implantation assembly 500 that can be used to implant the vascular access port 400 within a patient. The implantation assembly 500 can resemble devices described in U.S. patent Ser. No. 12/480,678, titled TISSUE MANAGEMENT METHODS, APPARATUS, AND SYSTEMS. As shown in FIG. 20, the implantation assembly 500 can generally include an insertion portion 502 that is configured to be inserted through a vessel wall and also to capture the vessel wall, a tract dilation portion 504 that is configured to open a tract through the skin of a patient through which the vascular access port 400 can be advanced into proximity to the vessel wall, and a control portion 506 that remains outside of the patient during the implantation procedure and that is used by a practitioner to activate different functionalities of the implantation assembly 500. With reference to FIG. 21, the implantation assembly 500 can include one or more mechanical actuators 512 and/or one or more hydraulic or pneumatic actuators 514 via which movement of various components of the implantation assembly 500 relative to each other can be achieved.

Figure 22A:
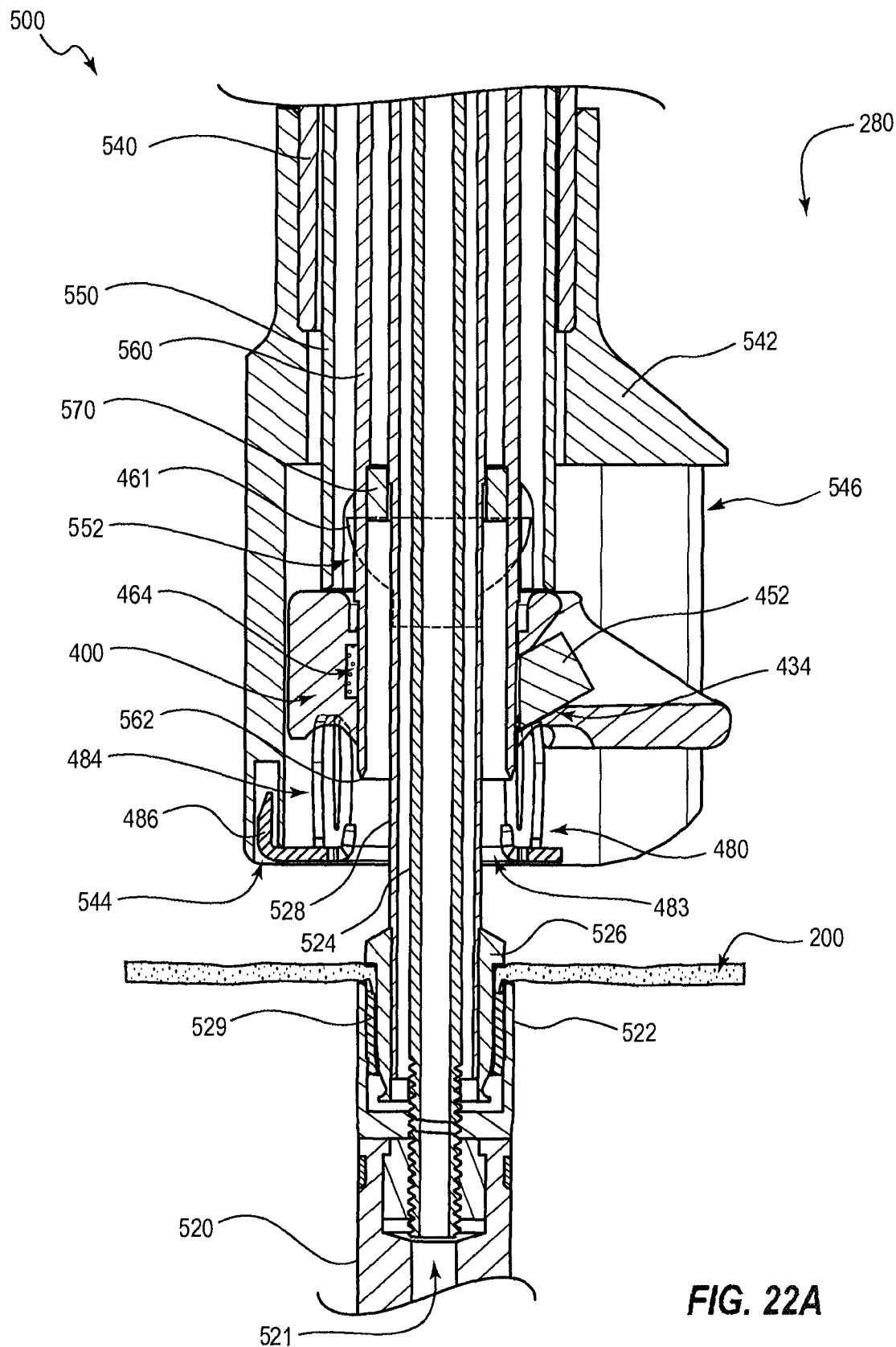
FIG. 22A is a cross-sectional view of a stage of an implantation procedure in which a portion of the percutaneous implantation assembly of FIG. 20 is advanced over another portion of the percutaneous implantation assembly.

With reference to FIGS. 21 and 22A, the implantation assembly 500 can include a flexible introducer tip 520 that is configured to be inserted into the lumen of a vessel 200. The introducer tip 520 can be flexible so as to readily deform to follow a lumen the blood vessel 200 once inserted therein, and it can be substantially atraumatic to an inner surface of an inner surface of the 200 so as to be able to follow the inner surface substantially without imparting damage thereto. For example, in various embodiments, the introducer tip 520 can comprise a flexible material such as polyurethane, thermoplastic elastomer, or silicone rubber. The introducer tip 520 can define at least a portion of a lumen 521 (FIG. 22A) of the implantation assembly 500 through which a guidewire (not shown) may pass. Accordingly, in some embodiments, the introducer tip 520 can be inserted into the blood vessel 200 over the guidewire, and may bend or otherwise deform to follow a contour of the guidewire and/or a contour of the wall of the vessel 200.

In certain embodiments, at least a portion of the introducer tip 520 is radiopaque. For example, in various embodiments, the introducer tip 520 can comprise one or more radiopaque agents such as barium sulfate, bismuth trioxide, titanium dioxide, or the like. In other or further embodiments, the introducer tip 520 can be coated with a lubricious coating, such as a hydrophilic polymer, silicone oil, or other suitable lubricious material. The coating can facilitate a smooth passage of the introducer tip 520 through skin tissue and through the wall of a vessel 200.

The introducer tip 520 can be attached to an anvil 522 in any suitable manner, and the anvil 522 can be attached to an anvil pull tube 524 (FIG. 22A) in any suitable manner. Accordingly, movement of the anvil pull tube 524 can effect movement of the anvil 522 and of the introducer tip 520.

With continued reference to FIGS. 21 and 22A, the implantation assembly 500 can include a clamp 526 that is attached to a clamp tube 528. The clamp tube 528 and the anvil pull tube 524 can be configured to move independently from each other, when desired, such that relative movement between the anvil 522 and the clamp 526 can be achieved.

In the illustrated embodiment, a gripping ring 529 is attached to the clamp 526, and at least a portion of the gripping ring 529 and the clamp 526 can be received within a cavity defined by the anvil 522. The gripping ring 529 can include a plurality of teeth-like prongs that are biased radially outwardly relative to the clamp 526 such that movement of the clamp 526 and the gripping ring 529 outside of the anvil 522 allows the gripping ring 529 to expand radially outwardly so as to assist in capturing a wall of the vessel 200, and movement of the clamp 526 and the gripping ring 529 back into the anvil 522 draws the vessel wall inward and clamps the vessel wall between the anvil 522 and the clamp 526. The wall of the vessel 200 is shown in this clamped configuration in FIG. 22A. In some embodiments, at least a portion of the adventitia layer 202 and substantially a full thickness of each of the media and intima layers 204, 206 (see FIG. 8) can be captured between the anvil 522 and the clamp 526.

With reference again to FIG. 21, the implantation assembly 500 can include a tract dilator 530, which can include a plurality of (e.g., three) dilation legs 532. Once the dilation legs 532 have been inserted into the skin of a patient, they can be expanded to form an expanded implantation tract 280 (FIG. 22A). In various embodiments, the implantation tract 280 may be expanded prior to or after the clamping of the wall of the vessel 200. In FIG. 22A, the implantation tract 280 is shown in an expanded state, but the dilation legs 532 that would encompass the components illustrated in this drawing to maintain expansion of the tract 280 are not shown so as to allow for easier identification of the illustrated components.

Once the implantation tract 280 has been expanded, an adapter tube 540, which can include a retaining adapter 542 at a distal end thereof, can be advanced distally through the tract 280. With reference to FIG. 22A, the retaining adapter 542 can include a plurality of retention channels 544, which can cooperate with the retention prongs 486 to temporarily hold the clip 480 during implantation of the vascular access port 400, and which can release the retention prongs 486 during a later implantation stage as discussed below. In the stage illustrated in FIG. 22A, the proximal tips of the connection prongs 484 of the clip 480 are within the connection channels 478 (see FIG. 17) of the vascular access port 400 such that the port 400 is initially attached to the retaining adapter 542 via the clip 480.

The retaining adapter 542 can define a channel 546 through which the vascular access port 400 can move. In particular, the vascular access port 400 can initially be positioned at a proximal end of the channel 546 and can be advanced to a distal end thereof in subsequent stages of an implantation procedure, as discussed further below.

In the illustrated embodiment, the vascular access port 400 can include a temporary closure or temporary plug 452 within the channel 434. The plug 452 can comprise a hemostatic agent, such as a resorbable material that is configured to resorb, dissolve, or otherwise vacate the channel 434 after implantation of the vascular access port 400, as discussed further below. For example, the plug 452 can comprise any suitable material from the list of resorbable materials set forth above, collagen, plyurethane foam, etc. In some embodiments, the plug 452 comprises Surgicel®.

With continued reference to FIG. 22A, the implantation assembly 500 can include a push tube 550. The push tube 550 can define one or more openings 552 through which the one or more flaps 461 can extend when they are in an open orientation.

The implantation assembly 500 can further include a cutting tube 560. The cutting tube 560 can include a cutting blade 562 at a distal end thereof that can be sufficiently sharp to embed within a proximal surface of the anvil 522. In the illustrated stage, the flaps 461 are in an open orientation, which permits the cutting tube 560 to extend through the primary passageway 464 of the vascular access port 400. The presence of the cutting tube 560 within the primary passageway 464 can maintain the biased flaps 461 in the open orientation. Removal of the cutting tube 560, and components interior thereto, from the primary passageway 464 thus can permit the flaps 461 to transition to the closed orientation (see FIGS. 22D and 23A).

The implantation assembly 500 can include one or more spacers 570 to maintain a desired orientation between adjacent tubes. For example, in the illustrated embodiment, a spacer 570 is attached to an interior surface of the cutting tube 560 and is configured to translate relative to an exterior surface of the clamp tube 528. The spacer 570 can maintain the cutting tube 560 and the clamp tube 528 in a concentric orientation.

FIGS. 22A-22E illustrate various stages of an implantation of the vascular access port 400 using the implantation assembly 500. As previously mentioned, a wall of the vessel 200 can be clamped between the anvil 520 and the clamp 526 and the tract dilator 530 (FIG. 21) can be activated so as to expand the implantation tract 280 and retain the implantation tract 280 in the expanded state. FIG. 22A shows the clamped wall of the vessel 200 and the expanded implantation tract 280.

FIG. 22A further illustrates distal advancement of the adapter tube 540, the retaining adapter 542, the clip 580, the vascular access port 400, the push tube 550, and the cutting tube 560, in unison, over the clamp tube 528. Continued advancement in this manner eventually brings the distal end of the retaining adapter 542 into close proximity or contact with the vessel 200.

Once the retaining adapter 542 is positioned as desired, the anvil pull tube 524 and the clamp tube 528 can be pulled in the proximal direction relative to the other components of the implantation assembly 500. The anvil pull tube 524 and the clamp tube 528 can be pulled in unison such that the wall of the vessel 200 remains clamped between the anvil 522 and the clamp 526. Accordingly, the portion of the vessel 200 that is between the clamp anvil 522 and the clamp 526 can be pulled proximally through the opening 483 of the clip 480.

Figure 22B:
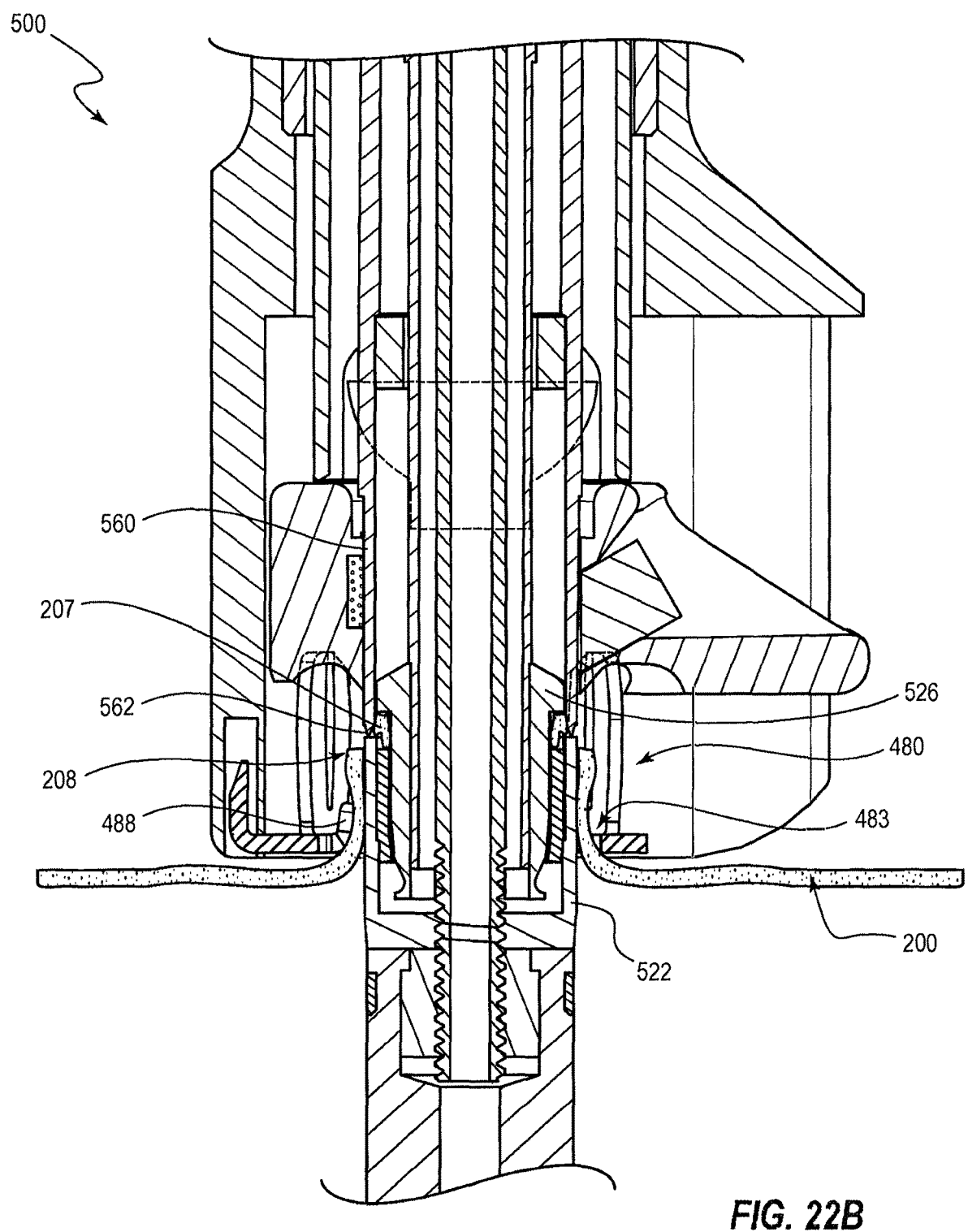
FIG. 22B is a cross-sectional view of another stage of the implantation procedure of FIG. 22A in which a portion of a vessel wall that has been drawn into the percutanous implantation assembly is cut.

FIG. 22B illustrates a stage in which the anvil 522 and the clamp 526 have been pulled in a proximal direction sufficiently far that the anvil 522 is brought into contact with the cutting blade 562 of the cutting tube 560. This action cuts a portion 207 of the vessel wall from the vessel 200, thereby forming an opening in the wall of the vessel 200. The cut portion 207 can remain within the implantation device 500 during subsequent stages of the implantation.

With continued reference to FIG. 22B, the portion of the wall of the vessel 200 that is drawn through the opening 483 of the clip 480 can surround an outer surface of the anvil 522. The close proximity of the teeth 488 of the clip 480 to the outer surface of the anvil 522 can squeeze the vessel wall and prevent it from retracting from the clip 480. A peripheral edge 208 of the vessel 200, which results from the severing of the cut portion 207, can surround or encircle the outer surface of the anvil 522.

Figure 22C:
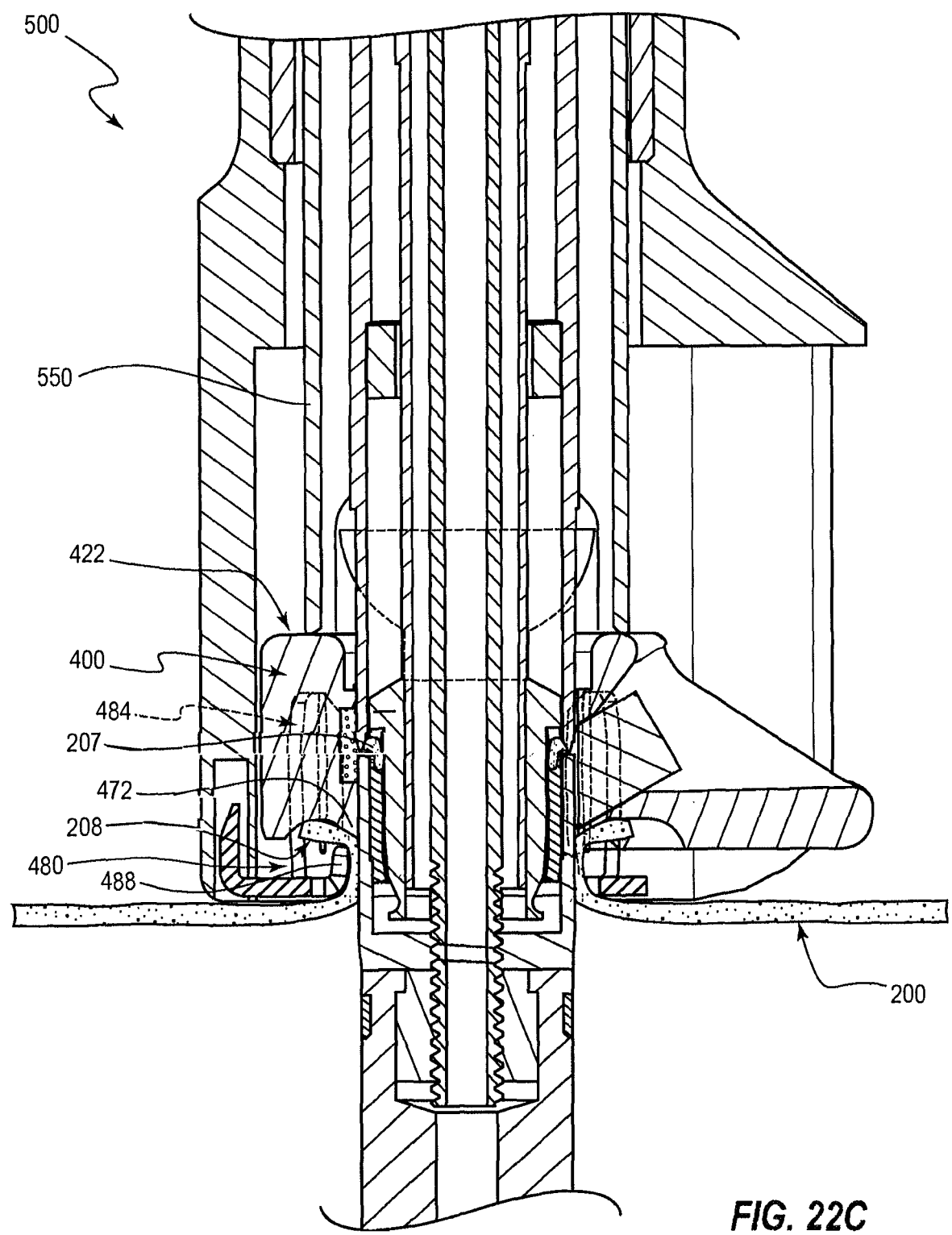
FIG. 22C is a cross-sectional view of another stage of the implantation procedure of FIG. 22A in which an embodiment of a vascular access port is advanced toward the vessel.

With reference to FIG. 22C, once the portion 207 of the vessel wall has been severed, the push tube 550 can be advanced distally, which in turn can advance the vascular access port 400 distally. In the illustrated embodiment, the push tube 550 presses on the pinnacle region 422 of the vascular access port 400, thereby approximating the vascular access port 400 to the clip 480. The everting members 472 of the vascular access port 400 can scoop the peripheral edge 208 of the vessel 200 and can thereby evert the vessel wall over the teeth 488 of the clip 480.

As the vascular access port 400 is advanced distally, the connection prongs 484 of the clip 480 are advanced deeper into the connection channels 478 (see FIG. 19) of the vascular access port 400. The interference fit between the retention posts 486 of the clip 480 and the retention channels 544 of the retention adapter 542 can be sufficiently strong to prevent movement of the clip 480 away from the retention adapter 542 during this approximation of the vascular access port 400 and the clip 480.

Figure 22D:
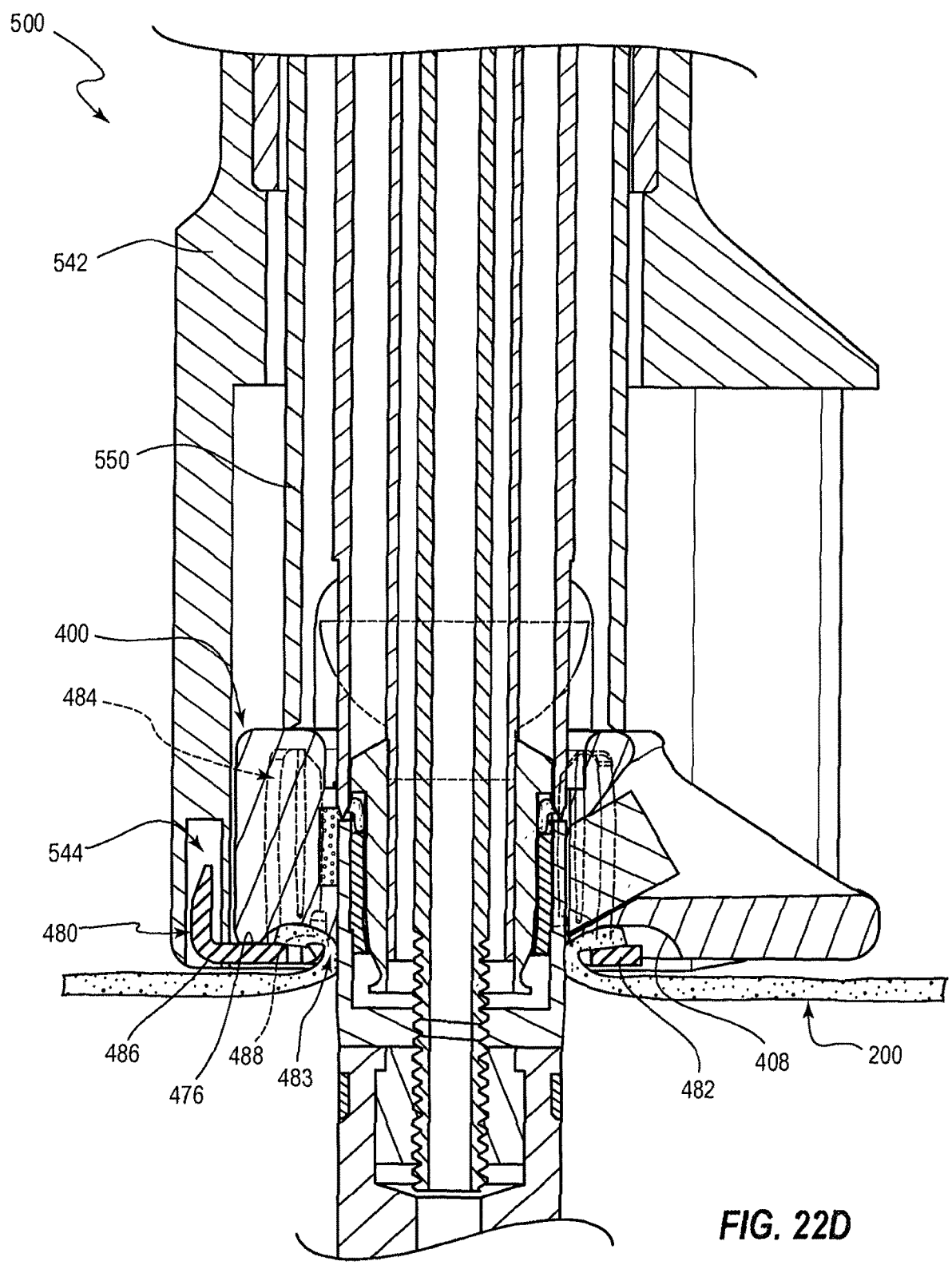
FIG. 22D is a cross-sectional view of another stage of the implantation procedure of FIG. 22A in which stops of the vascular access port are in contact with retention prongs of a clip.

As shown in FIG. 22D, as additional distally directed force is applied to the vascular access port 400 via the push tube 550, the everted vessel wall is compressed over the teeth 488 of the clip 480. As previously mentioned, the teeth 488 can grip the vessel wall as they are received into the attachment recesses 474 (see FIG. 19) of the vascular access port 400 (substantially without crushing or puncturing the vessel wall, in the illustrated embodiment), and the teeth 488 thus can retain the vessel wall and prevent it from retracting through the opening 483 of the clip.

Moreover, the stops 476 of the vascular access port 400 can contact the retention posts 486 of the clip 480. The resulting spacing between the base ring 482 of the clip 480 and the bottom surface 408 of the vascular access port 400 can be sufficiently close to establish a hemostatic seal between the vessel wall and the vascular access port 400 but sufficiently distanced to prevent crushing of the vessel wall. Additional movement of the push tube 550 in the distal direction thus can provide sufficient force to eject or disengage the retention posts 486 from the retention channels 544 of the retention adapter 542 without applying any additional force to the vessel wall that could crush it. In some embodiments, the force required to advance the connection prongs 484 of the clip 480 into the connection channels 478 (see FIG. 19) of the vascular access port 400 is less than the force required to disengage the retention prongs 486 of the clip 480 from the retention channels 544 of the retaining adapter 542.

Figure 22E:
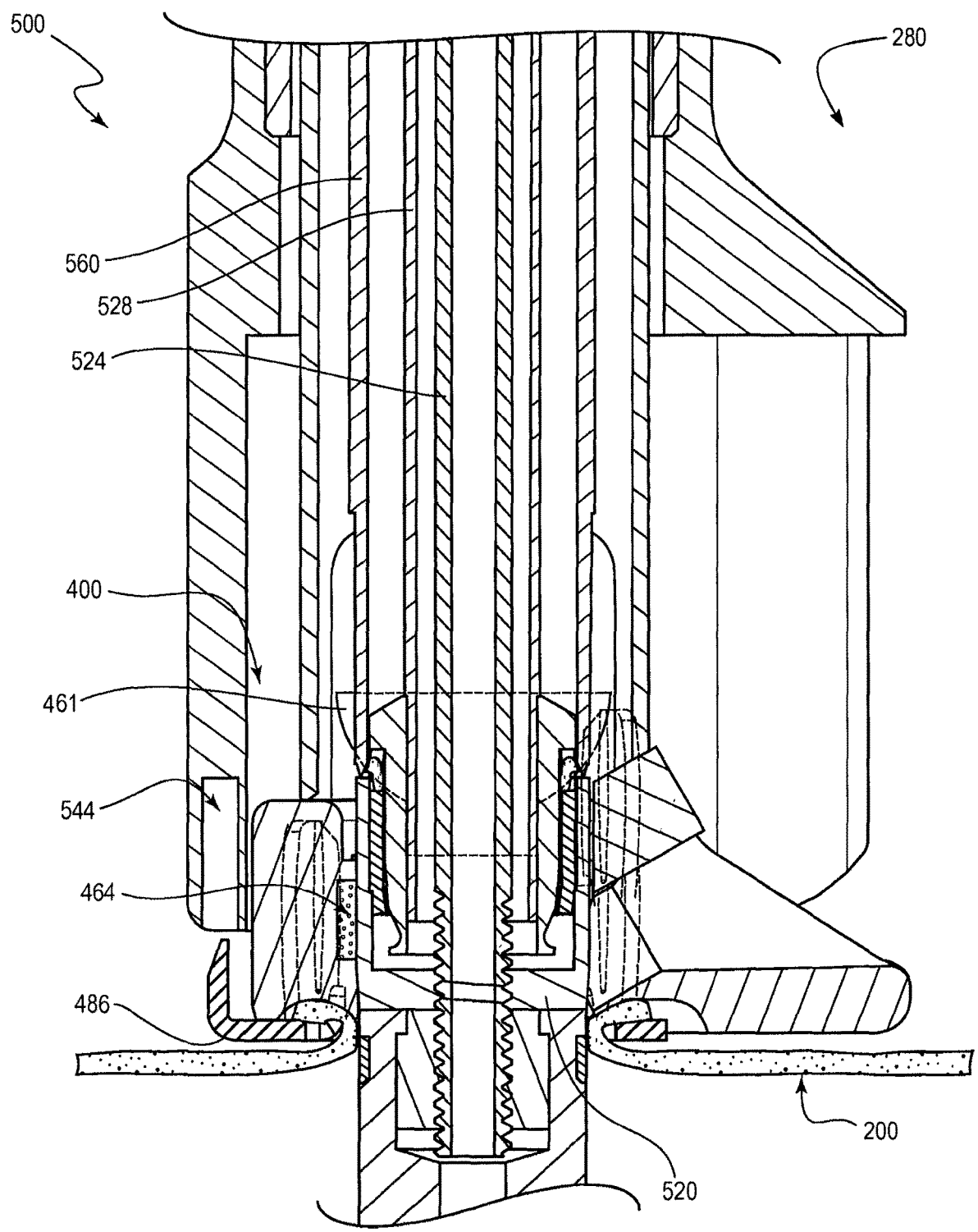
FIG. 22E is a cross-sectional view of another stage of the implantation procedure of FIG. 22A in which a clip to which the vascular access port is attached has been ejected from the implantation assembly.

FIG. 22E depicts a stage after the vascular access port 400 has been attached to the blood vessel 200 and the retention posts 486 have been ejected from the retention channels 544 in which the implantation assembly 500 is being removed from the vascular access port 400. As shown, the cutting tube 560, the clamp tube 528 (and all attachments thereto), and the anvil pull tube 524 (and all attachments thereto) are moved proximally through the primary passageway 464 of the vascular access port 400. Removal of the introducer tip 520 proximally past an upper end of the flaps 461 can permit the flaps 461 to transition automatically or naturally from the open orientation to the closed orientation to thereby seal the primary passageway 464. After removal of the implantation assembly 500 therefrom, the implantation tract 280 can be closed in any suitable manner and allowed to heal.

Figure 23A:
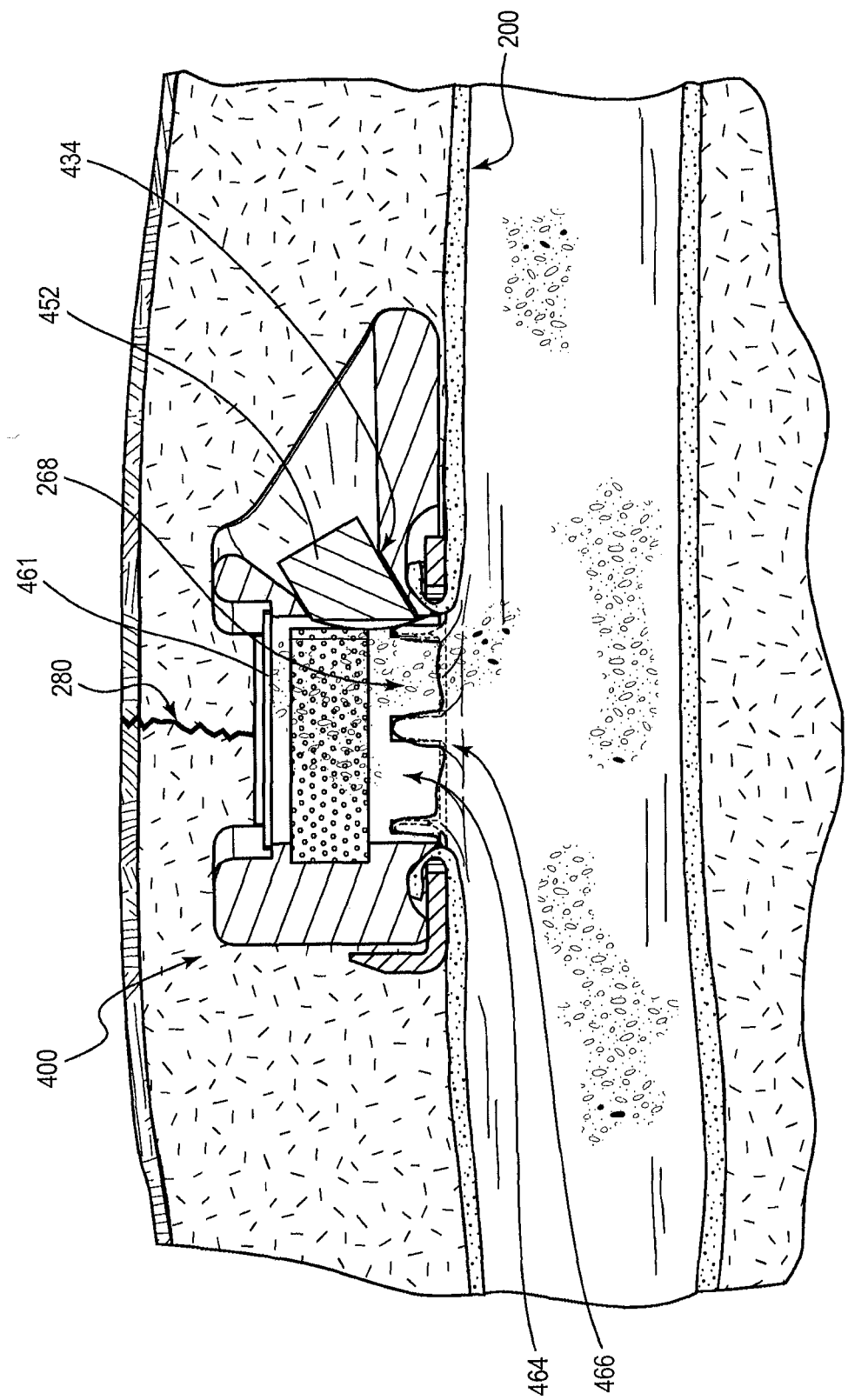
FIG. 23A is a cross-sectional view of a stage of method of using an implanted vascular access port.
Figure 23B:
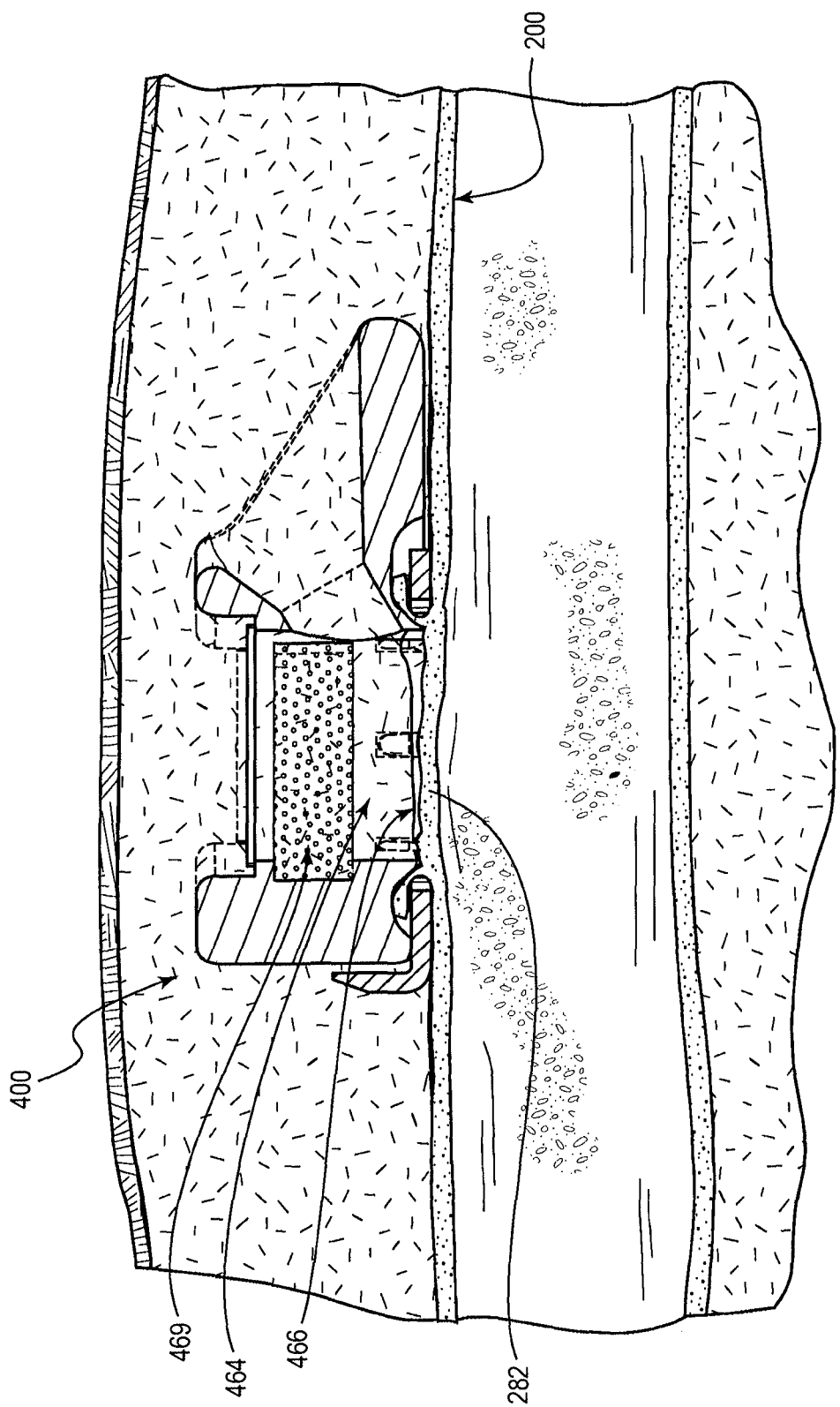
FIG. 23B is cross-sectional view of another stage of the method of FIG. 23A in which healing has taken place.
Figure 23C:
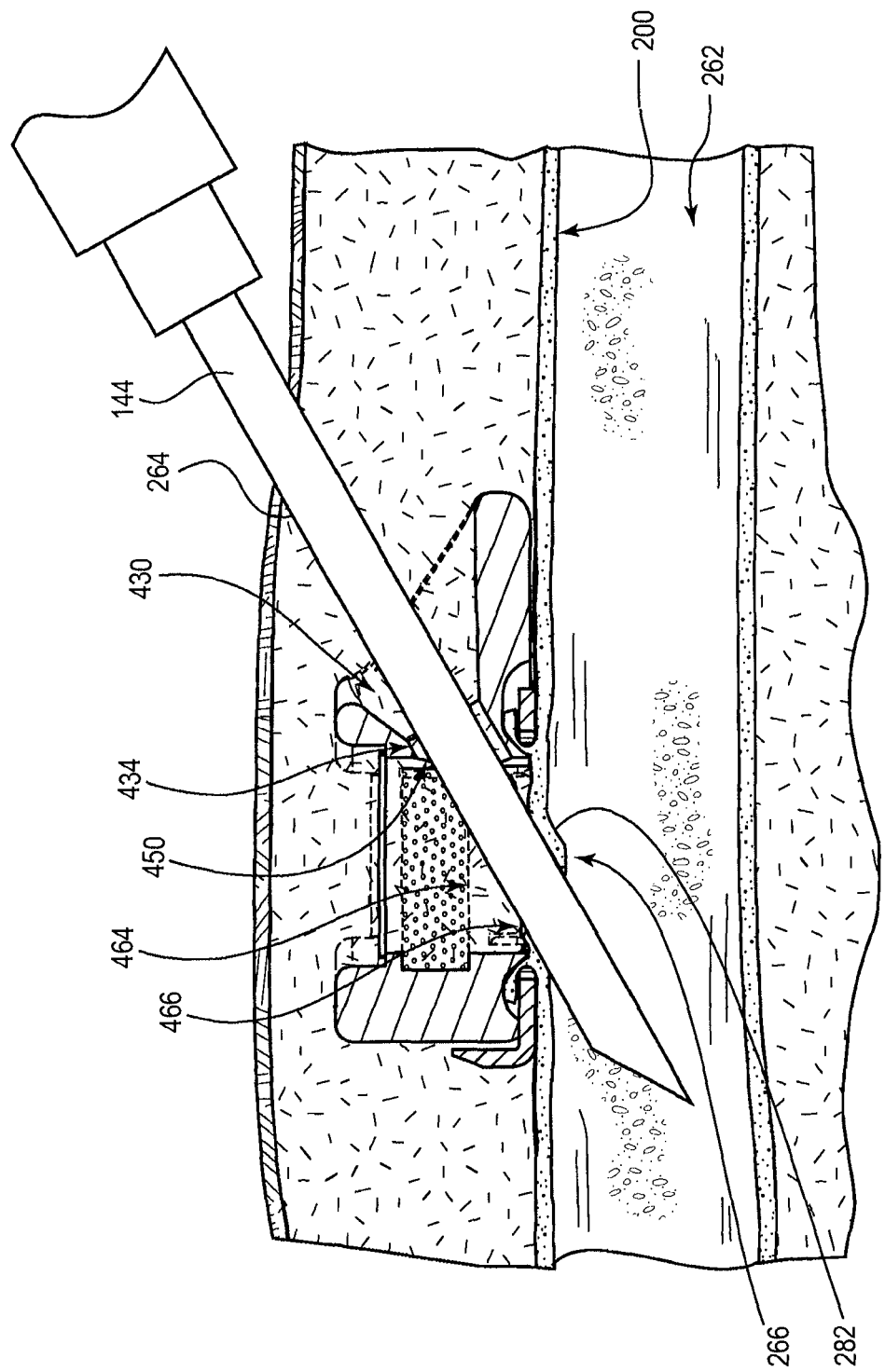
FIG. 23C is a cross-sectional view of another stage of the method of FIG. 23A in which an access device is advanced through the vascular access port.

FIGS. 23A-23C illustrate various stages of a method of using an implanted vascular access port 400. FIG. 23A illustrates the implanted vascular access port 400 just after the implantation tract 280 has been closed. As shown, the plug 452 seals the channel 434. The flaps 461 are in the closed orientation and seal the upper opening 468 of the primary passageway 464. The lower opening 466 of the primary passageway 464 is open and is in fluid communication with an interior of the vessel 200. Accordingly, blood 268 is permitted to enter the primary passageway 464 but is not permitted to exit the vascular access port 400 via either the upper opening 468 of the primary passageway 464 or the channel 434.

FIG. 23B illustrates a stage after the healing has taken place. In particular, the plug 452 has been absorbed and replaced with tissue, as has blood 268 that previously filled the primary passageway 464. The tissue can be firmly attached to the tissue ingrowth region 469 of the primary passageway 464. Also shown is a membrane 282 that has formed naturally over the lower opening 466 of the primary passageway 464, thereby sealing the lower opening 466. The natural membrane 282 can be a continuation of the wall of the vessel 200. In some embodiments, absorption of the plug 452 and/or creation of the membrane 282 can take place within a period of no more than about one week or no more than about two weeks after implantation of the vascular access port 400.

Once the membrane 282 has formed, methods of using the vascular access port 400 can proceed in the same manner as methods described above with respect to the vascular access port 100. For example, a clinician can palpate the skin of a patient to locate and determine the orientation of the vascular access port 400 in a manner similar to that illustrated in and discussed with respect to FIG. 11A.

As shown in FIG. 23C an access device 144 can directly access a lumen 262 of the vessel 200 via the vascular access port 400. In particular, FIG. 23C is similar to FIG. 11B and shows an initial access event. The access device 144 has been advanced through the skin of a patient to form an insertion tract 264 therein, has been advanced through the guidance passageway 430 (specifically, through the channel 434 and the distal opening 450 of the guidance passageway 430), through a lower end of the primary passageway 464, through the lower opening 466, and through the membrane 282. Stated otherwise, a central axis of the guidance passageway 430 (e.g., a central axis of the channel 434) extends through the lower opening 466, and the guidance passageway 430 constrains the access device 144 to move along the central axis and through the lower opening 466. The access device 144 thus can create an insertion site 266 in the vessel 200. Additional procedures relative to repeated access of the insertion site 266 via the vascular access port 400 can be as described above with respect to FIGS. 11C-11E.

Figure 24:
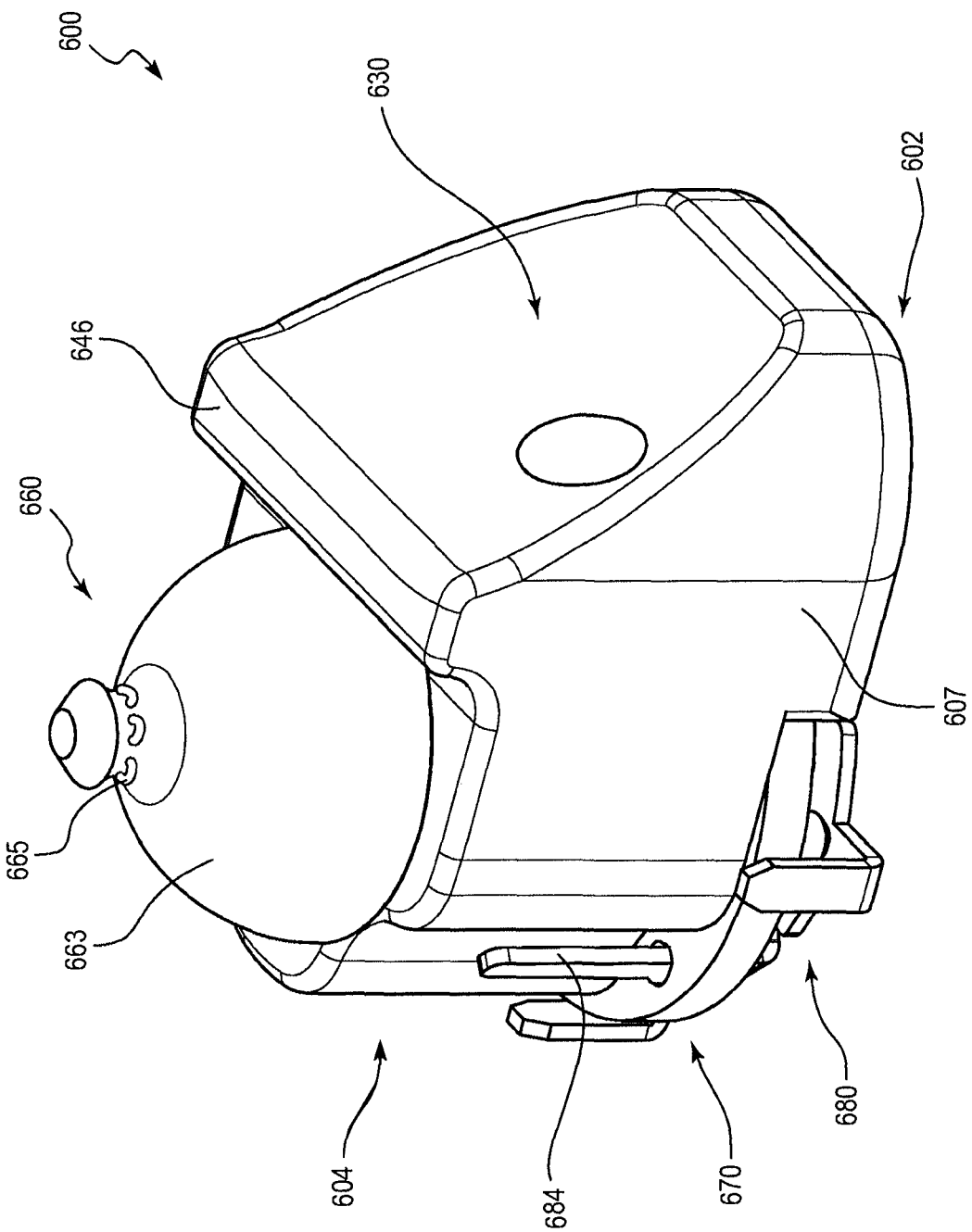
FIG. 24 is a top perspective view of another embodiment of a vascular access port coupled with another embodiment of a clip.
Figure 25:
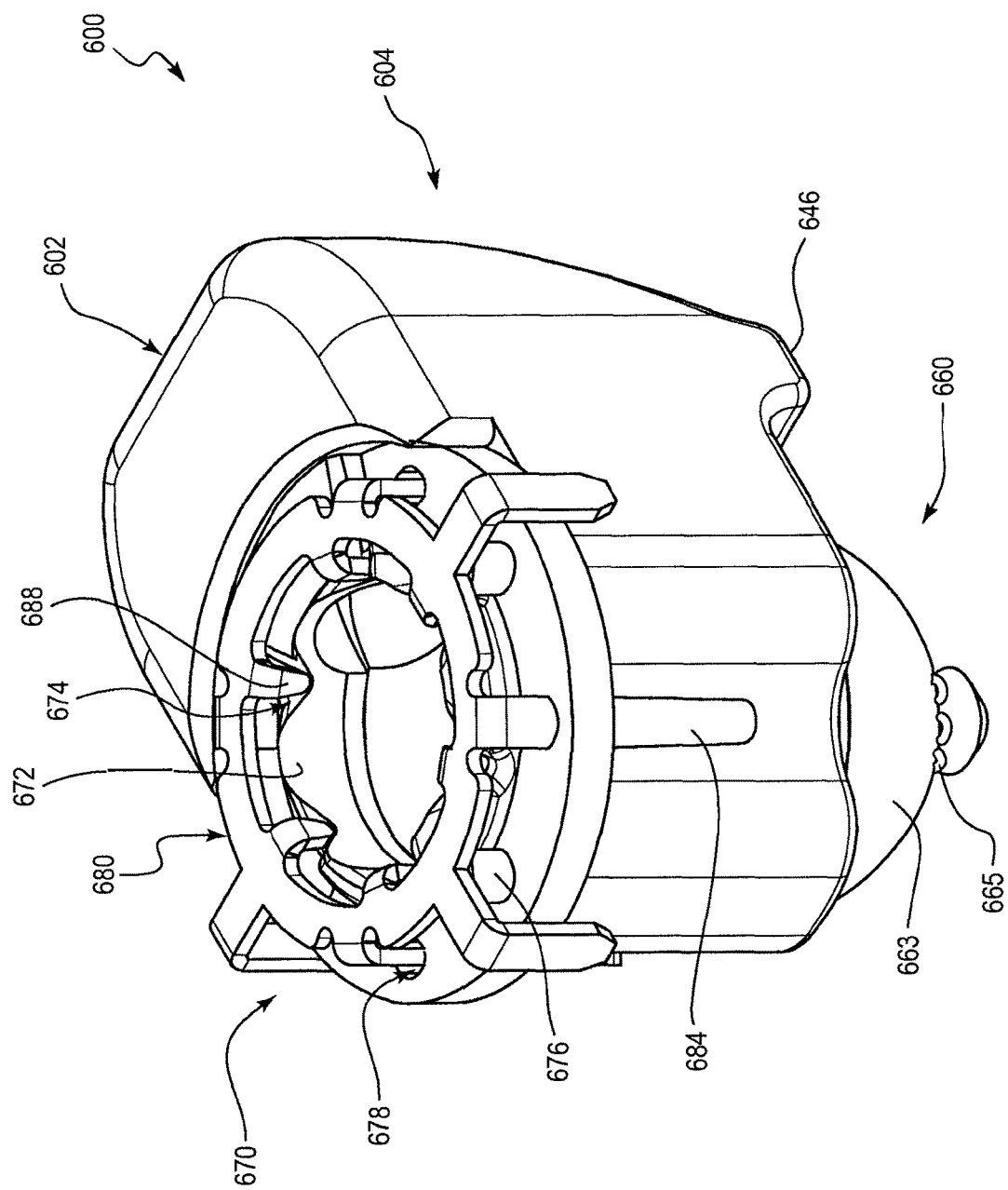
FIG. 25 is a bottom perspective view of the vascular access port and the clip of FIG. 24.

FIGS. 24 and 25 illustrate another embodiment of a vascular access port 600, which can resemble the vascular access ports 100, 400 described above. The vascular access port 600 can be implanted via a percutaneous method, such as by using the percutaneous implantation assembly 500 described above. The vascular access port 600 can include a base 602 and a body 604. An attachment region 670 of the base 602 can extend beyond an outer surface 607 of the body 604. In the illustrated embodiment, the attachment region 670 comprises a separate piece that is fixedly attached to the body 604. The attachment region 670 defines a plurality of connection channels 678, two of which extend through the base 602 and are spaced outwardly from the body 604, and two of which extend through the base 602 and into the body 604 but do not extend through an entirety thereof.

The connection channels 678 can be configured to receive therein connection posts 684 of a clip 680. In the illustrated embodiment, the each connection posts 684 includes a single prong, which thickens in a distal direction and is configured to provide an increasingly tight interference fit within a connection channel 678 as the clip 680 is approximated to the vascular access port 600.

The attachment region 670 can include attachment recesses 674 having sidewalls that are spaced further from each other at an entry end thereof and are rounded at a base thereof. As shown in FIG. 25, the entry ends of the attachment recesses 674 can be spaced from the teeth 688, which can permit the teeth 688 of the clip 680 to grip a vessel wall without puncturing it. The attachment region 670 can include everting members 672 that are interdigitated with the teeth 688 when the clip 680 is approximated to the vascular access port 600. Additionally, the attachment region 670 can include stops 676 that are positioned more centrally and contact a base ring 682 of the clip 680 when the clip 680 is approximated to the vascular access port 600.

The vascular access port 600 can include a seal or sealing device 660 at an upper end thereof. The sealing member 660 can include a tube 663 that is closed at an end thereof in any suitable manner, such as via a purse-string suture 665. The tube 663 can comprise any suitable material, such as, for example, one or more of urethane, polytetrafluoroethylene (PTFE), PGA, PLGA, Dacron, collagen, or any suitable resorbable material listed above.

In some embodiments, the tube 663 defines an outer diameter that is smaller than an inner diameter of a push tube 550 (see FIG. 22A) and an inner diameter that is larger than an outer diameter of a cutting tube 560 (see FIG. 22A). Accordingly, during implantation of the vascular access port 600, the tube 663 can be concentric with and positioned between the push tube 550 and the cutting tube 560. After the vascular access port 600 has been attached to a vessel, the push tube 550 and the cutting tube 560 can be removed. A proximal end of the tube 663 may be external to the skin of the patient at this stage, and can be clamped to prevent blood loss. The purse-string suture 665 could be in place prior to commencing the implantation, or can be provided after removal of the push tube 550 and the cutting tube 560. The purse-string suture 665 can be cinched tight, and the proximal portion of the tube 663 can be severed from a distal portion thereof at a position above the suture 665 (e.g., can be cut from the portion shown in FIGS. 24 and 25). The vascular access port 600 thus can be entirely subcutaneous once implanted. In other embodiments, the sealing device 660 can include a plug in place of the tube 663, which can be inserted into the vascular access port 600 after removal of the push tube 550 and the cutting tube 560.

The vascular access port 600 can include a single palpation projection 646 at an upper border of a guidance channel 630. In the illustrated embodiment, the palpation projection 646 is lower than an upper end of the tube 663.

Figure 26:
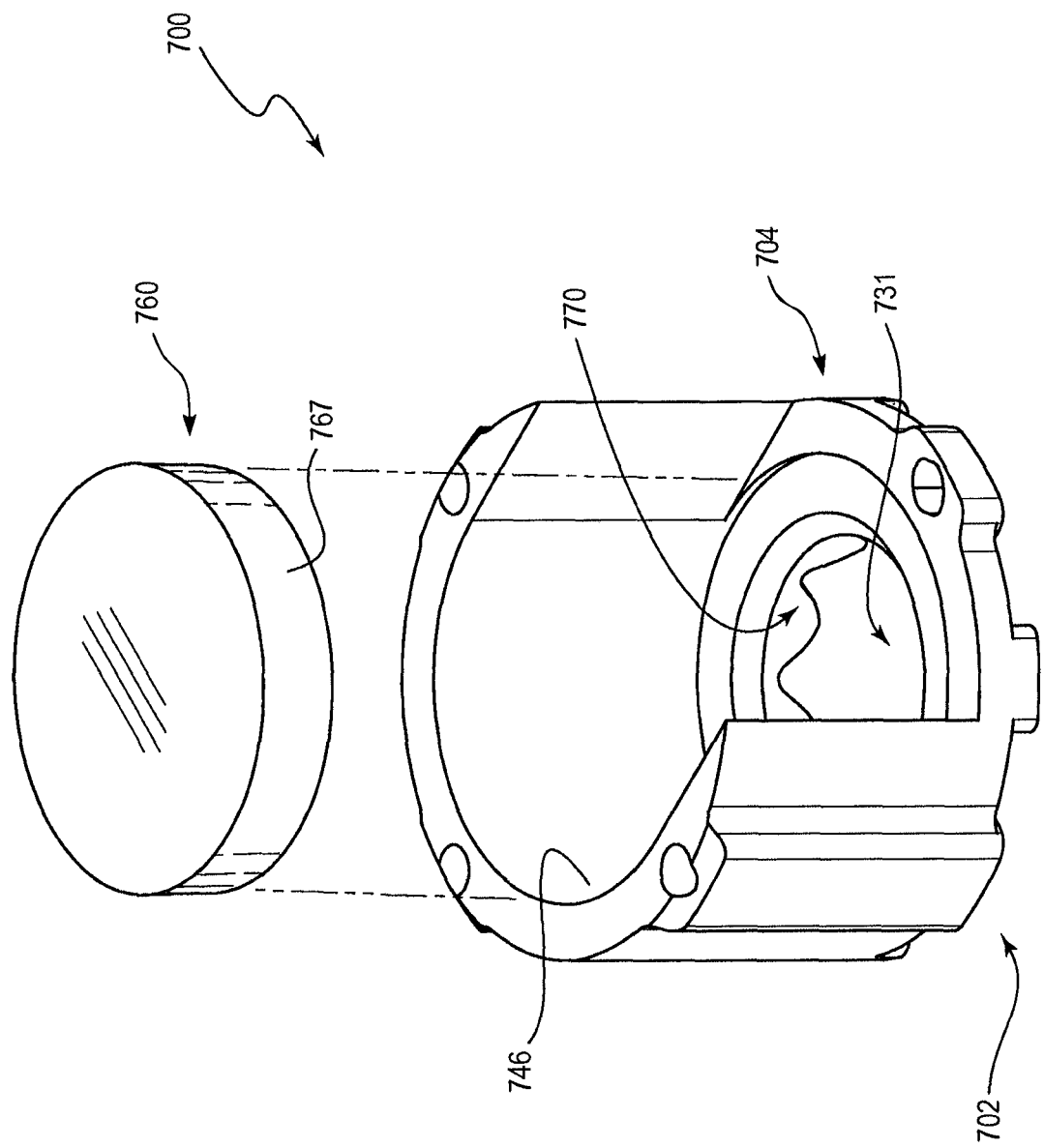
FIG. 26 is a perspective view of another embodiment of a vascular access port.

FIG. 26 illustrates another embodiment of a vascular access port 700, which can resemble the vascular access ports 100, 400, 600 described above. The vascular access port 700 can be implanted via a percutaneous method, such via the percutaneous implantation assembly 500 described above. The vascular access port 700 can include a base 702 and a body 704. The base 702 can include an attachment region 770 similar to the attachment region 670. Although a circular arrangement of the attachment region 770 is shown, other arrangements are also possible (e.g., oval-shaped).

A passageway 731 can extend through the body 702 and the base 702. The body 704 can include a palpation projection 746 that borders or encompasses a significant portion of the passageway 731. For example, in the illustrated embodiment, the palpation projection 746 encompasses more than ¾ of the passageway. An inner wall of the palpation projection 746 can be substantially perpendicular to a plane defined by a lower portion of the body 704. The palpation projection 746 can serve as a backstop that can prevent an access device 144 from overshooting the passageway 731. In other embodiments, the vascular access port 700 does not include a palpation projection 746.

The vascular access port 700 can include a sealing member 760, such as any of the sealing members 560, 660 described above. In the illustrated embodiment, the sealing member 760 comprises a plug 767, which can be resorbable or otherwise configured to be assimilated into the body and replaced with tissue. For example, the plug 767 can comprise any suitable material from the list of resorbable materials set forth above, collagen, plyurethane foam, etc. In some embodiments, the plug 452 comprises Surgicel®. Once the vascular access port 700 is implanted, a vessel membrane 282 can form over the passageway 731 and seal the contents of the vessel therefrom. In other embodiments, the vascular access port 700 can be implanted without a sealing member 760.

Figure 27:
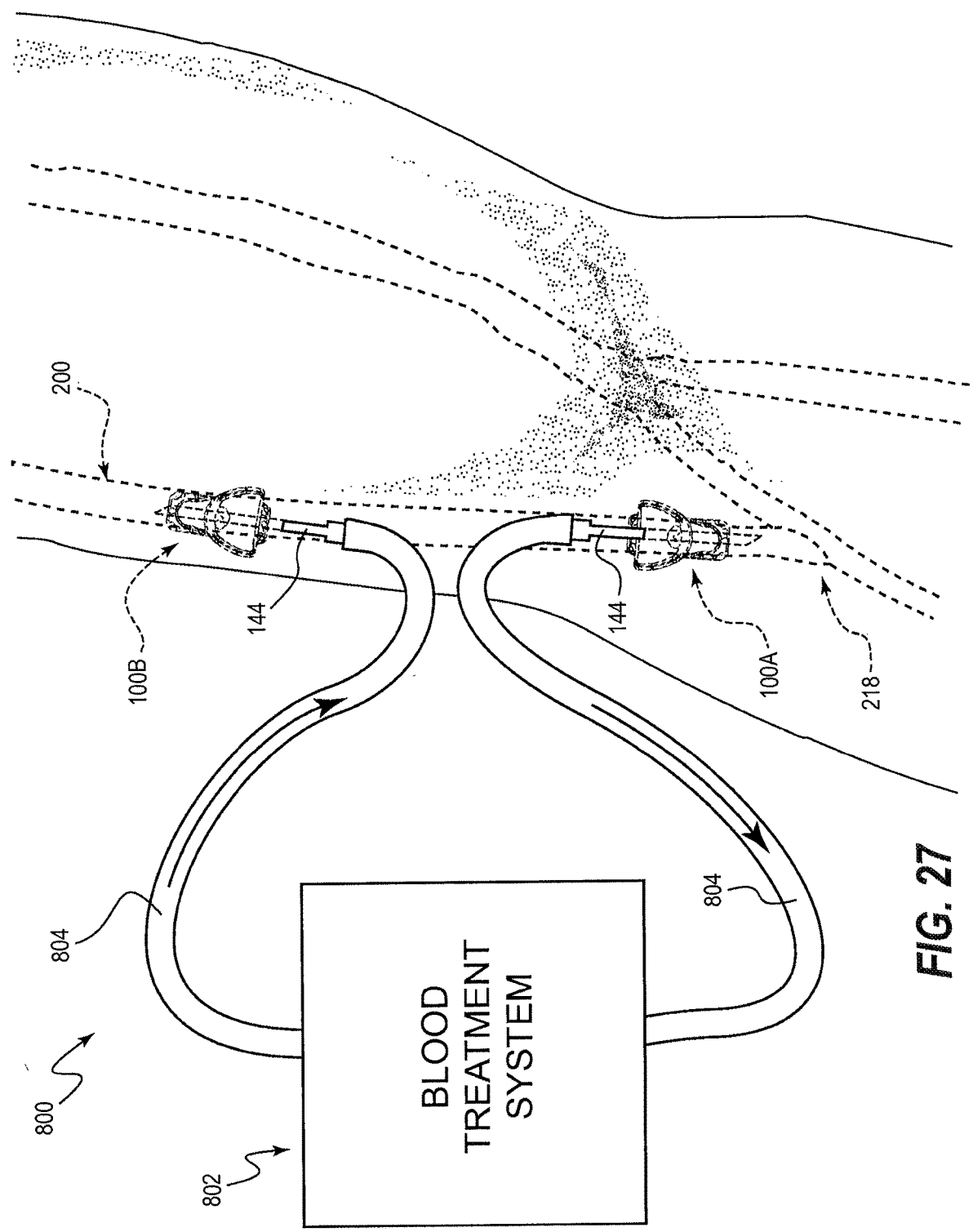
FIG. 27 is a perspective view of an embodiment of a vascular access system that can be used for the external treatment of blood.

FIG. 27 illustrates an embodiment of a system 800 configured for the external treatment of blood. The system 800 is similar to the system 300 described above. The system 800 includes two vascular access ports 100A, 100B, which can resemble any of the ports described above. Both of the ports 100A, 100B are shown attached to a vessel 200 that is associated with an arteriovenous fistula 218. One port 100A is directed upstream such that a forward end thereof points in a direction opposite to the flow of blood through the vessel 200, and the other port 100B is directed downstream such that a forward end thereof points in the direction of the blood flow through the vessel 200, although other arrangements are possible. A separate access device 144 (e.g., fistula needle or over-the-needle catheter) may be introduced into each of the ports 100A, 100B via any of the methods described above and connected to a blood treatment system 802 (e.g., hemodialysis machine) via any suitable passageways 2004 (e.g., tubing).

Blood treatment then can then be performed. The first port 100A can be an uptake port through which blood is removed from the vessel 200 and delivered to the blood treatment system 802, and the second port 100B can be a return port through which treated blood is returned to the vessel 200 from the blood treatment system 802. Accordingly, in use, blood is removed from the patient via an access device 144 that is within the first port 100A and delivered to the blood treatment system 802. The removed blood is treated in any suitable manner via the blood treatment system 802. Treated blood is returned to the patient via an access device 144 that is within the second port 100B.

In other embodiments, the system 800 can comprise only a single vascular access port 100A or 100B. Blood treatment may be conducted thereby via any suitable method (e.g., a single-needle hemodialysis technique). In still other embodiments, the system 800 includes more than two vascular access ports 100A, 100B. A clinician thus can rotate among the ports 100A, 100B, thereby leaving one or more of the ports unused during any given blood treatment session.

As can be appreciated from the foregoing, embodiments of vascular access ports can be sized and dimensioned to reside within a patient and beneath an outer surface of the skin of the patient. For example, the vascular access ports can be sized to fit between a vessel (e.g., any suitable artery or vein, such as, for example, the cephalic, basilic, femoral, jugular, or subclavian vein) and the epidermis of an animal subject.

Moreover, embodiments of one or more vascular access ports can be included in various embodiments of kits. For example, in some embodiments, a kit can comprise a vascular access port such as any of the ports described above. The kit can further include one or more of: one or more sutures or other attachment devices by which the port can be attached to a vessel, one or more synthetic grafts (which may be pre-attached to the port or separate therefrom), one or more pads of ingrowth-inducing material (which may be pre-attached to the port or separate therefrom), and one or more additional vascular access ports of the same configuration and/or of one or more different configurations (e.g., different size, shape, etc.). For example, in some embodiments, the kit can include multiple ports such that a practitioner can select one or more of the ports for implantation. In further embodiments, the kit can include ports of different sizes such that the practitioner can further select an appropriate port (or appropriate ports) based on the particular anatomy of a patient and/or on the target location of the port (or ports).

It is noted that while many of the examples provided herein relate to the use of vascular access ports with blood vessels, this method of disclosure is employed for the sake of convenience and efficiency, but should not be construed as limiting of the types of procedures with which embodiments may be used. Indeed, embodiments of the apparatus, methods, and systems disclosed herein can be used with vessels other than blood vessels, such as, for example, vessels within the gastrointestinal tract. Accordingly, the term "vessel" is a broad term that can include any hollow or walled organ or structure of a living organism, whether natural or synthetic.

It will be understood by those having skill in the art that changes may be made to the details of the above-described embodiments without departing from the underlying principles presented herein. For example, any suitable combination of various embodiments, or the features thereof, is contemplated.

Likewise, although symmetries are present in the illustrated embodiments, some embodiments may be asymmetrical. For example in some embodiments, a guidance passageway of a vascular access port may extend generally at an angle relative to a vertical longitudinal plane through the port such that a funnel region may more readily receive an access device therein at one side of the port as opposed to an opposite side thereof. Such arrangements may be beneficial in some applications where a port is implanted on a vessel that may more easily be reached from a direction that is not generally aligned with (e.g., nonparallel to) the vessel.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, although it is noted that in various embodiments, the height H of the vascular access port 100 is no greater than about 2, 3, 4, 5, 6, 7, 8, 9, 10, 11, 12, 13, 14, or 15 millimeters, it is understood that in some embodiments, the height H of the vascular access port 100 is no greater than 2, 3, 4, 5, 6, 7, 8, 9, 10, 11, 12, 13, 14, or 15 millimeters.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112 ¶ 6. Embodiments of the invention in which an exclusive property or privilege is claimed are defined as follows.

The invention claimed is:

1. A method of securing an access port to a vessel having a lumen, the method comprising:
    making an incision in a skin area such that the incision is substantially parallel to the vessel;
    exposing the vessel such that access to an outer wall of the vessel is maintained;
    positioning an access port adjacent to the wall of the vessel, the access port having a base and a body attached to the base, the base including a plurality of attachment passages, and a guidance passageway extending through the body and the base;
    securing the access port to the vessel by inserting an attachment device through at least one of the plurality of attachment passages and into the vessel; and
    closing the incision,
wherein the guidance passageway is not in fluid communication with the lumen of the vessel.

2. The method of claim 1, wherein the attachment device is a running suture that is inserted through all of the attachment passages in the securing step.

3. The method of claim 2, wherein the running suture is passed through all layers of the vessel in the securing step.

4. The method of claim 1, wherein the attachment device includes a plurality of sutures each of which is inserted individually into each attachment passage to secure the access port to the vessel.

5. The method of claim 1, wherein the attachment device is a pinch ring, a hook, or a wire.

6. The method of claim 1, wherein the incision is not made directly over the vessel.

7. The method of claim 1, wherein the vessel is a vein associated with an arteriovenous fistula.

8. The method of claim 7, wherein the attachment device is a running suture that is inserted through all of the attachment passages in the securing step.

9. The method of claim 8, wherein the running suture is passed through all layers of the vessel in the securing step.

10. The method of claim 7, wherein the attachment device includes a plurality of sutures each of which is inserted individually into each attachment passage to secure the access port to the vessel.

11. A method of securing an access port to a vessel, the method comprising:
    making a first incision in a skin area such that the incision is substantially parallel to the vessel, the vessel having an adventitia layer, a media layer, an intima layer, and a lumen;
    exposing the vessel such that access to the adventitia layer of the vessel is maintained;
    separating the adventitia layer from the underlying media layer;
    making a second incision in the adventitia layer;
    inserting an access port through the second incision;
    positioning the access port adjacent to the vessel, the access port having a base and a body attached to the base, the base including a plurality of attachment passages, and a guidance passageway extending through the body and the base;
    securing the access port to the vessel by inserting one or more attachment devices through the plurality of attachment passages and into the vessel; and
    closing the first incision,
wherein the adventitia layer extends over the guidance passageway and the guidance passageway is not in fluid communication with the lumen of the vessel.

12. The method of claim 11, wherein the attachment device is a running suture that is inserted through all of the attachment passages in the securing step.

13. The method of claim 12, wherein the running suture is passed through the adventitia layer, the media layer, and the intima layer of the vessel in the securing step.

14. The method of claim 11, wherein the attachment device includes a plurality of sutures each of which is inserted individually into each attachment passage to secure the access port to the vessel.

15. The method of claim 11, wherein, in the separating step, a portion of the adventitia layer remains attached to the media layer and the access port is placed on the attached portion of the adventitia layer in the positioning step.

16. The method of claim 11, wherein the incision is not made directly over the vessel.

17. The method of claim 11, wherein the vessel is a vein associated with an arteriovenous fistula.

18. The method of claim 17, wherein the attachment device is a running suture that is inserted through all of the attachment passages in the securing step.

19. The method of claim 17, wherein, in the separating step, a portion of the adventitia layer remains attached to the media layer and the access port is placed on the attached portion of the adventitia layer in the positioning step.

20. The method of claim 17, wherein the attachment device includes a plurality of sutures each of which is inserted individually into each attachment passage to secure the access port to the vessel.

* * * * *